(12) United States Patent
Yu

(10) Patent No.: US 6,600,026 B1
(45) Date of Patent: Jul. 29, 2003

(54) ELECTRONIC METHODS FOR THE DETECTION OF ANALYTES UTILIZING MONOLAYERS

(75) Inventor: Changjun Yu, Pasadena, CA (US)

(73) Assignee: Clinical Micro Sensors, Inc., Pasadena, CA (US)

( * ) Notice: Subject to any disclaimer, the term of this patent is extended or adjusted under 35 U.S.C. 154(b) by 0 days.

(21) Appl. No.: 09/306,653

(22) Filed: May 6, 1999

Related U.S. Application Data

(63) Continuation of application No. 09/135,183, filed on Aug. 17, 1998.
(60) Provisional application No. 60/084,652, filed on May 6, 1998, and provisional application No. 60/084,509, filed on May 6, 1998.

(51) Int. Cl.[7] .................. C07H 15/00; C07H 19/04; C07H 19/00; C07G 11/00
(52) U.S. Cl. .................. 536/17.1; 536/4.1; 536/26.26; 536/27.1; 536/28.1
(58) Field of Search .................. 536/4.1, 17.1, 536/26.26, 27.1, 28.1

(56) References Cited

U.S. PATENT DOCUMENTS

| | | | |
|---|---|---|---|
| 4,704,193 A | 11/1987 | Bowers et al. | |
| 4,711,955 A | * 12/1987 | Ward et al. | .................. 536/29 |
| 4,787,963 A | 11/1988 | MacConnell | |
| 5,089,112 A | 2/1992 | Skotheim et al. | |
| 5,180,968 A | 1/1993 | Bruckenstein et al. | |
| 5,241,060 A | * 8/1993 | Englehardt et al. | ............. 536/27 |
| 5,242,828 A | 9/1993 | Bergstrom et al. | |
| 5,356,786 A | 10/1994 | Heller et al. | |
| 5,391,272 A | 2/1995 | O'Daly et al. | |
| 5,436,161 A | 7/1995 | Bergstrom et al. | |
| 5,443,701 A | 8/1995 | Willner et al. | |
| 5,571,568 A | 11/1996 | Ribi et al. | |
| 5,632,957 A | 5/1997 | Heller et al. | |
| 5,700,667 A | 12/1997 | Marble et al. | |
| 5,795,453 A | 8/1998 | Gilmartin | |
| 5,837,859 A | 11/1998 | Teoule et al. | |
| 5,849,486 A | 12/1998 | Heller et al. | |
| 5,976,802 A | * 11/1999 | Ansorge et al. | .................. 435/6 |
| 6,060,023 A | 5/2000 | Maracas | |
| 6,060,327 A | 5/2000 | Keen | |
| 6,071,699 A | 6/2000 | Meade et al. | |
| 6,087,100 A | 7/2000 | Meade et al. | |
| 6,096,273 A | 8/2000 | Kayyem et al. | |
| 6,096,825 A | 8/2000 | Garnier et al. | |
| 6,107,080 A | 8/2000 | Lennox | |
| 6,177,250 B1 | 1/2001 | Meade et al. | |
| 6,180,352 B1 | 1/2001 | Meade et al. | |
| 6,200,761 B1 | 3/2001 | Meade et al. | |
| 6,203,758 B1 | 3/2001 | Marks et al. | |
| 6,207,369 B1 | 3/2001 | Wohlstadter et al. | |
| 6,238,870 B1 | 5/2001 | Meade et al. | |

FOREIGN PATENT DOCUMENTS

| | | |
|---|---|---|
| WO | 86/05815 | 10/1986 |
| WO | 93/22678 | 11/1993 |
| WO | 96/40712 | 12/1996 |
| WO | 98/20162 | 5/1998 |
| WO | 98/57159 | 12/1998 |
| WO | WO 99/57319 | 11/1999 |

OTHER PUBLICATIONS

Uto, Y. et al., "Electrochemical Analysis of DNA Amplified by the Polymerase Chain Reaction with a Ferrocenylated Oligonucleotide," Analytical Biochemistry, 250(250):122–124 (1997).

* cited by examiner

*Primary Examiner*—Jezia Riley
(74) *Attorney, Agent, or Firm*—Robin M. Silva; Renee M. Kosslak; Dorsey & Whitney, LLP

(57) ABSTRACT

The present invention relates to the use of self-assembled monolayers with mixtures of conductive oligomers and insulators to detect target analytes.

12 Claims, 41 Drawing Sheets

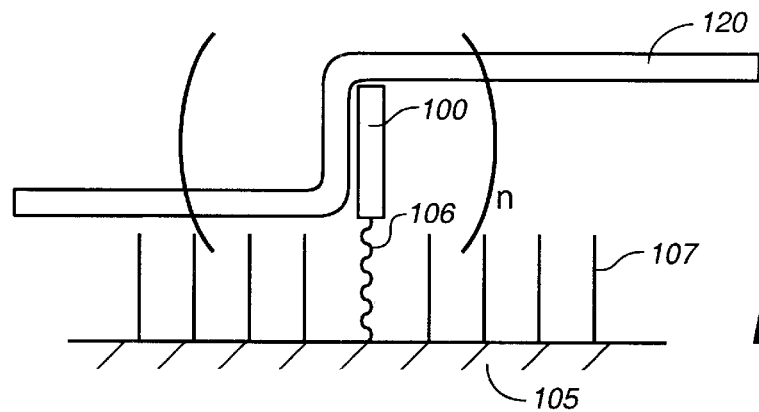
FIG._1A
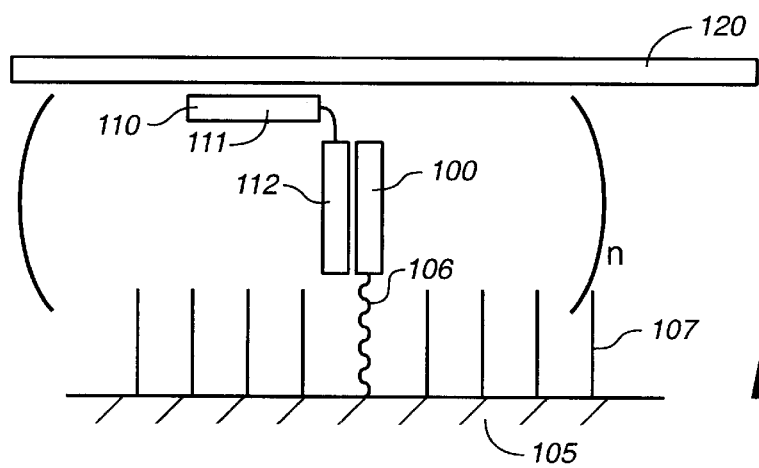
FIG._1B
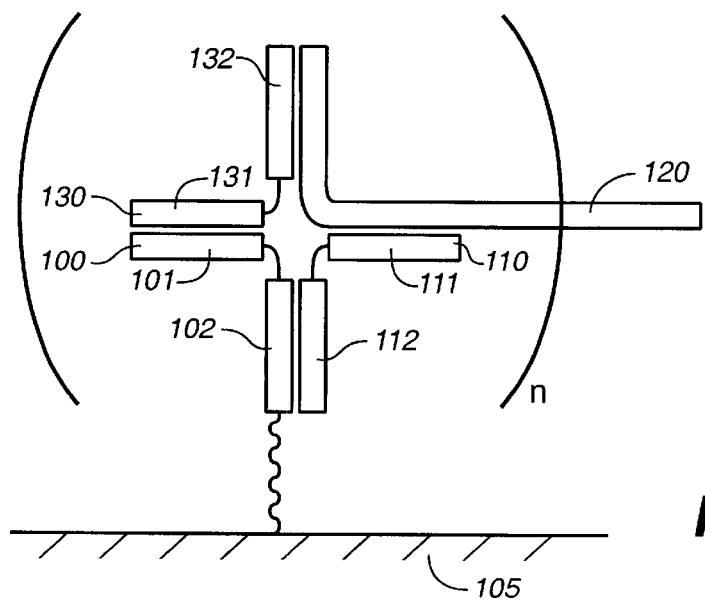
FIG._1C

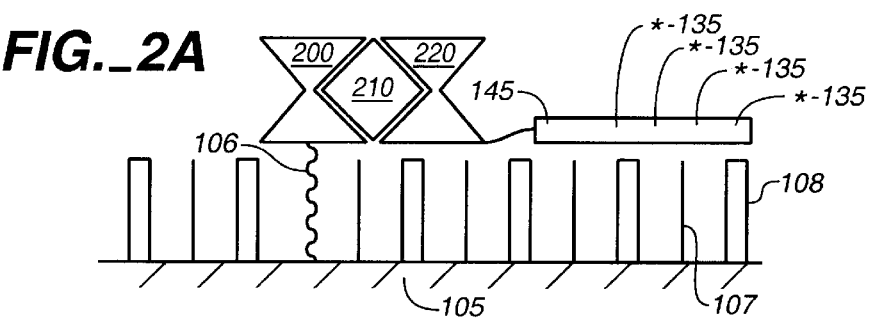
FIG._2A
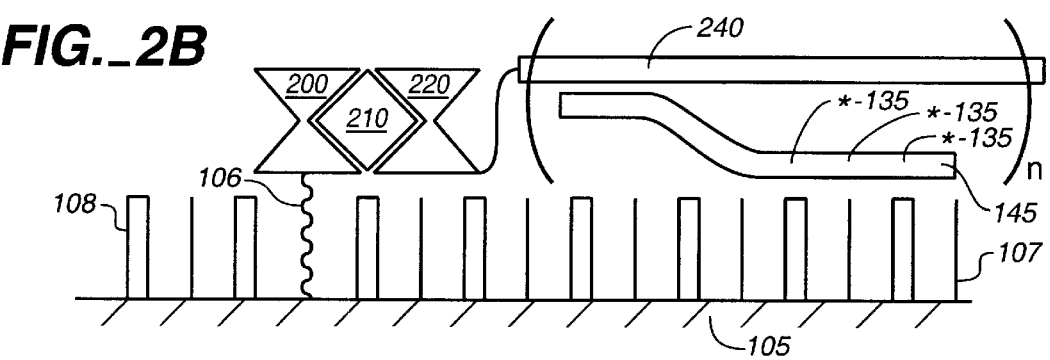
FIG._2B
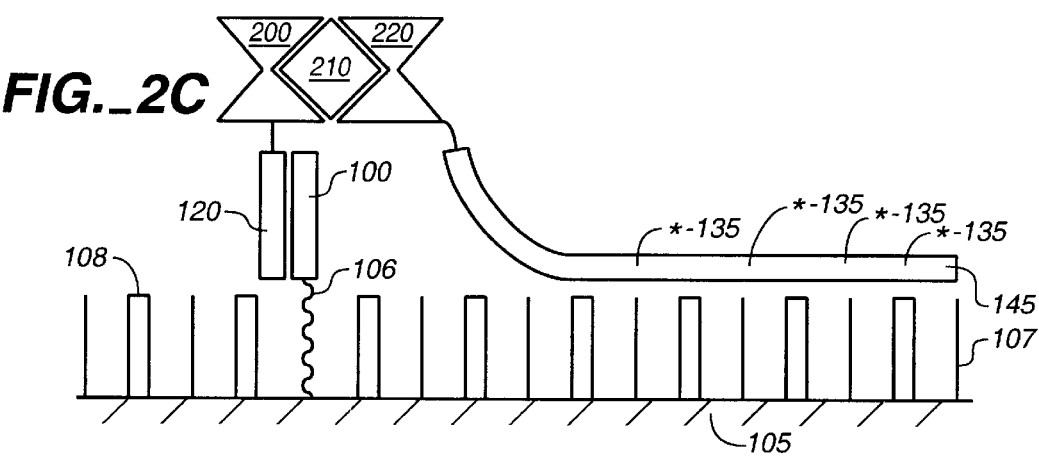
FIG._2C
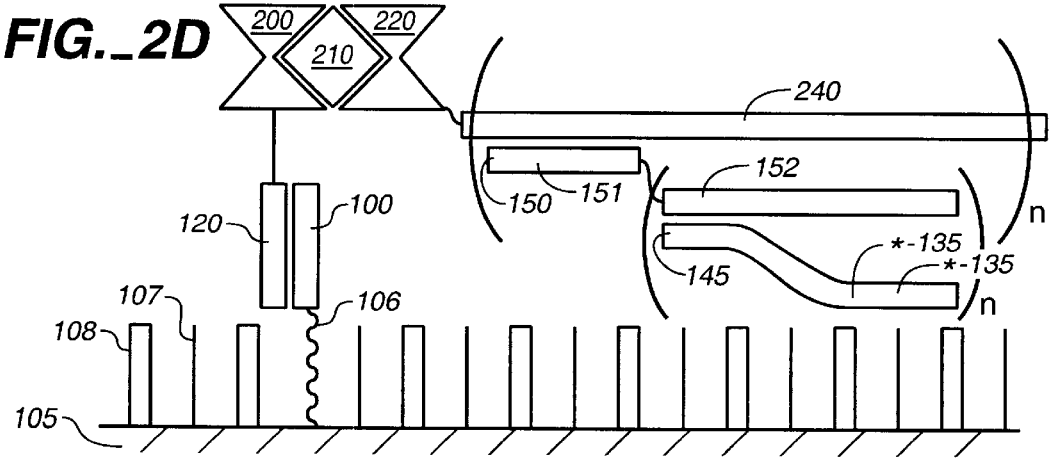
FIG._2D

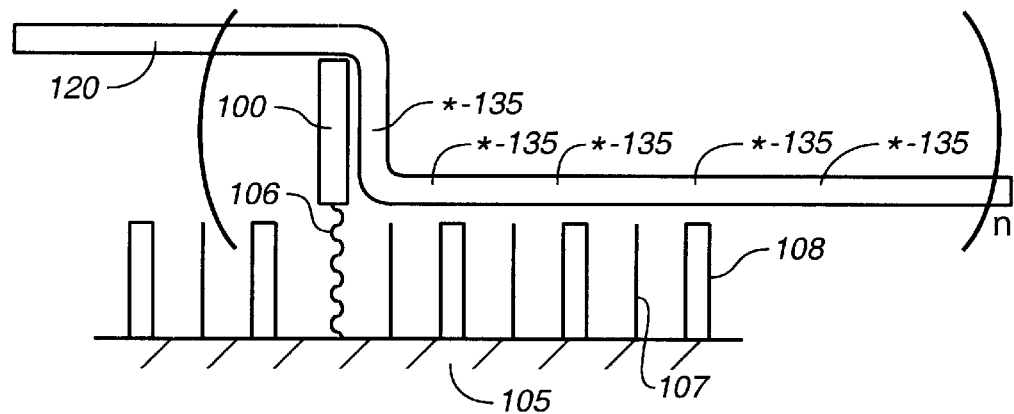
FIG._3A
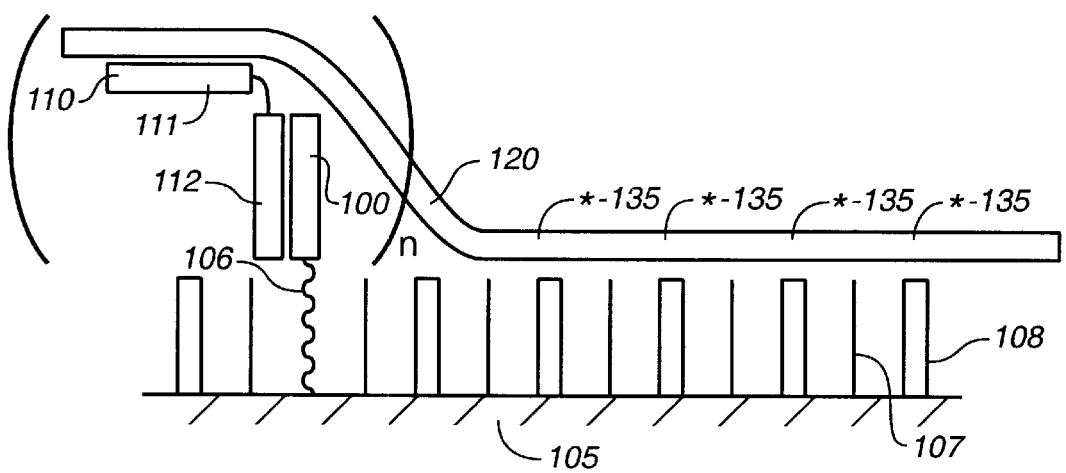
FIG._3B
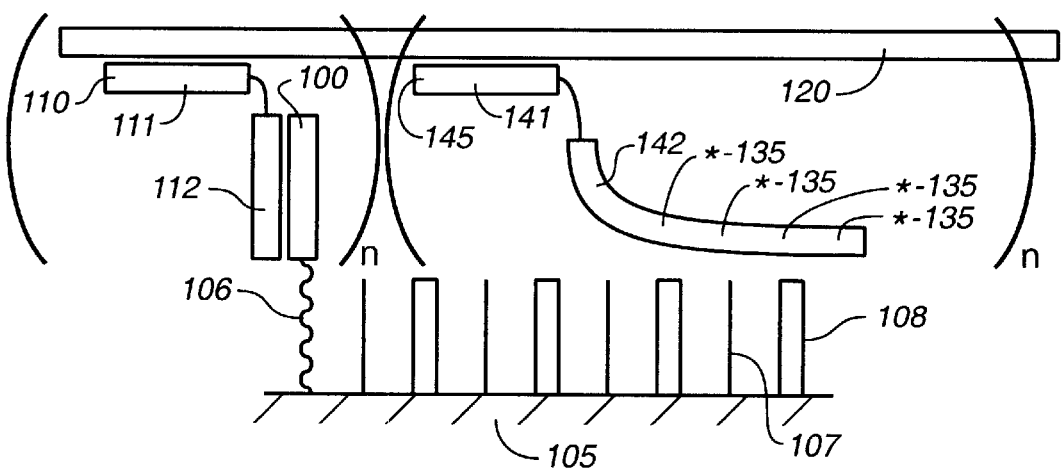
FIG._3C

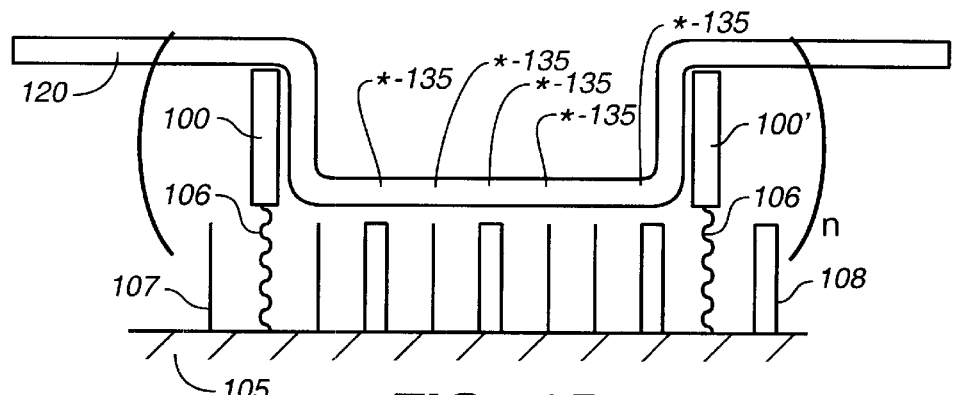
FIG._3D
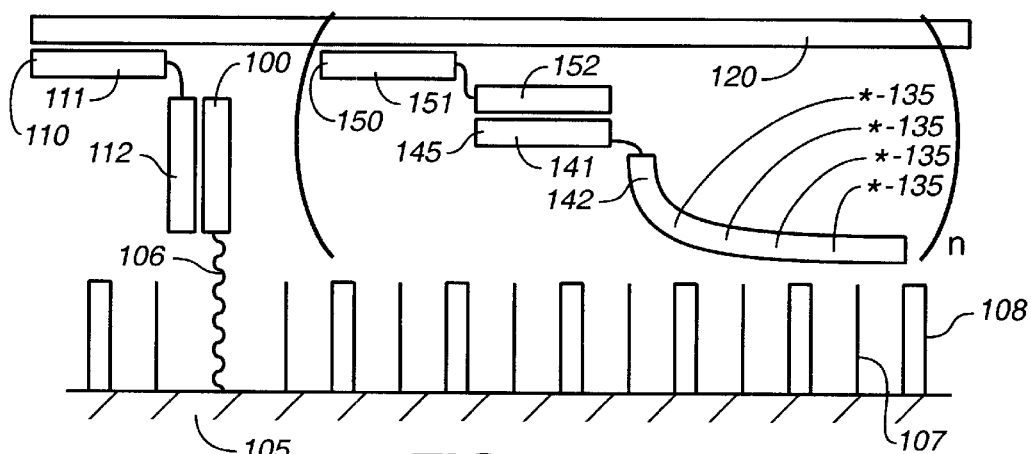
FIG._3E
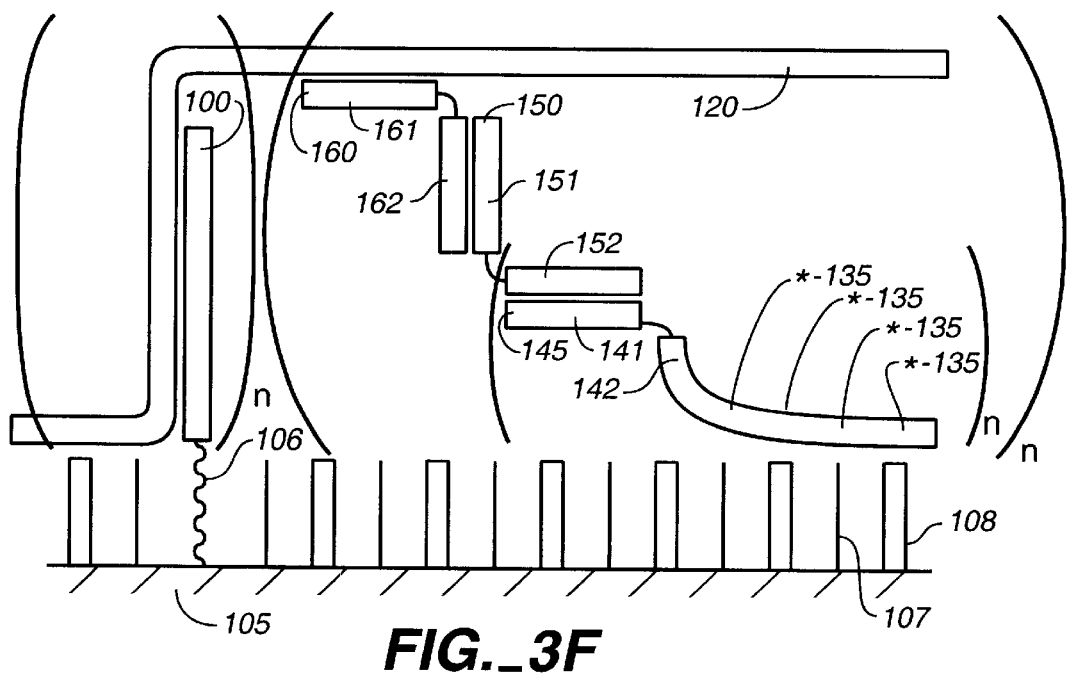
FIG._3F

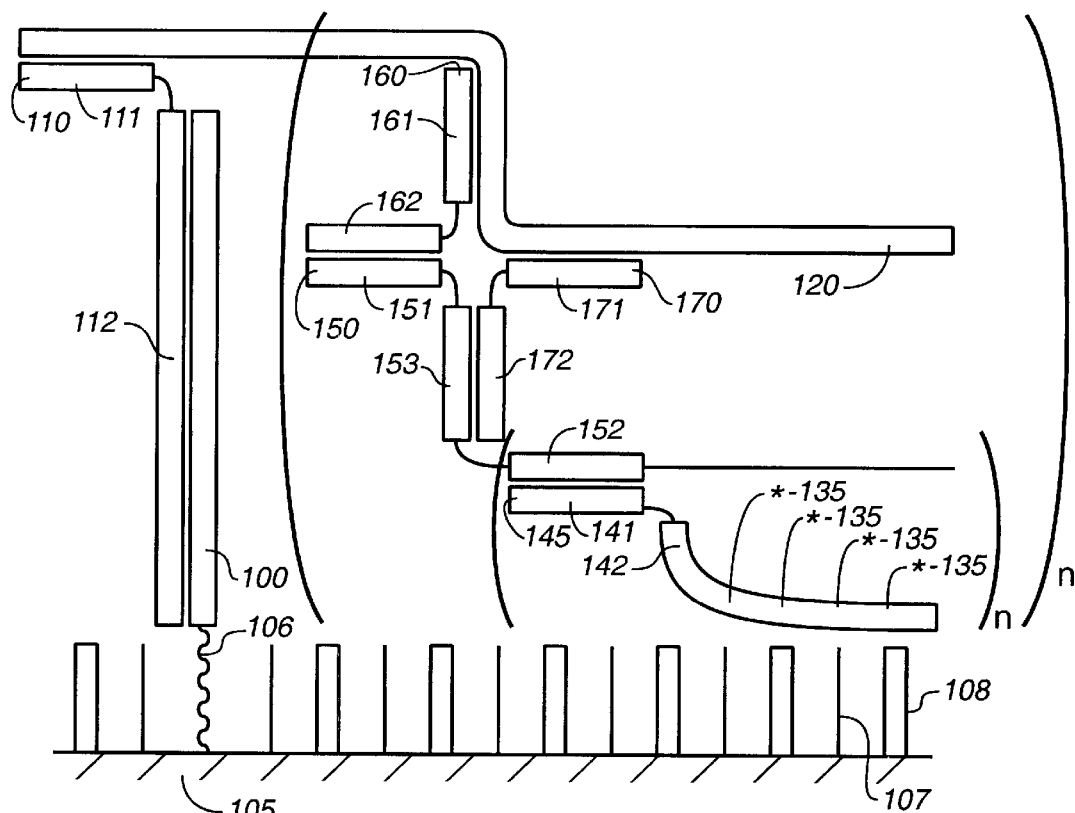
FIG._3G
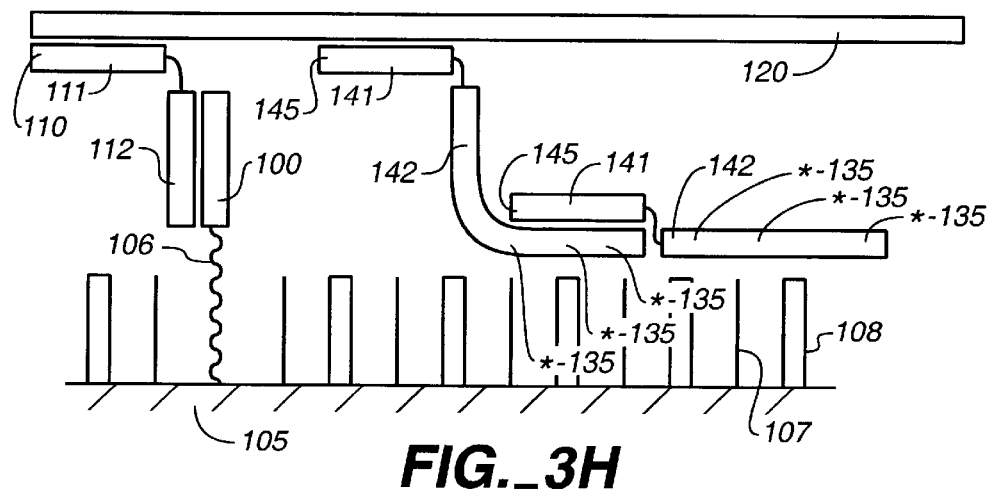
FIG._3H

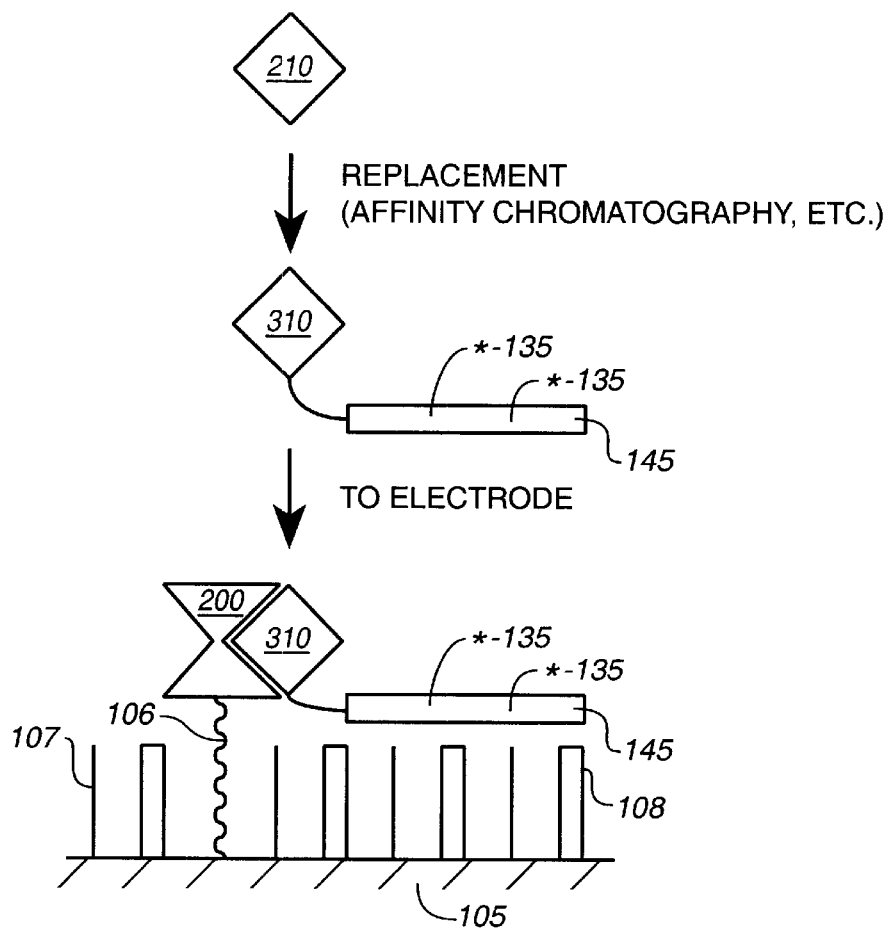
FIG._4A
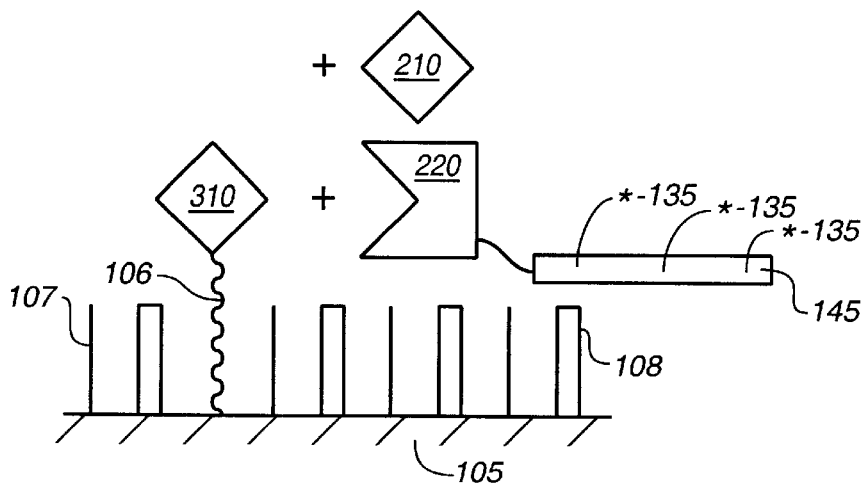
FIG._4B

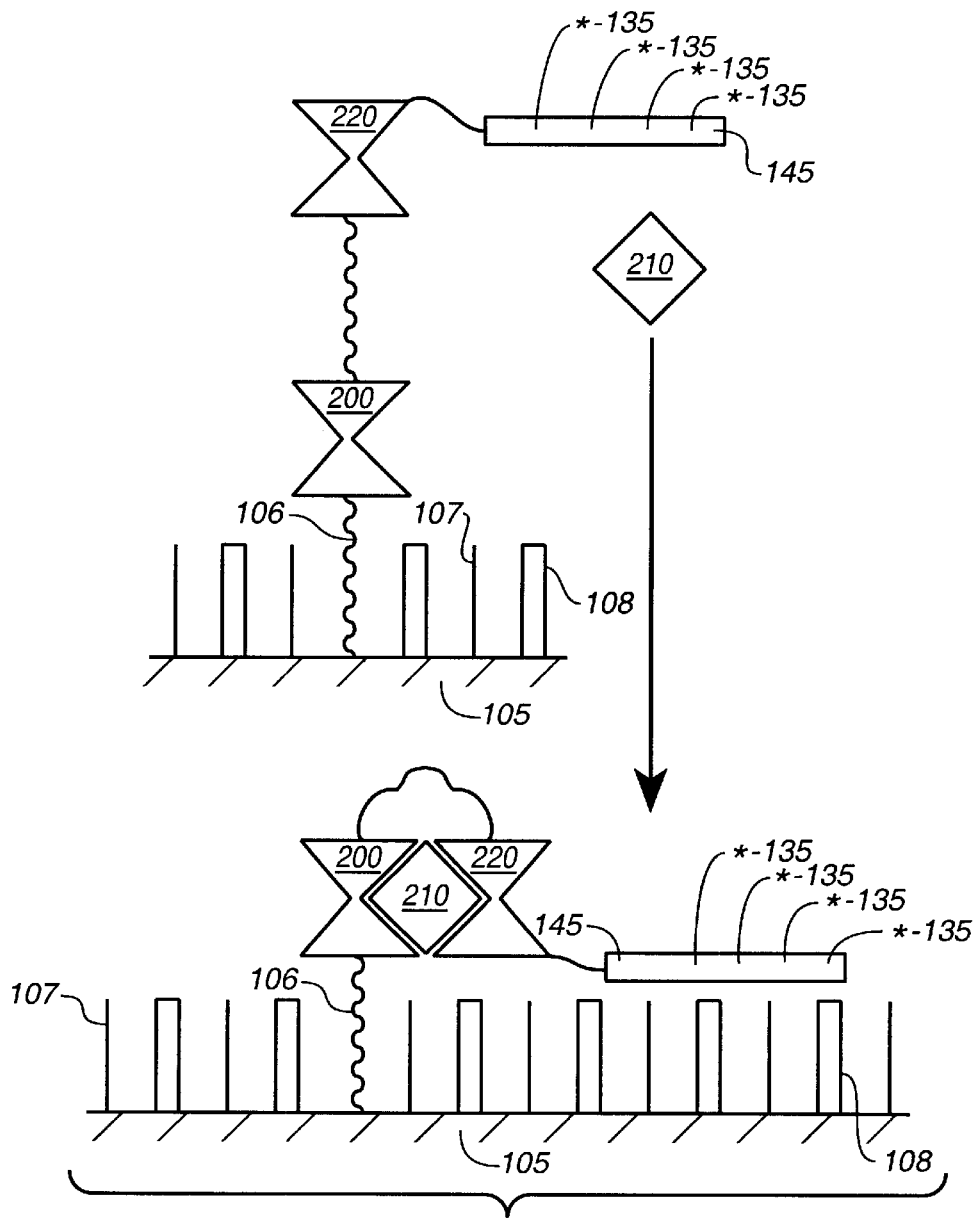
FIG._5A
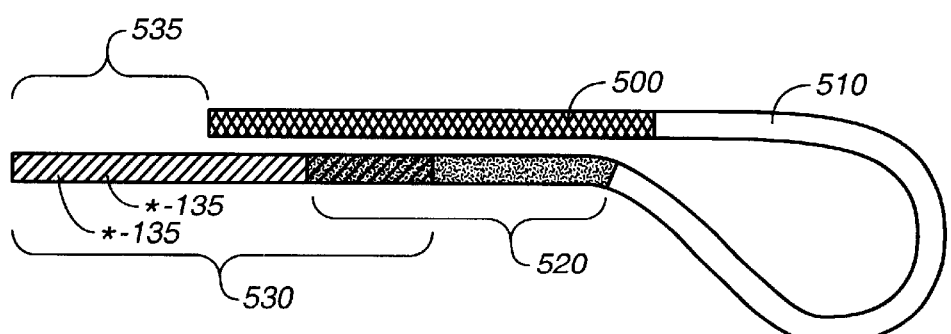
FIG._8

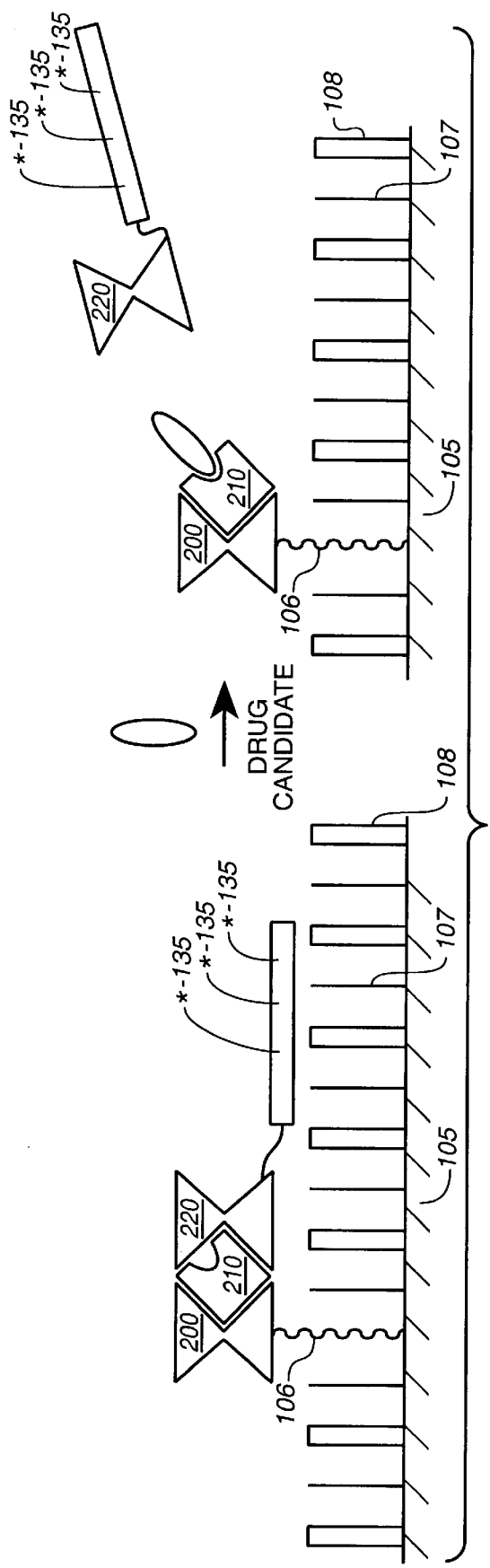
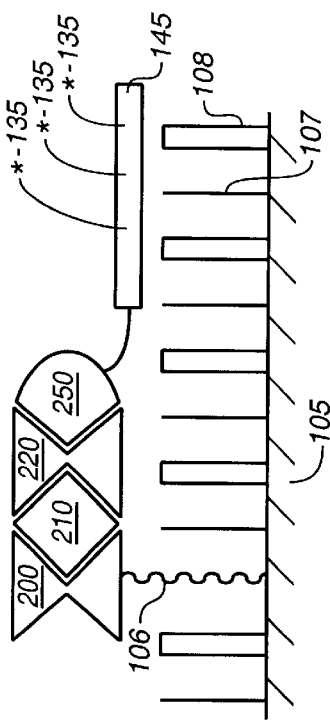
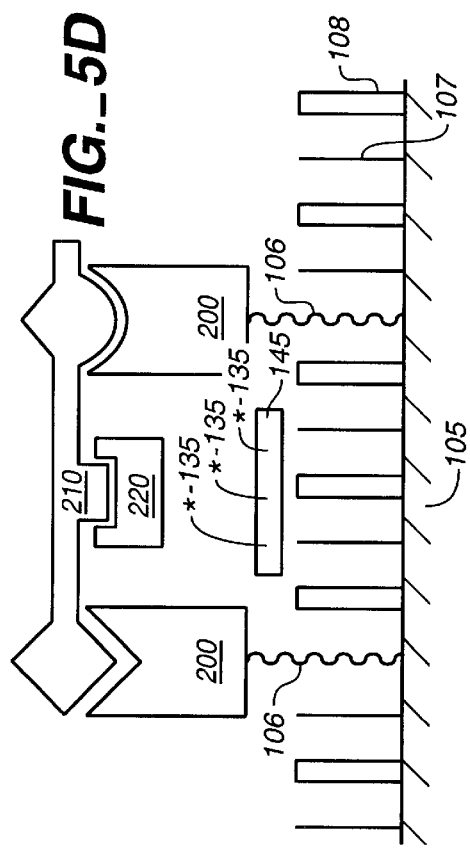
*FIG._5B*
*FIG._5D*
*FIG._5E*

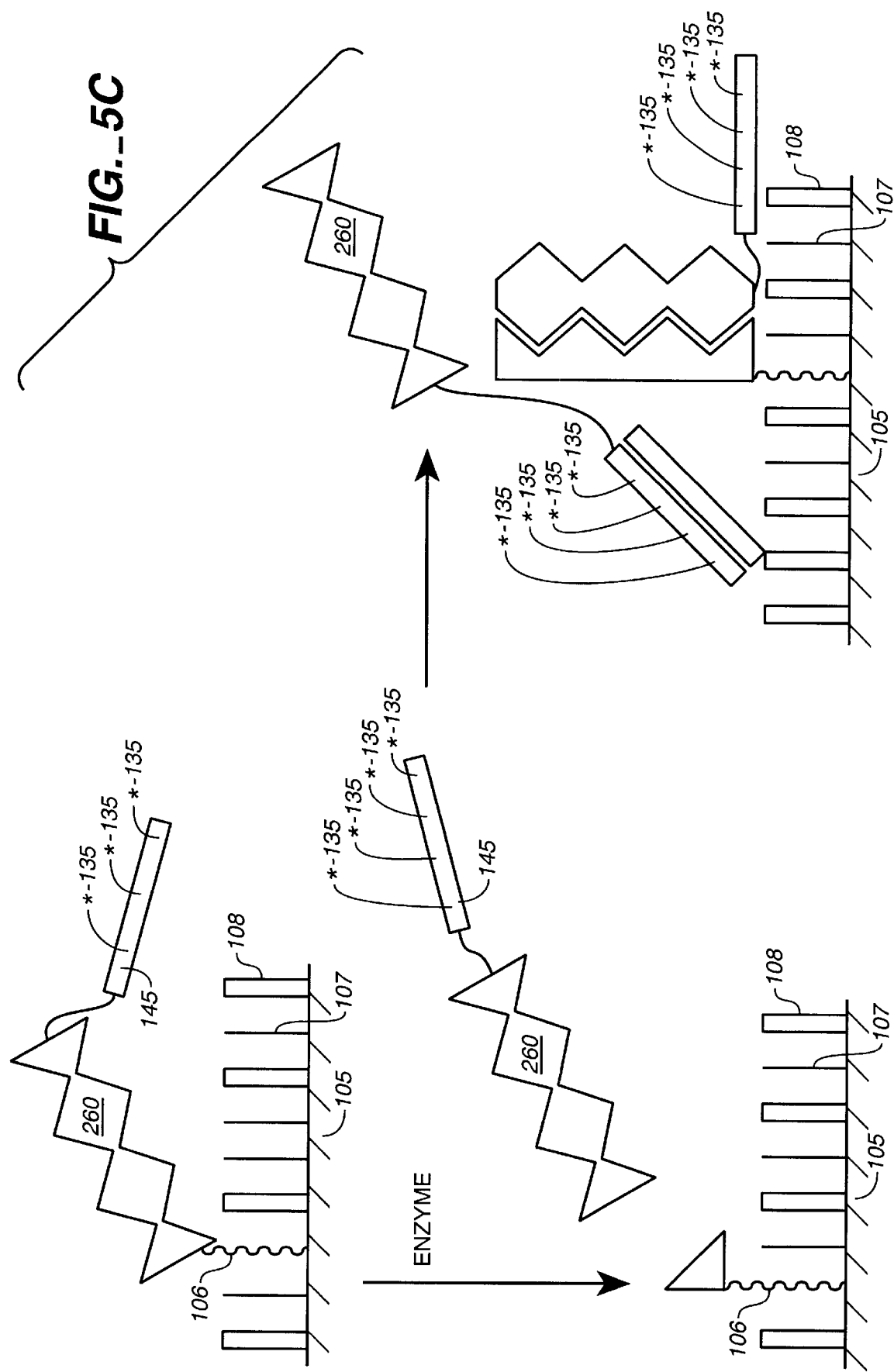

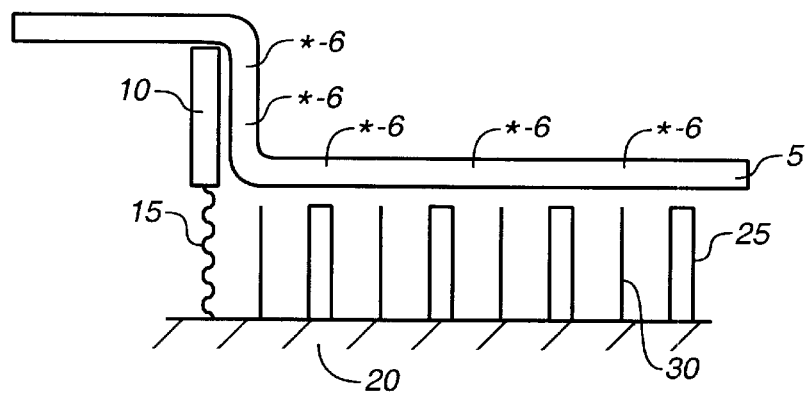
FIG._6A
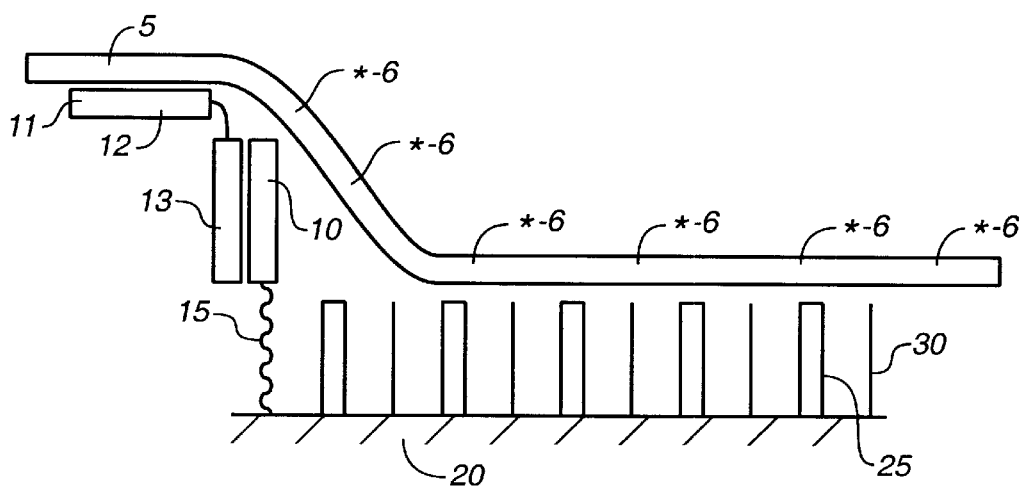
FIG._6B
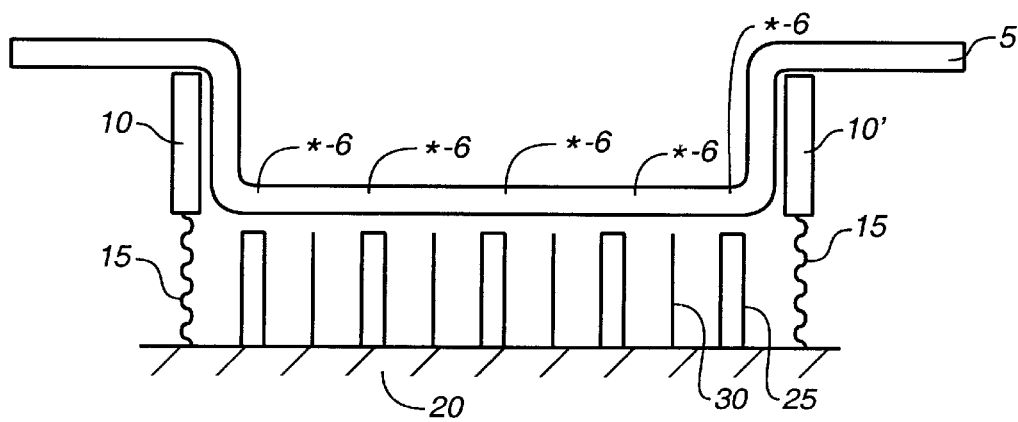
FIG._6C

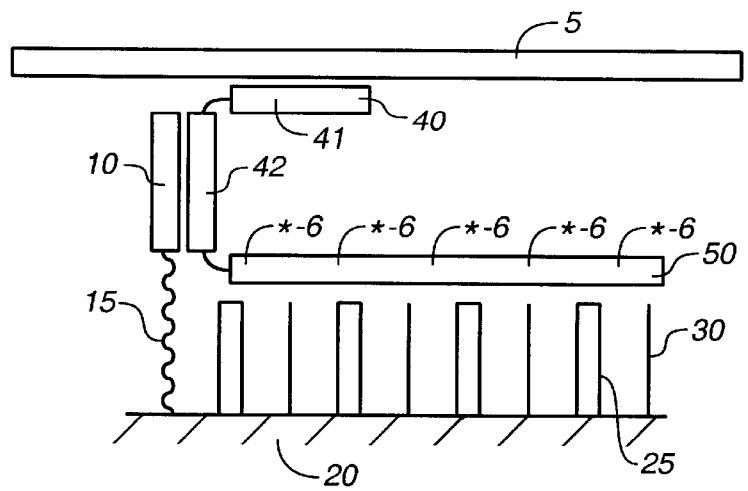
FIG._6D
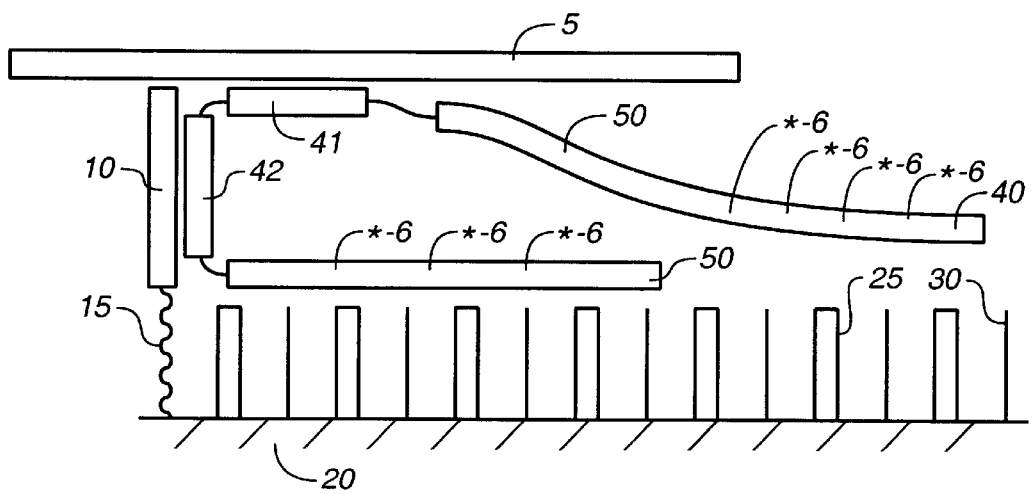
FIG._6E
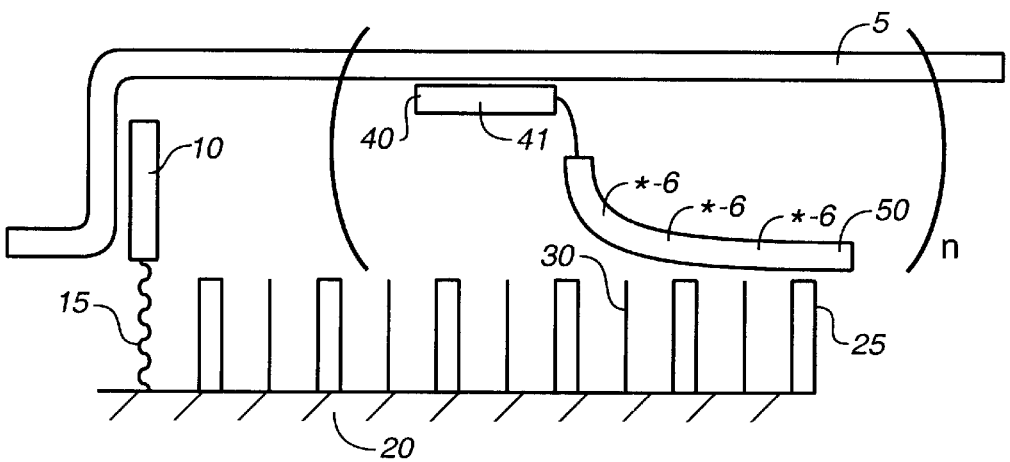
FIG._6F

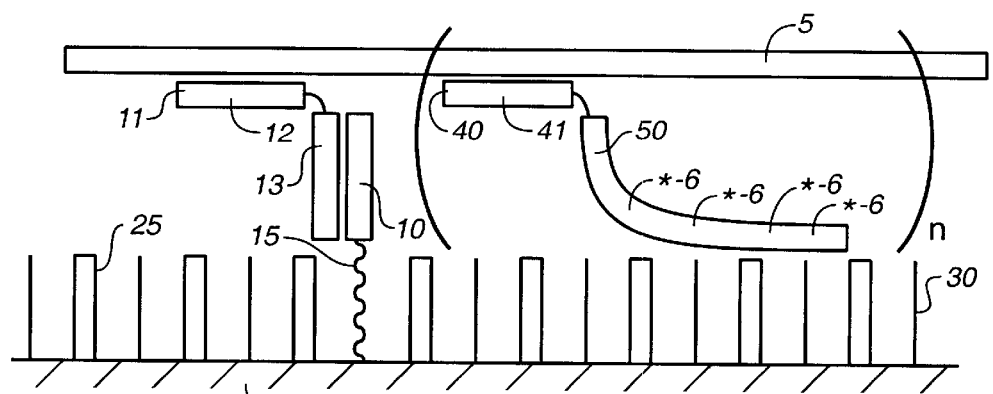
FIG._6G
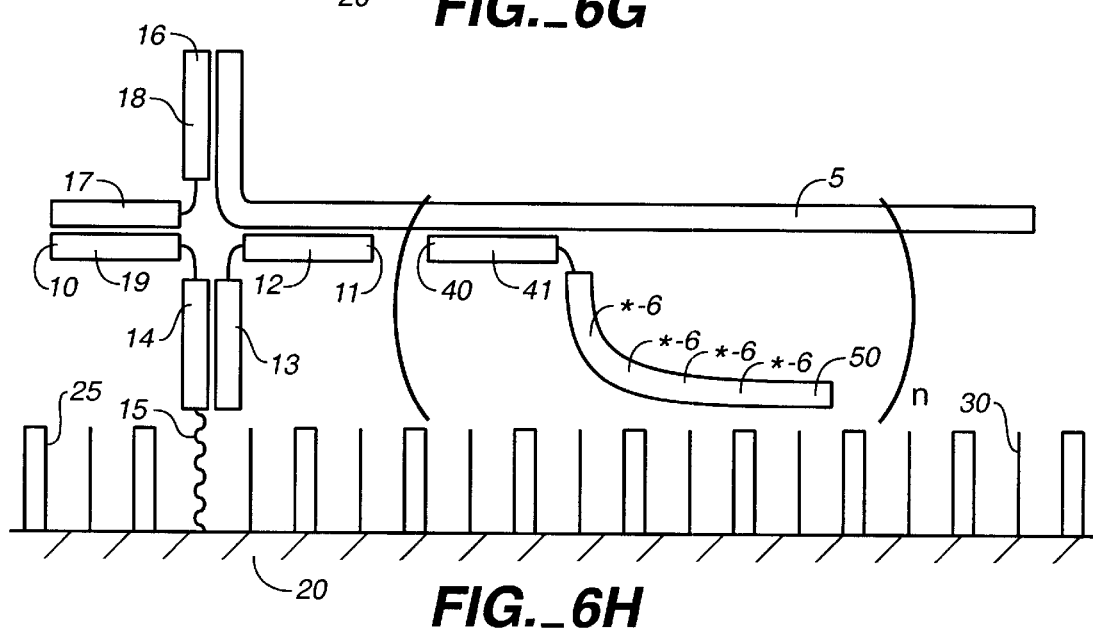
FIG._6H
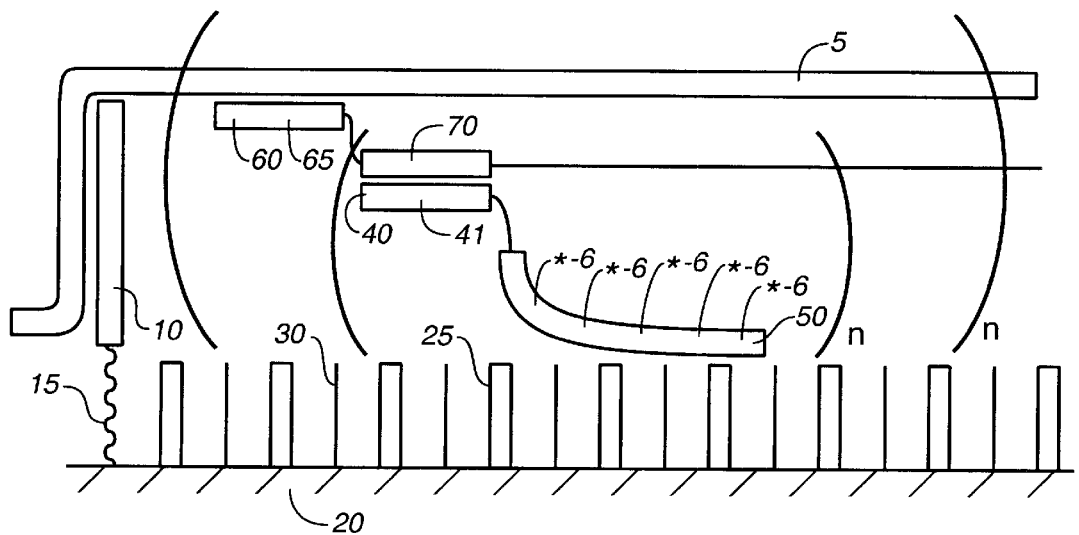
FIG._6I

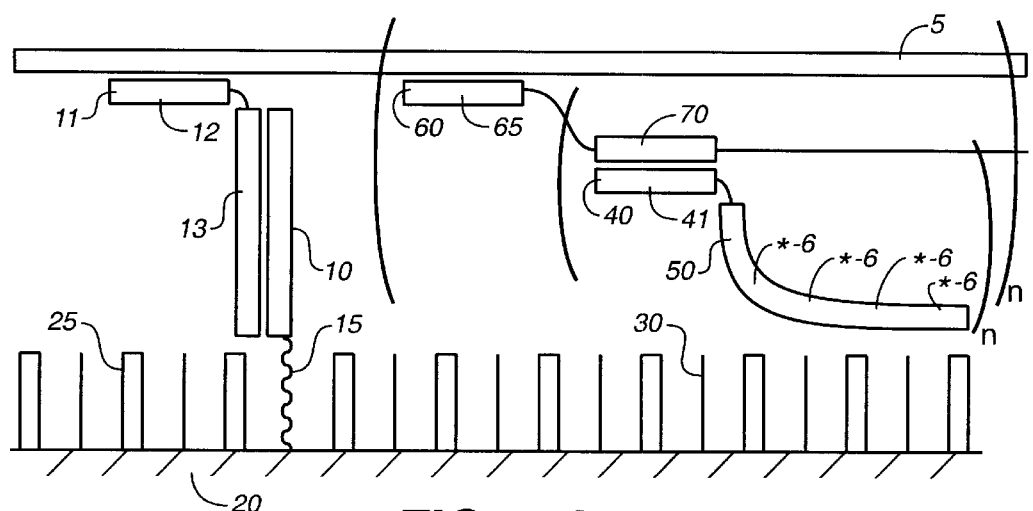
FIG._6J
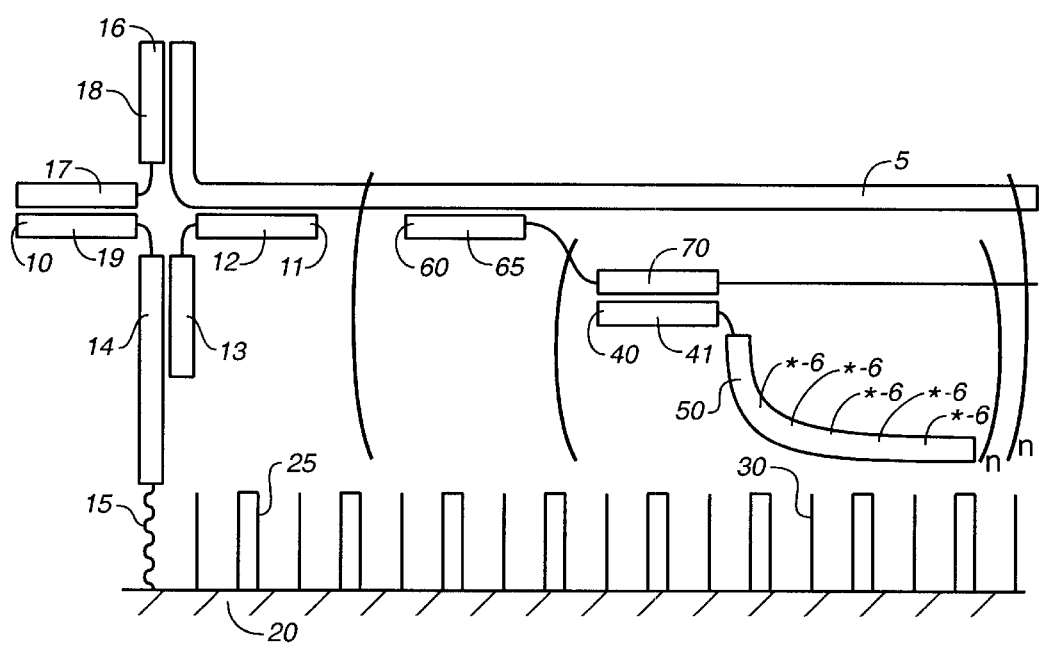
FIG._6K

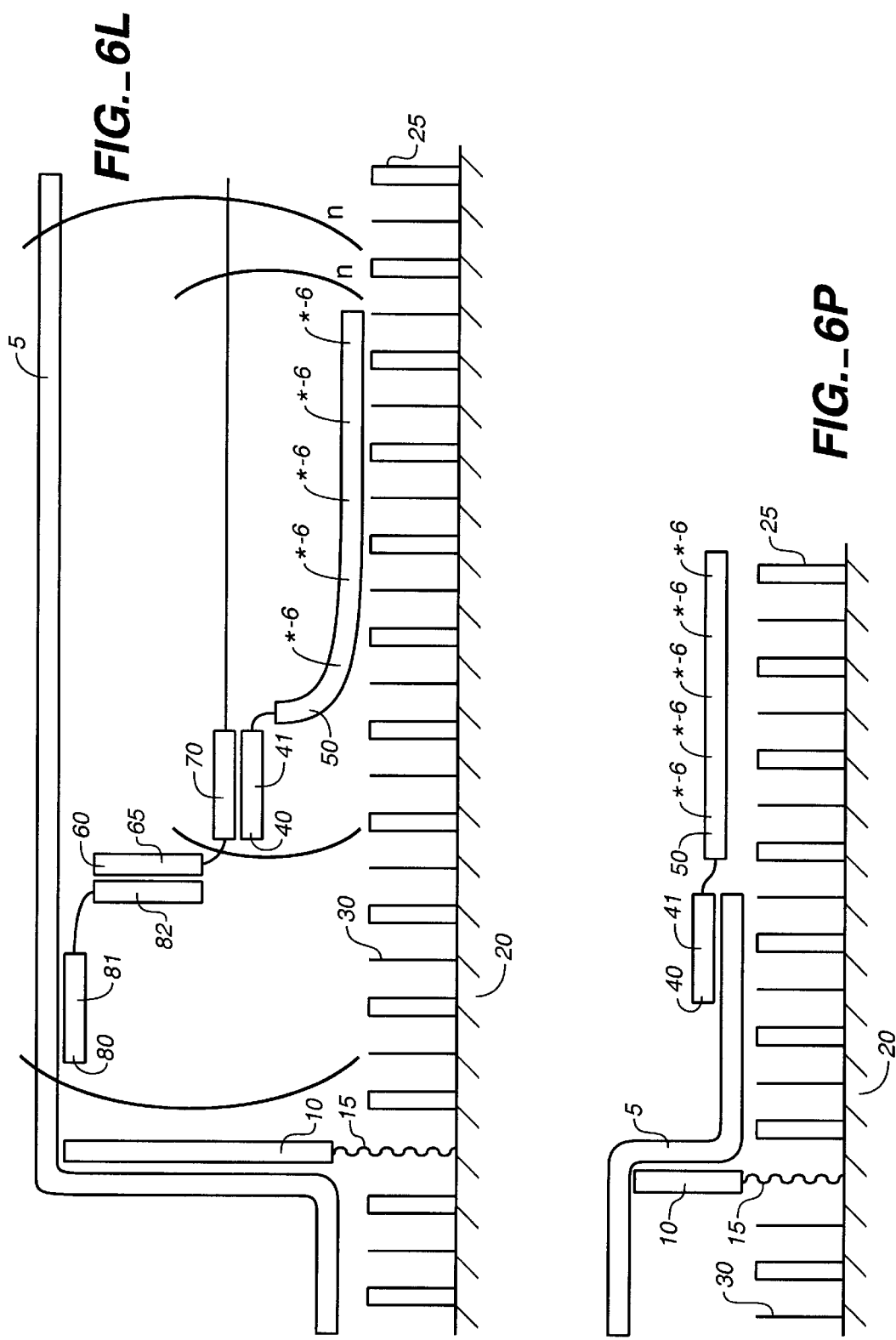

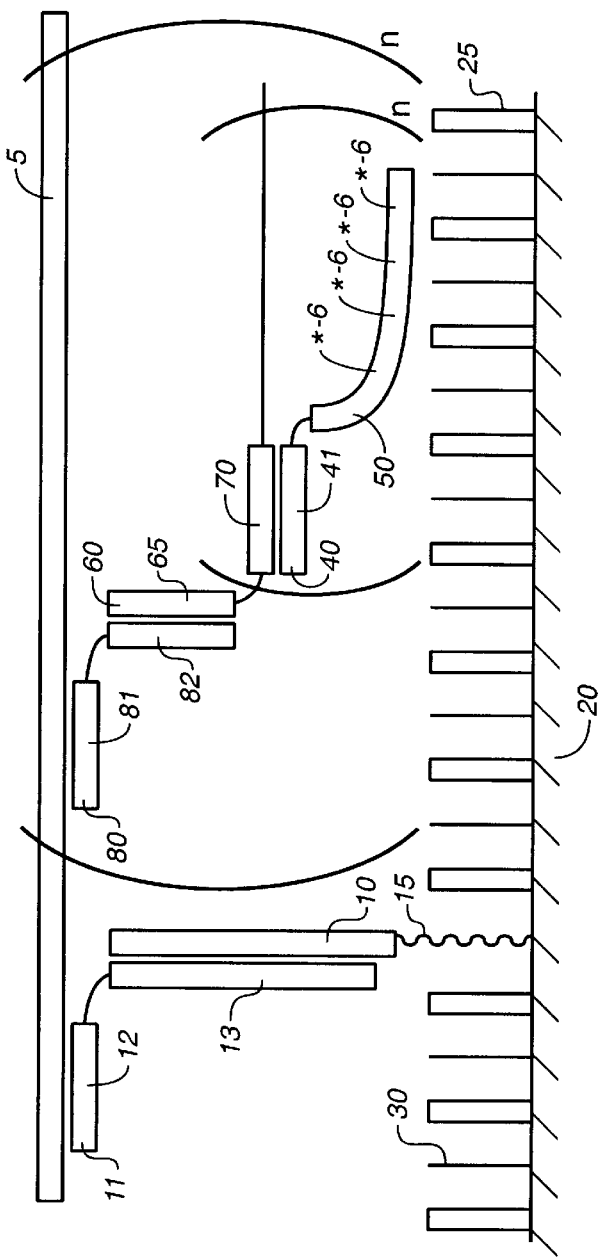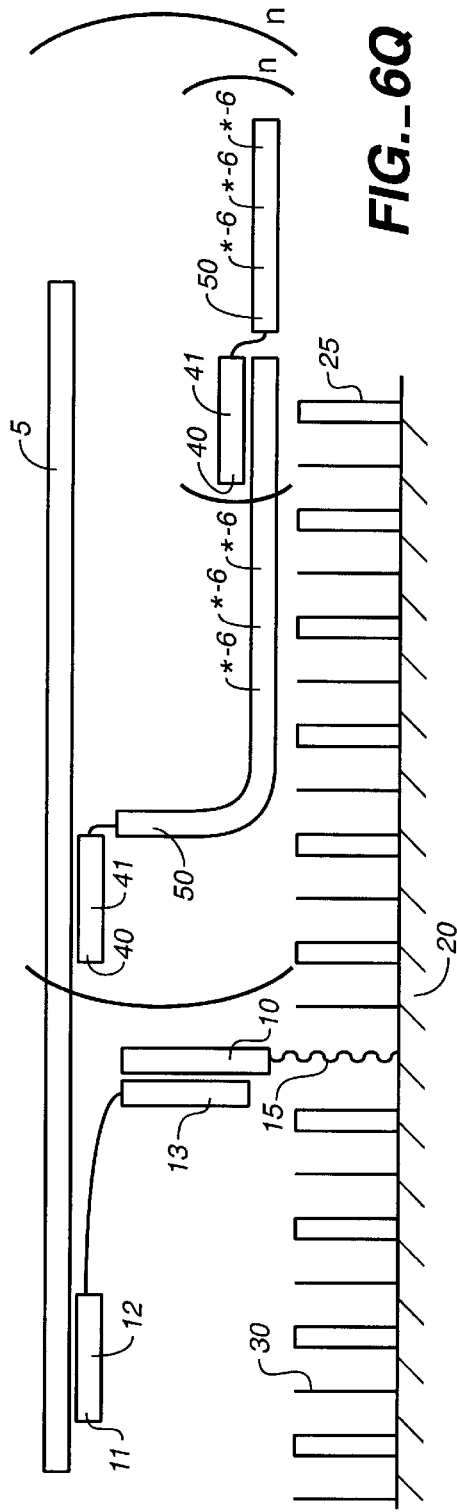

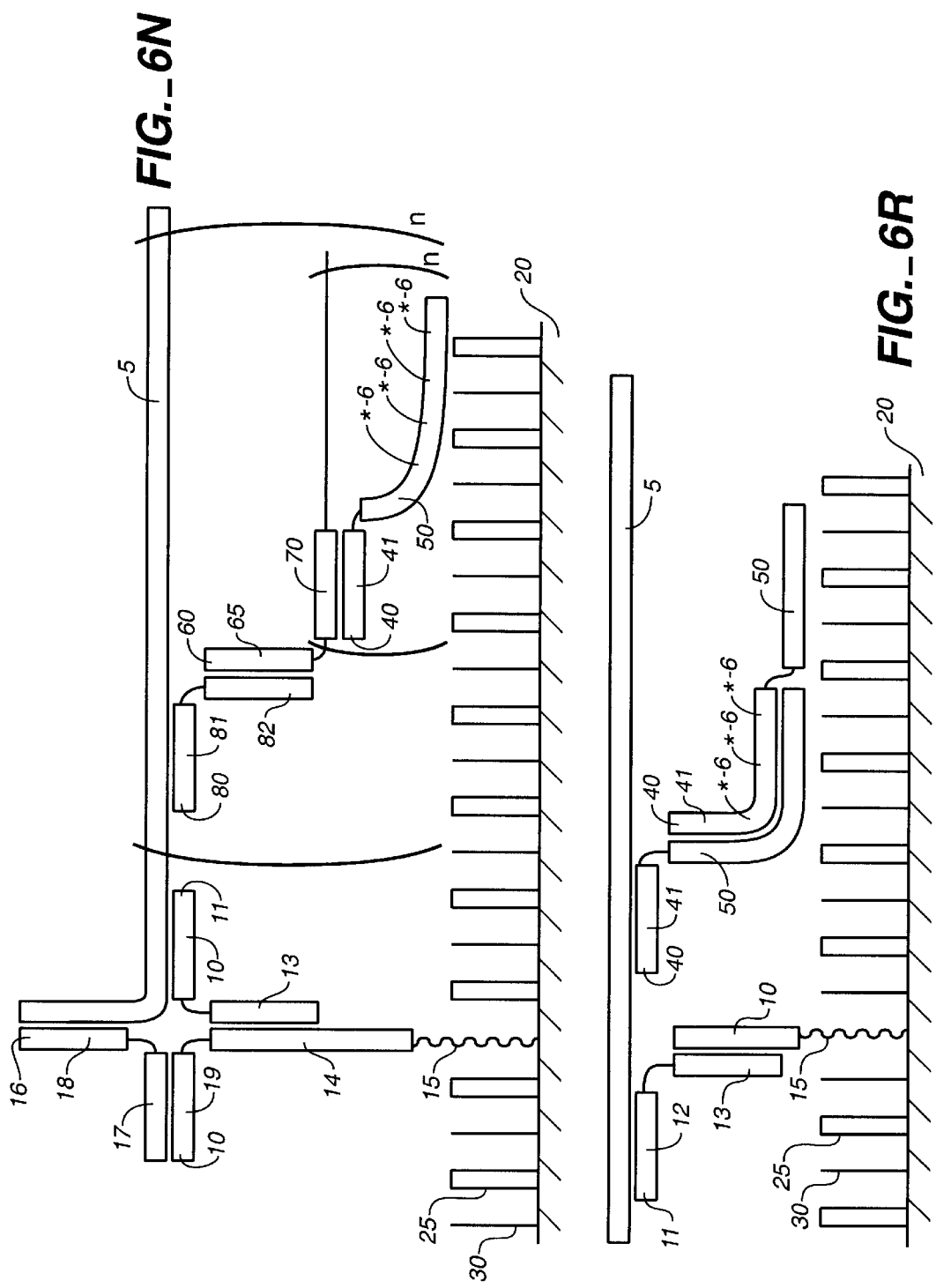

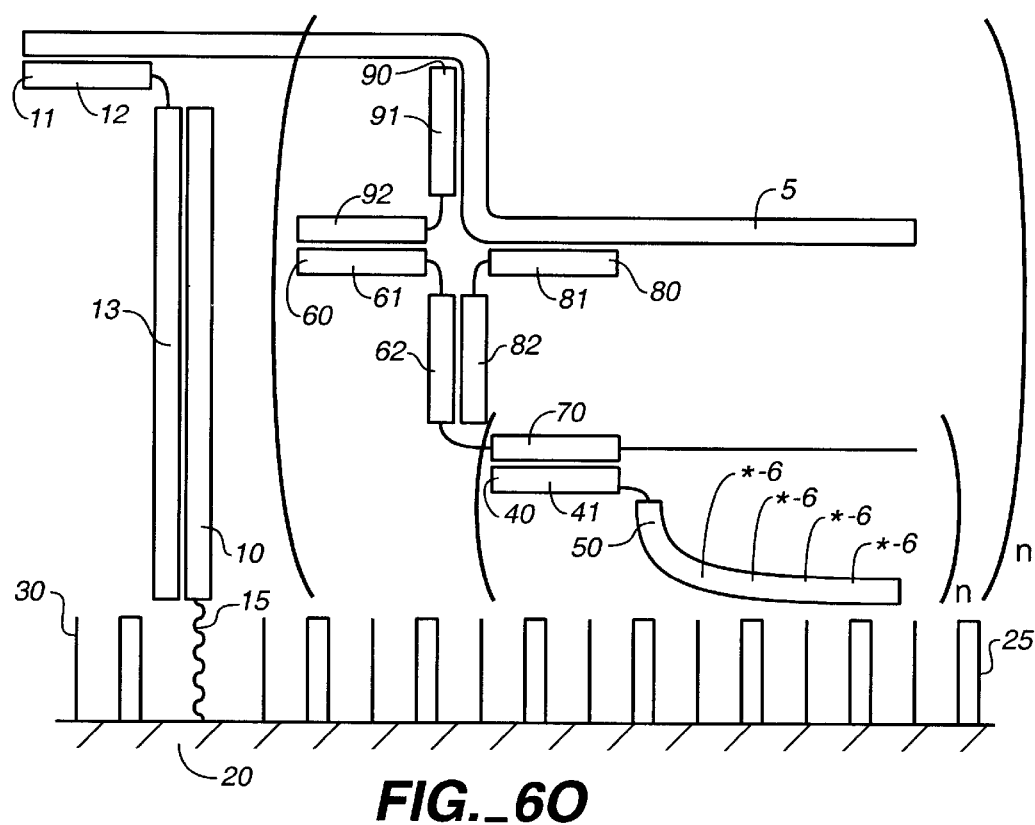
FIG._6O

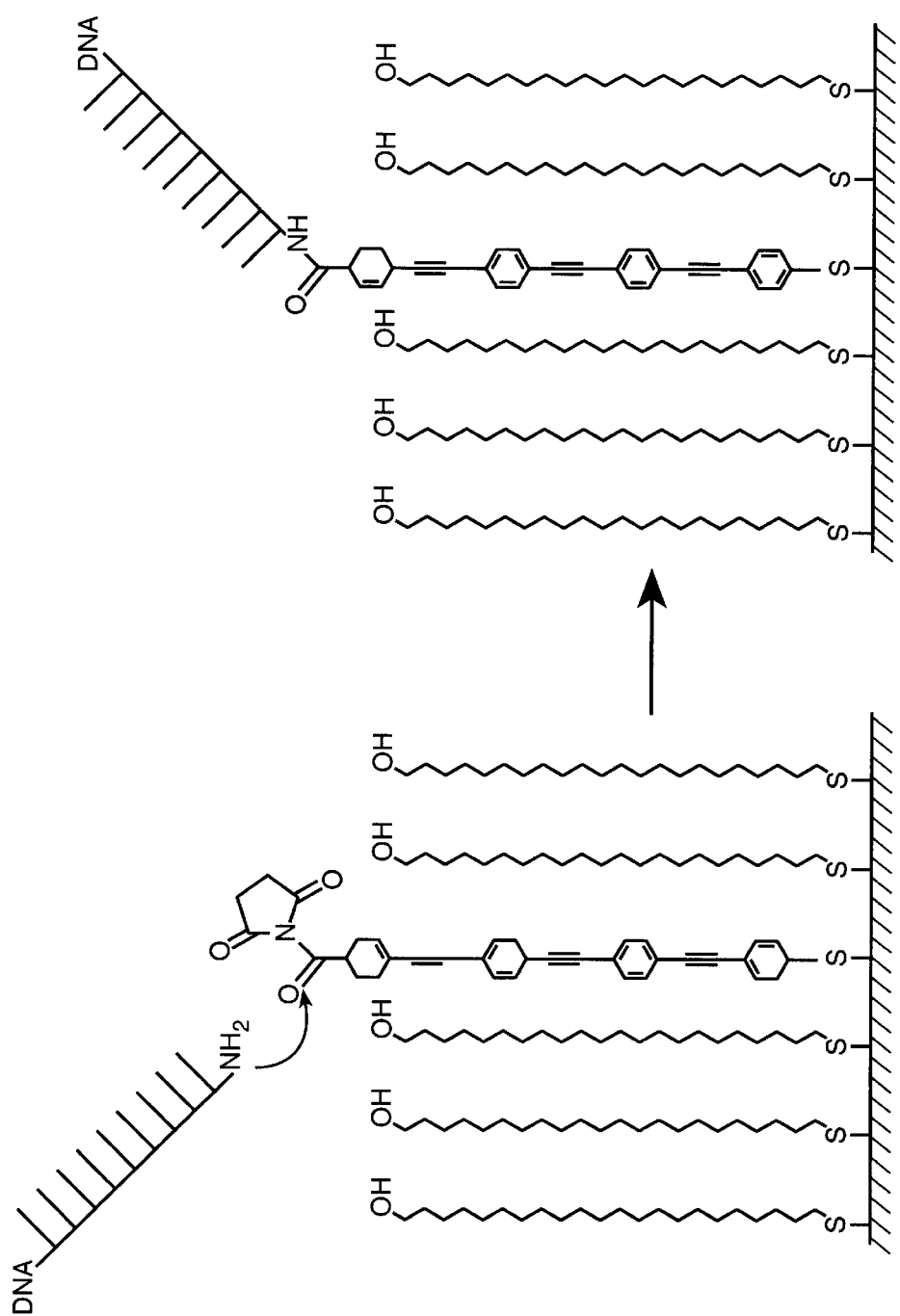
FIG._7

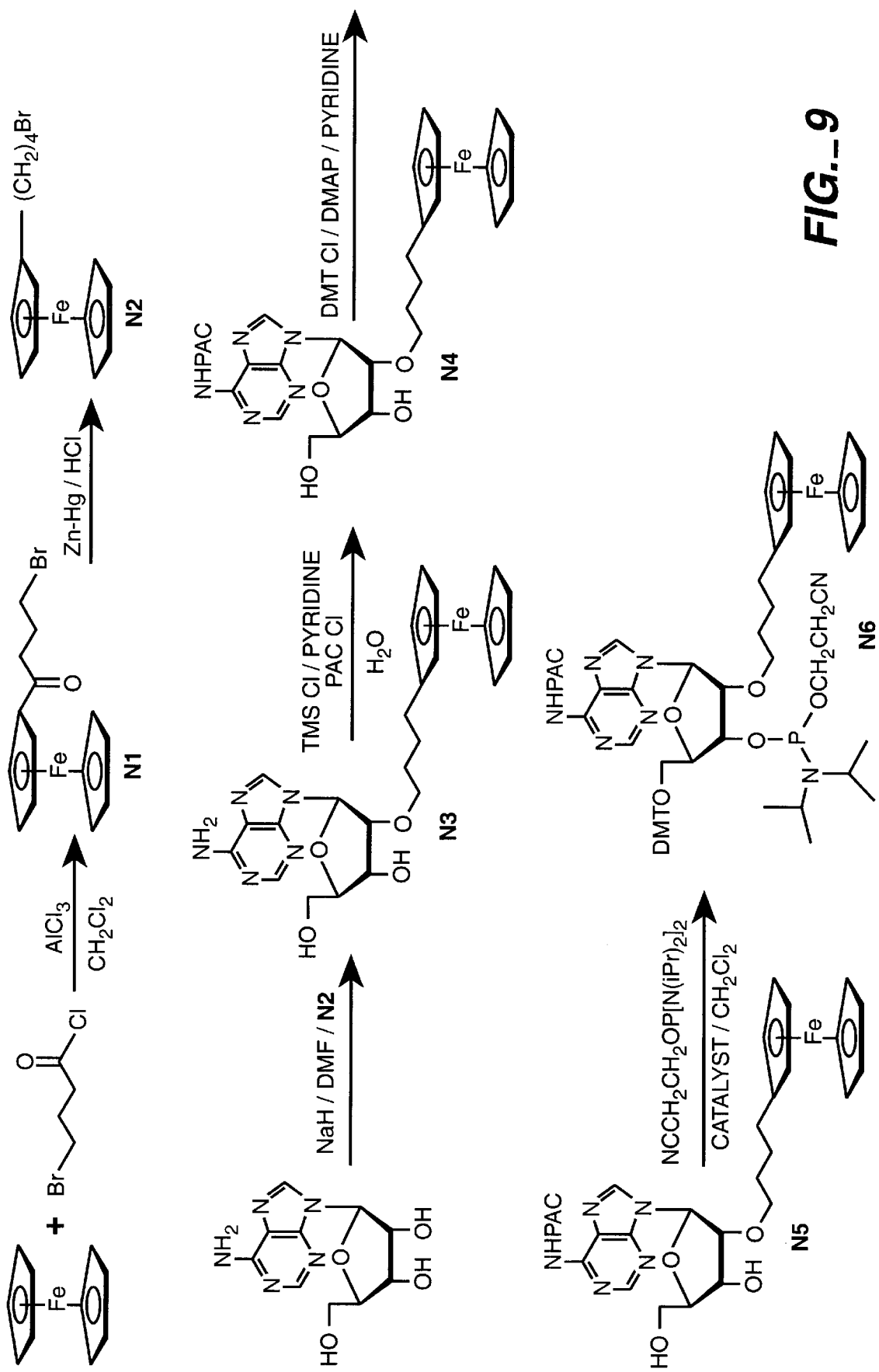
FIG._9

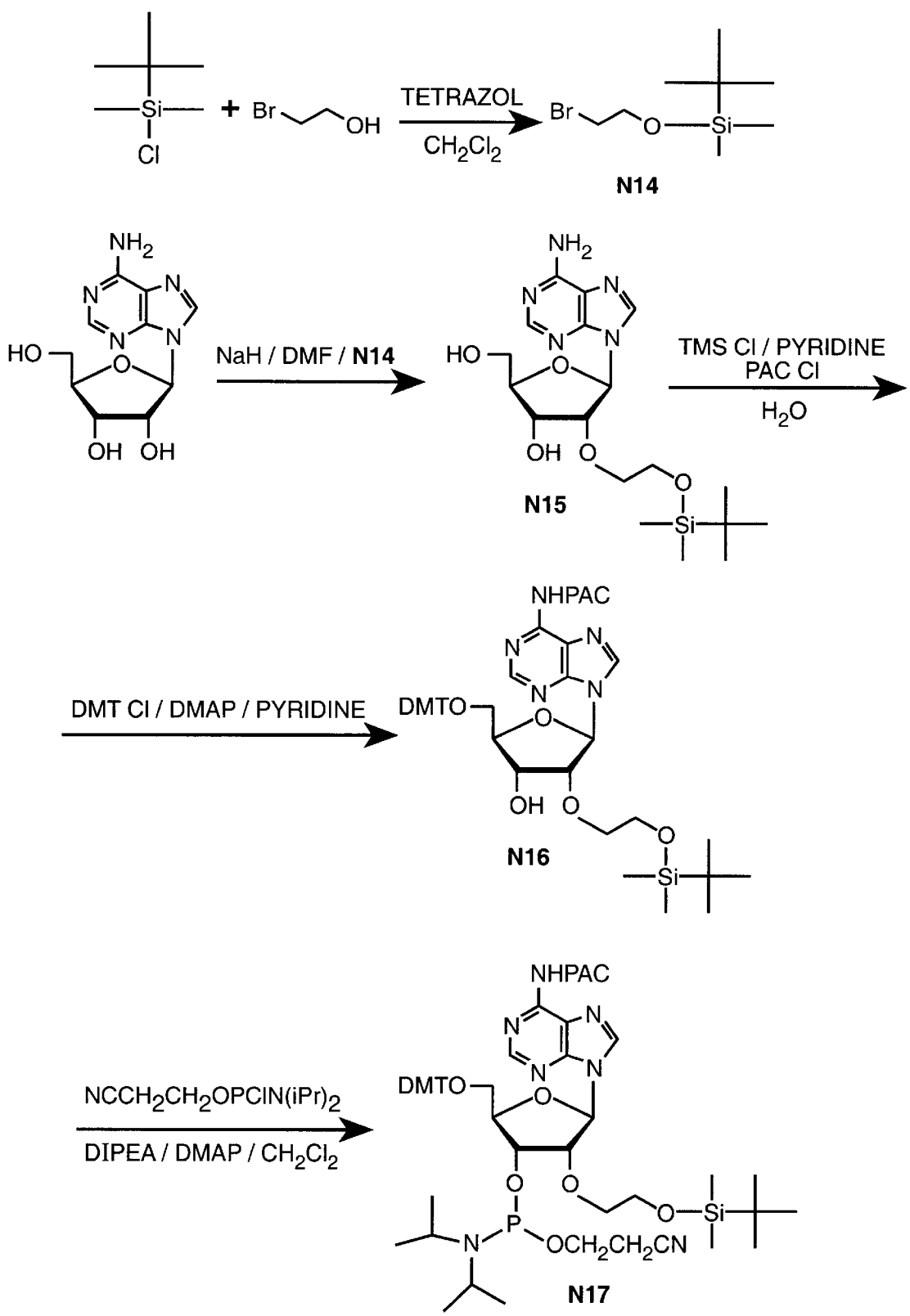
FIG._10

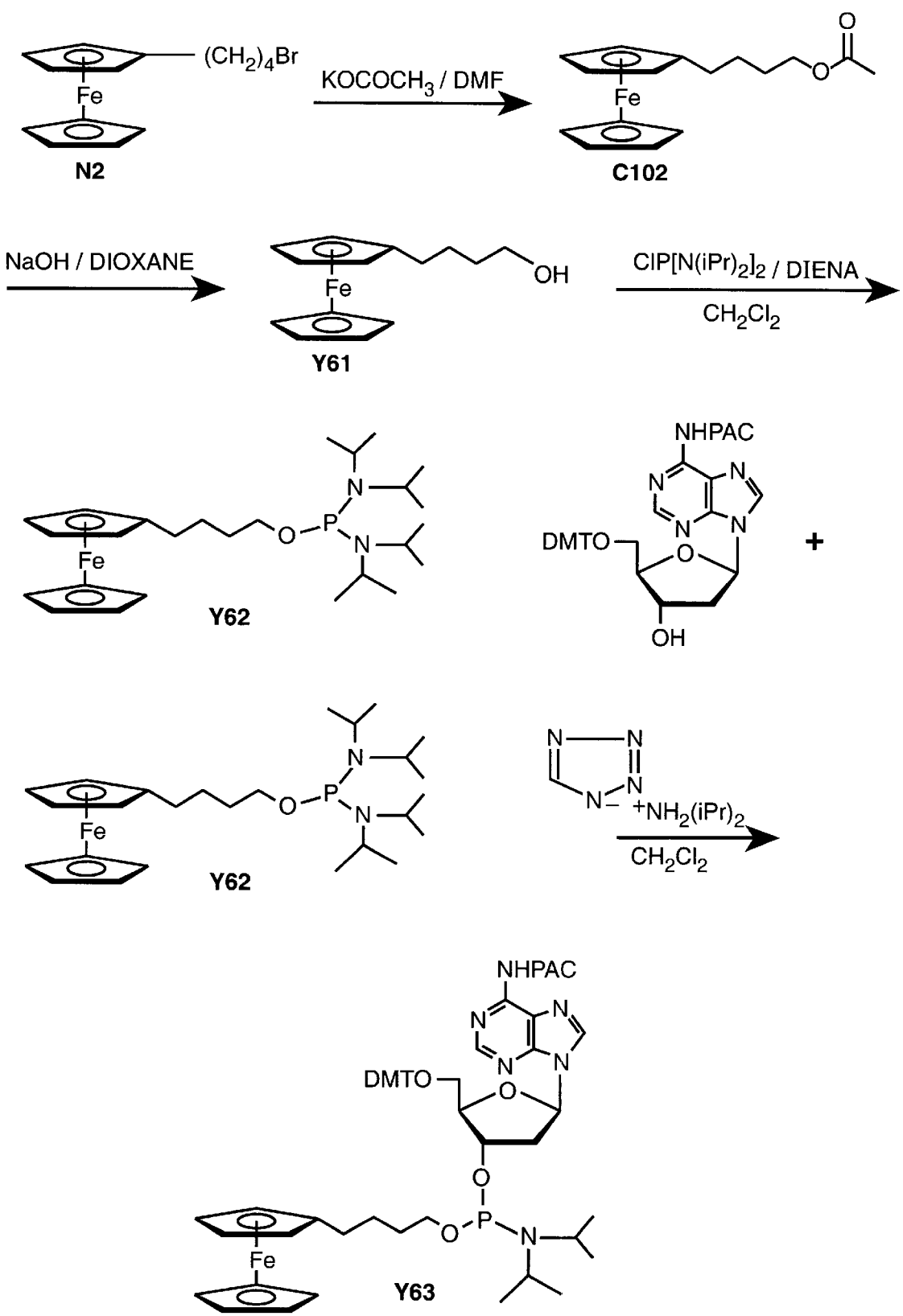
FIG._11

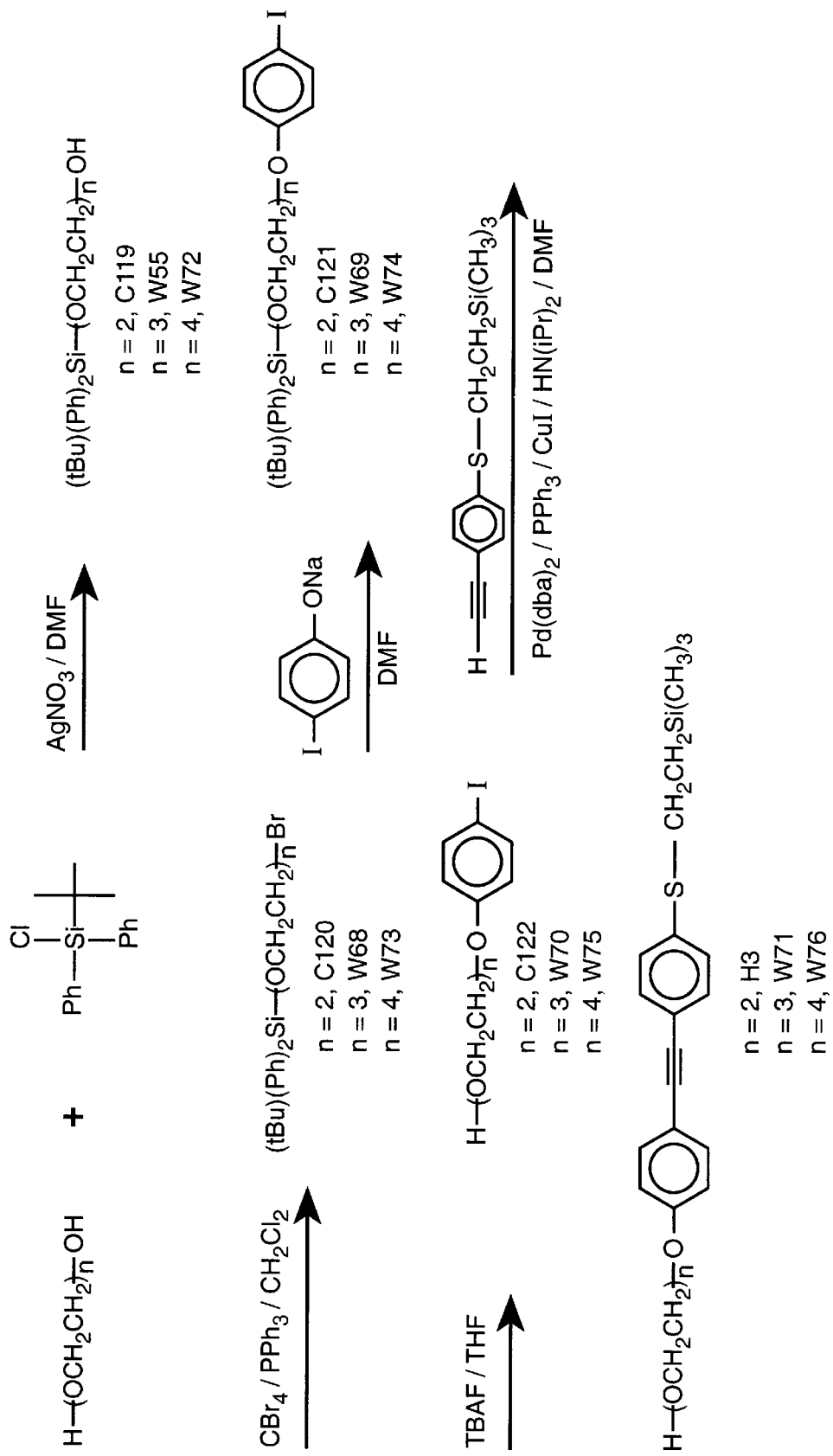
FIG._12

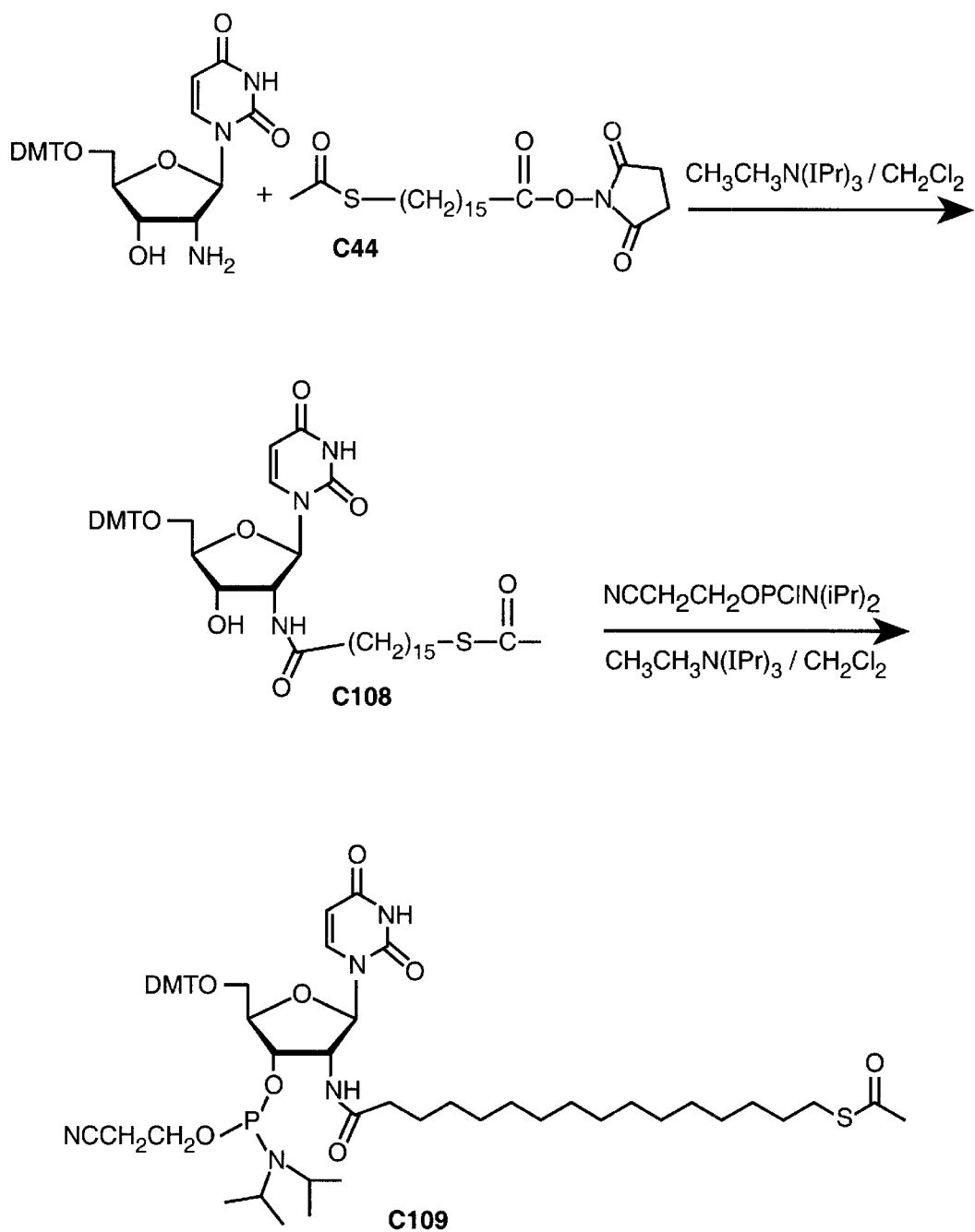
FIG._13

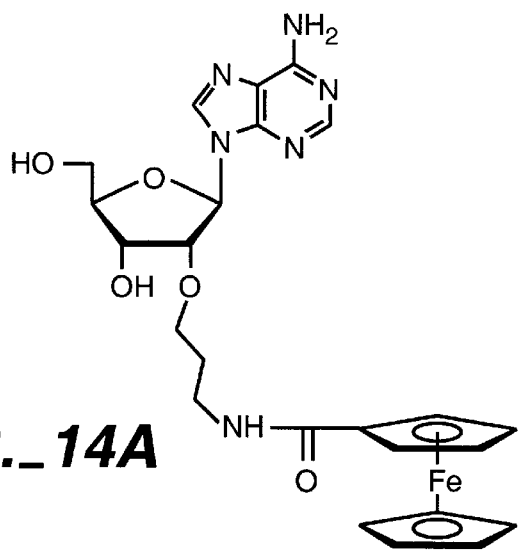
I
FIG._14A
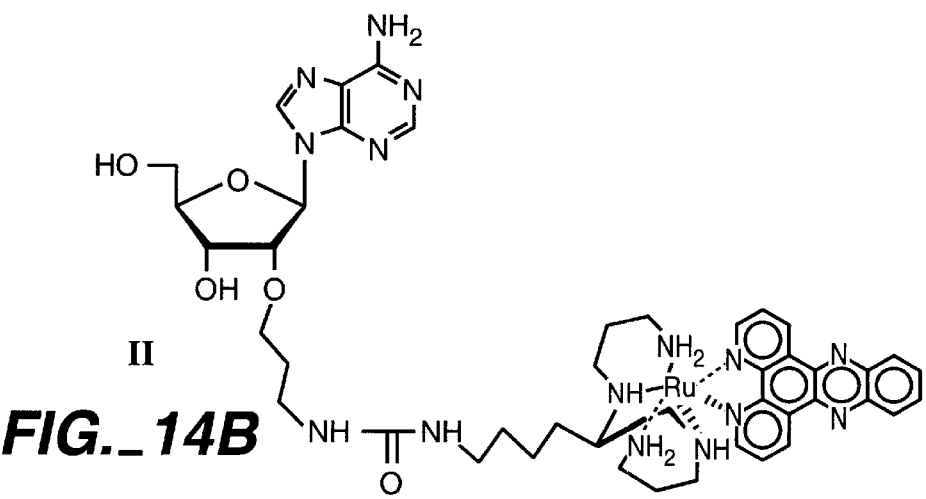
II
FIG._14B
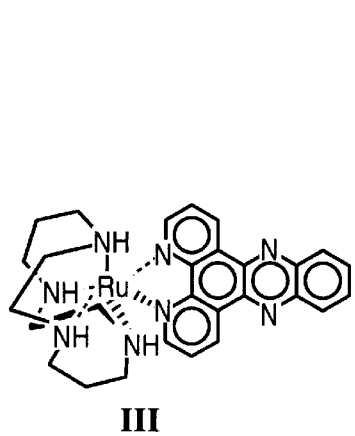
III
FIG._14C
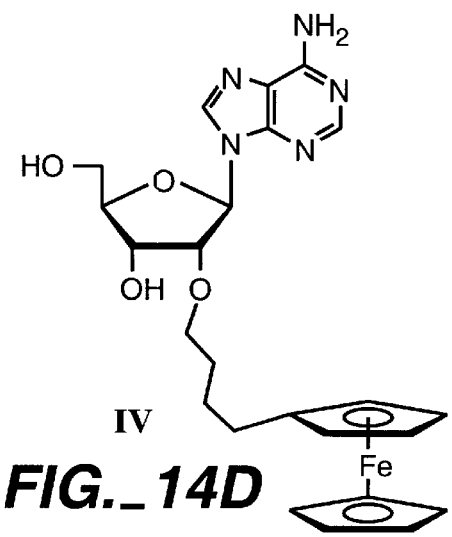
IV
FIG._14D

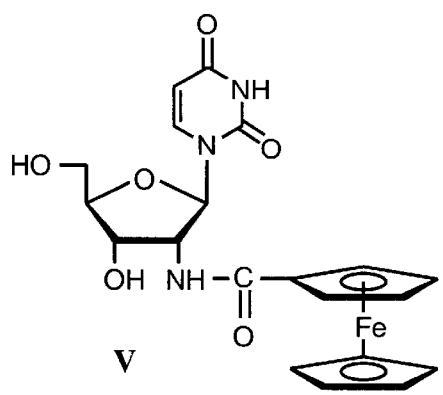
FIG._14E
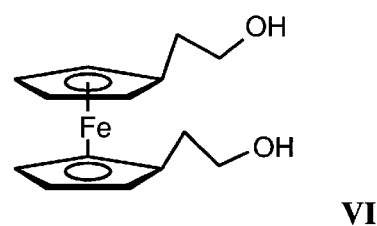
FIG._14F
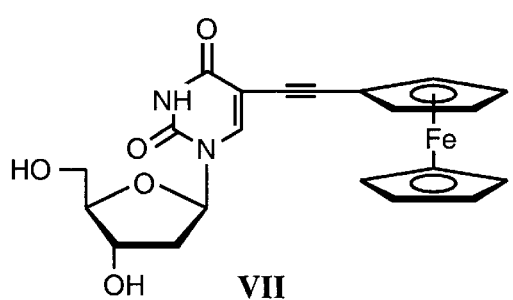
FIG._14G
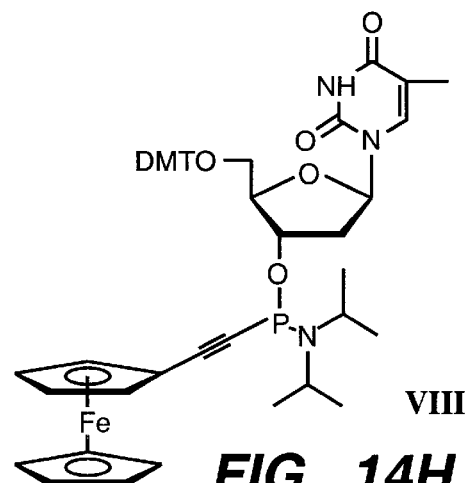
FIG._14H
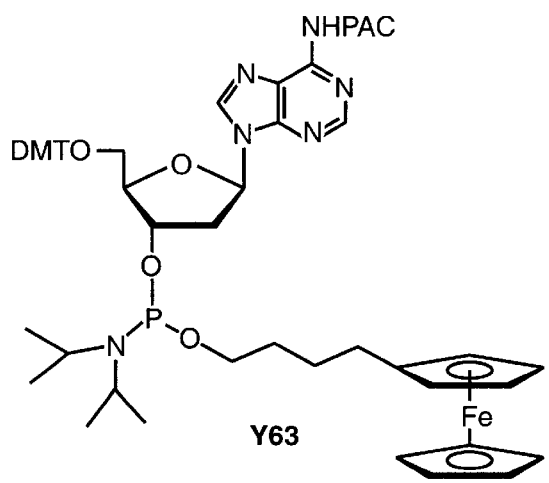
FIG._14I
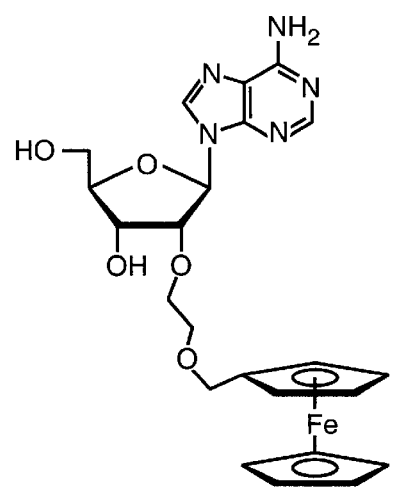
FIG._14J

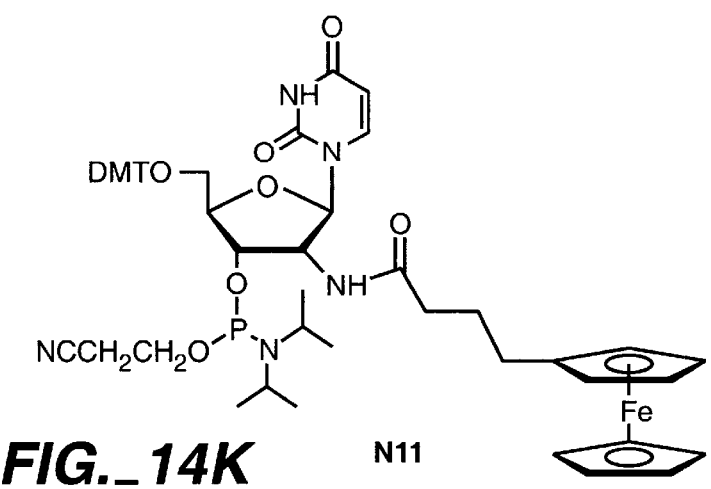
FIG._14K  N11
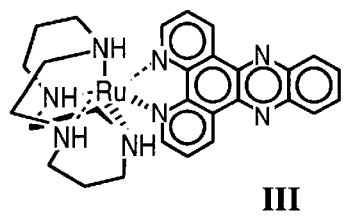
FIG._15C
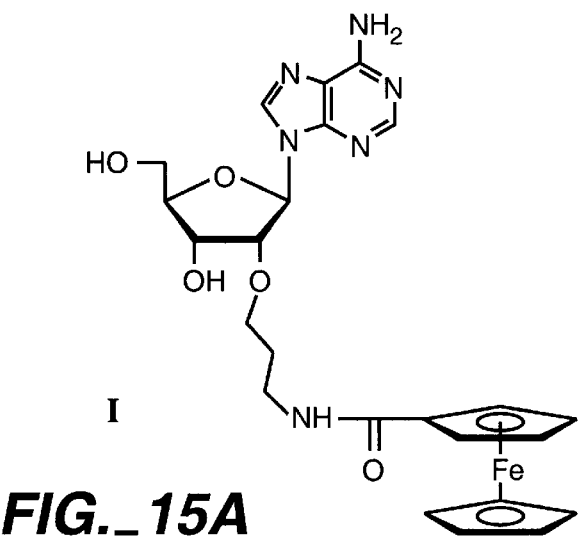
FIG._15A
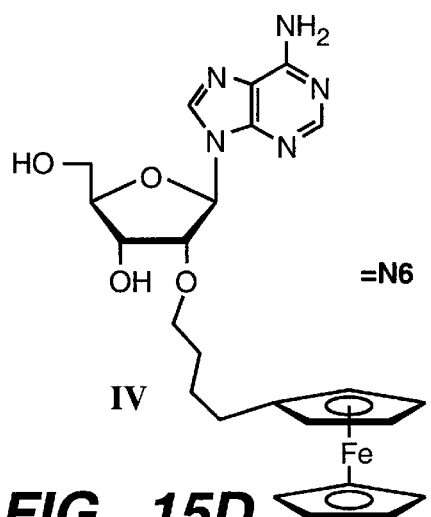
FIG._15D
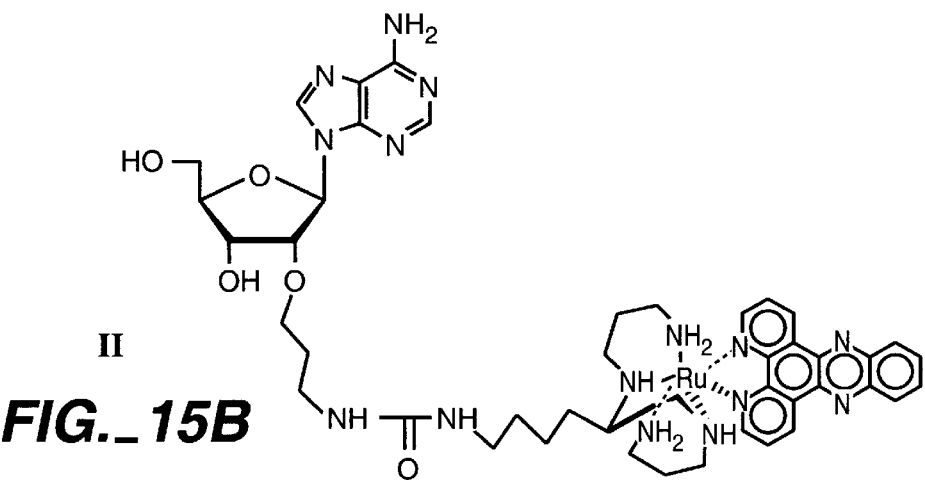
FIG._15B

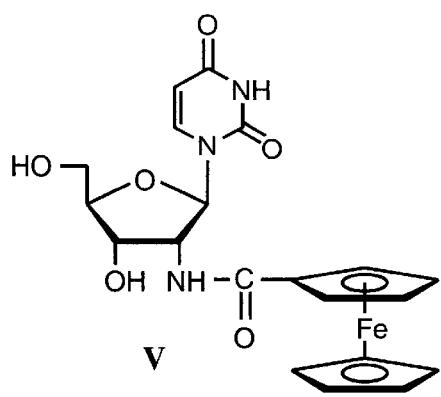
FIG._15E
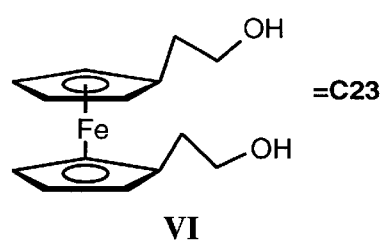
FIG._15F
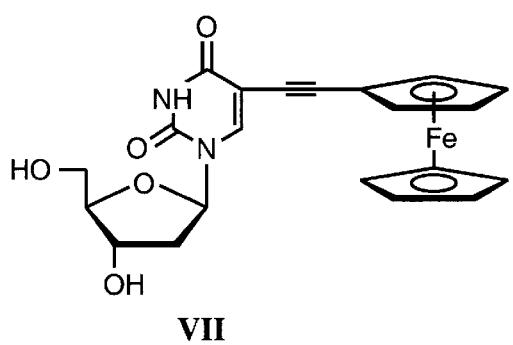
FIG._15G
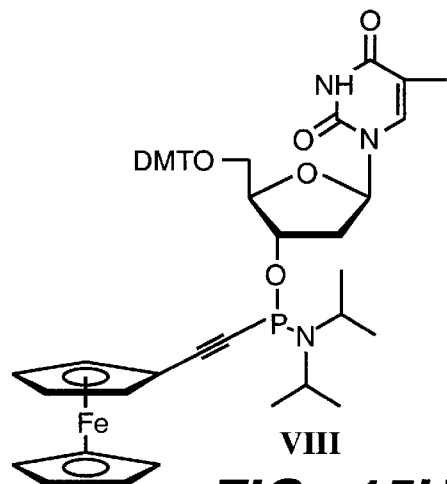
FIG._15H
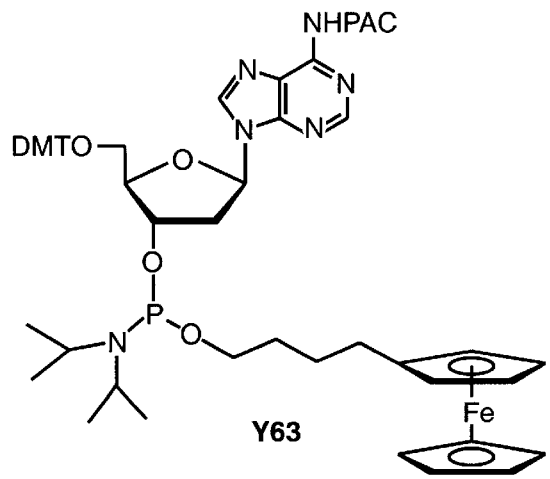
FIG._15I
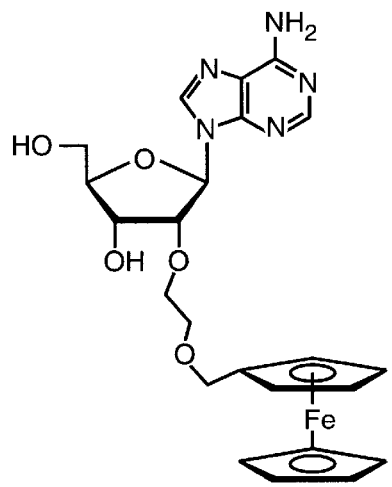
FIG._15J

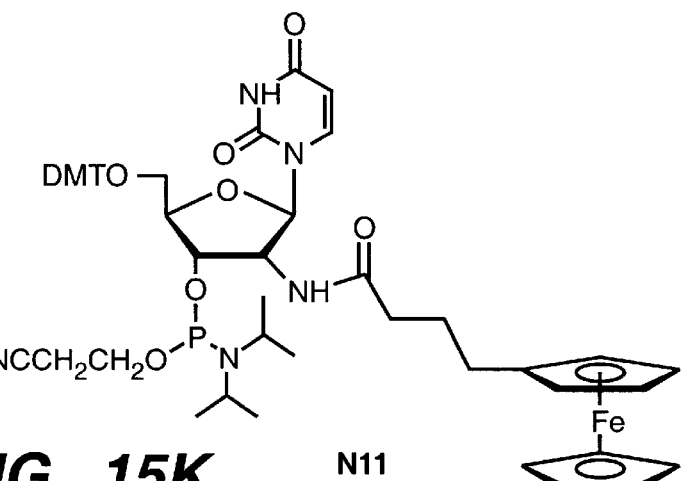
FIG._15K  N11
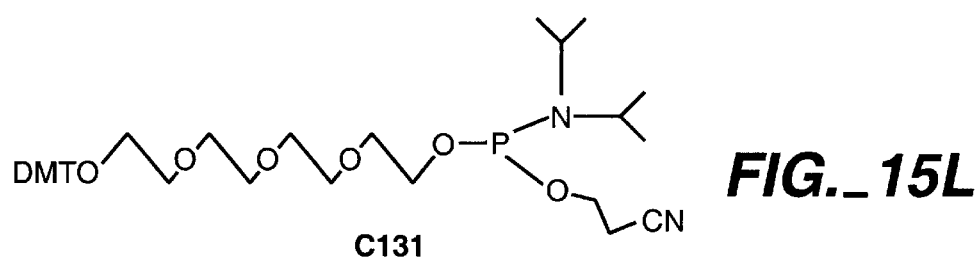
FIG._15L
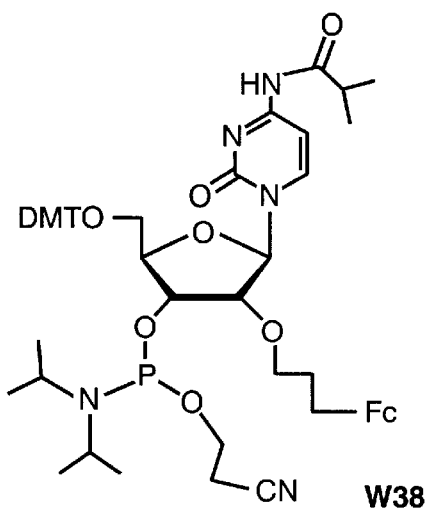
FIG._15M
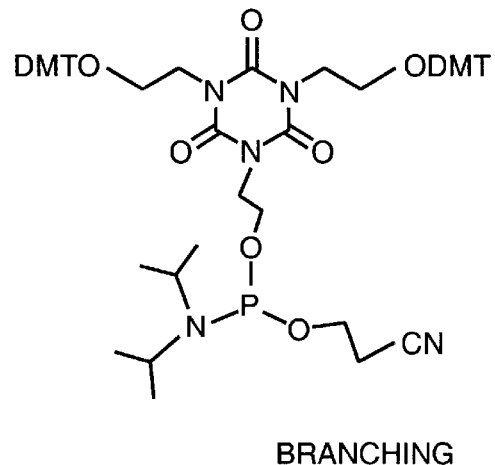
FIG._15N
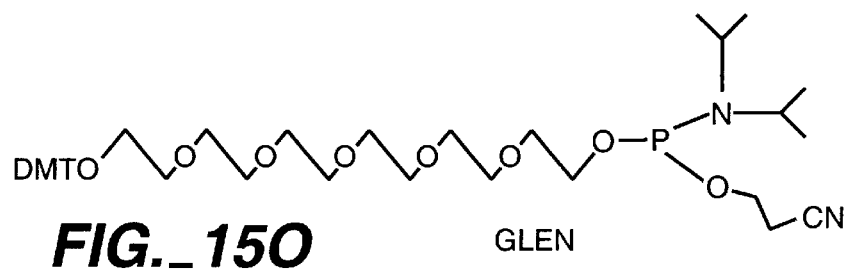
FIG._15O

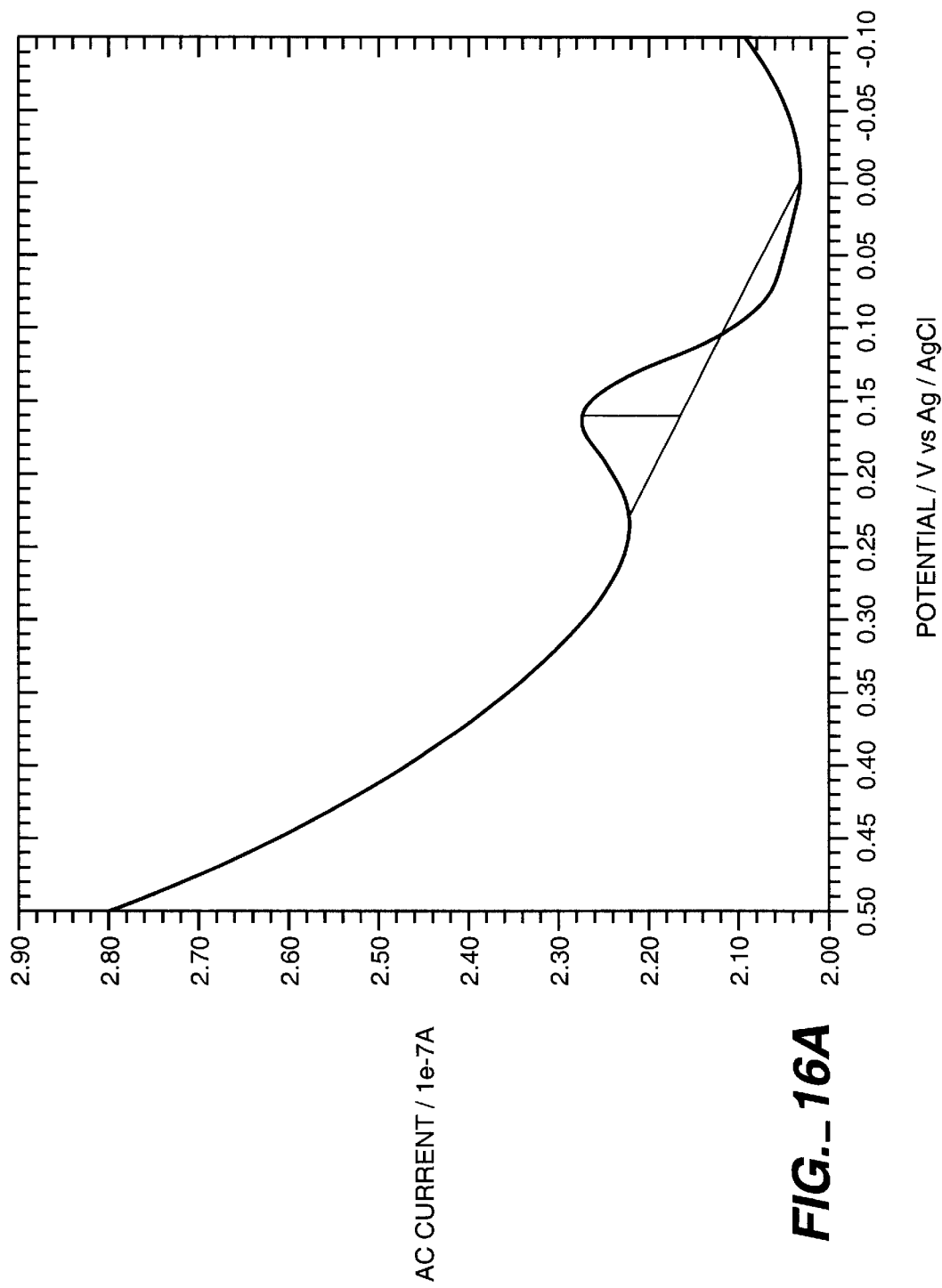
FIG._16A

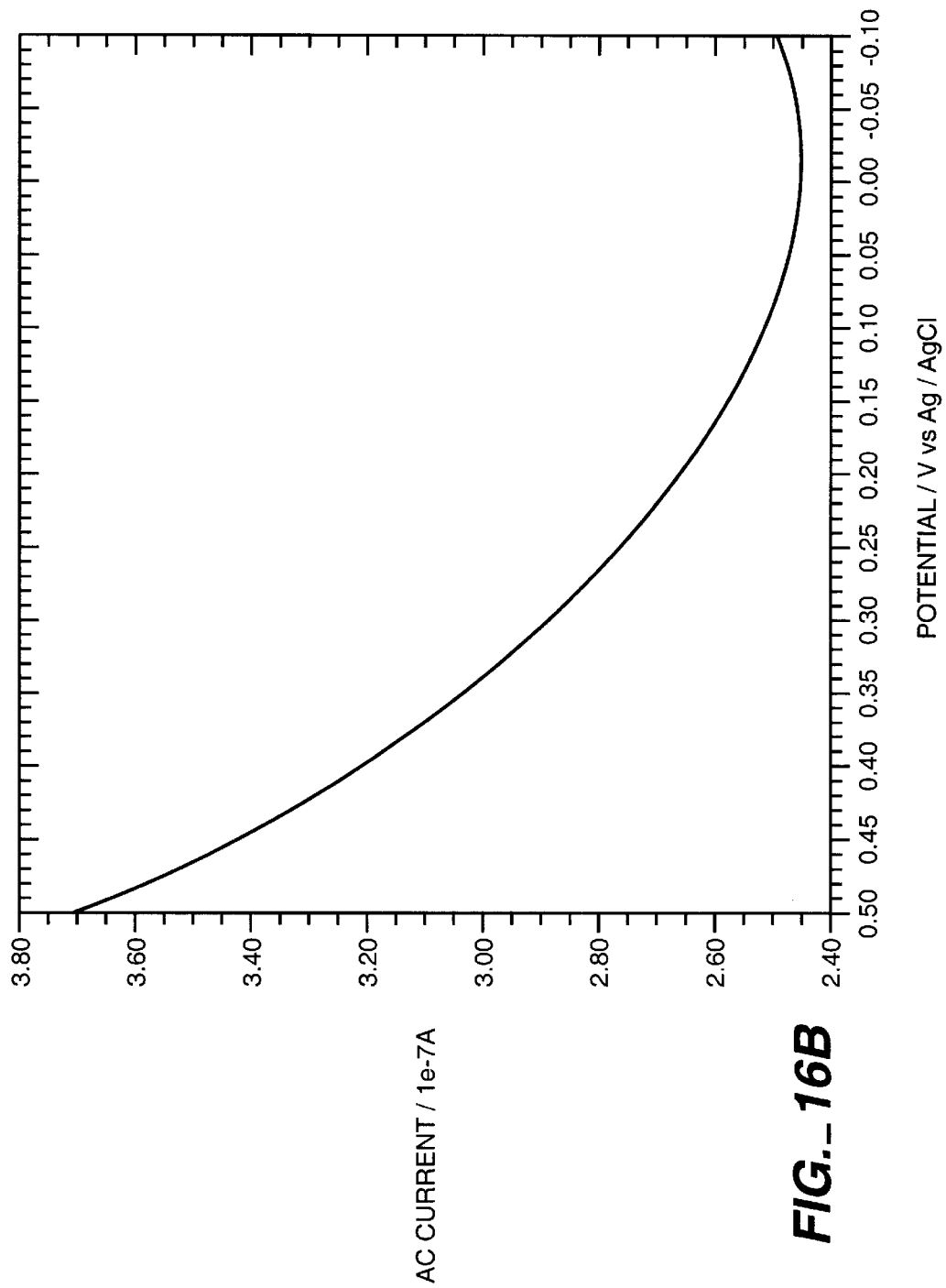
FIG._16B

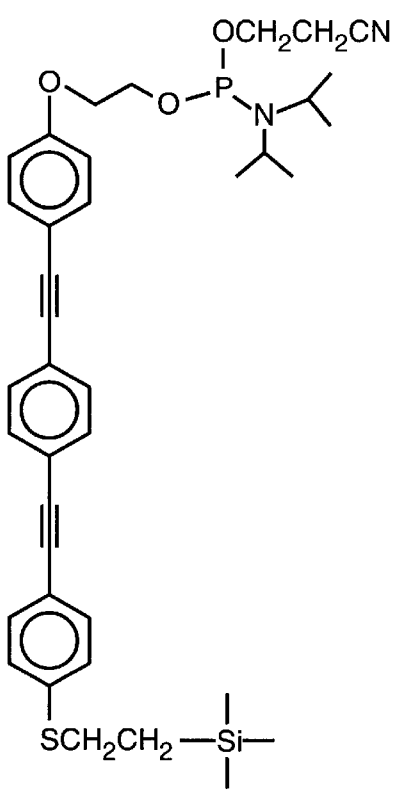 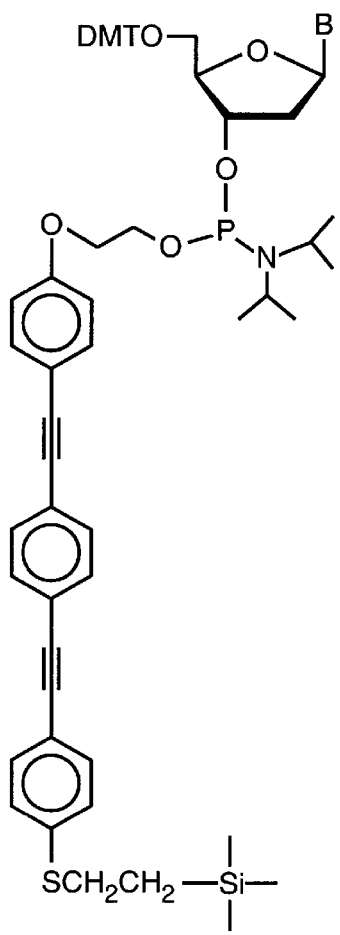
5' - ATTACHMENT
FIG._18A
ANY POSITION ATTACHMENT
FIG._18B

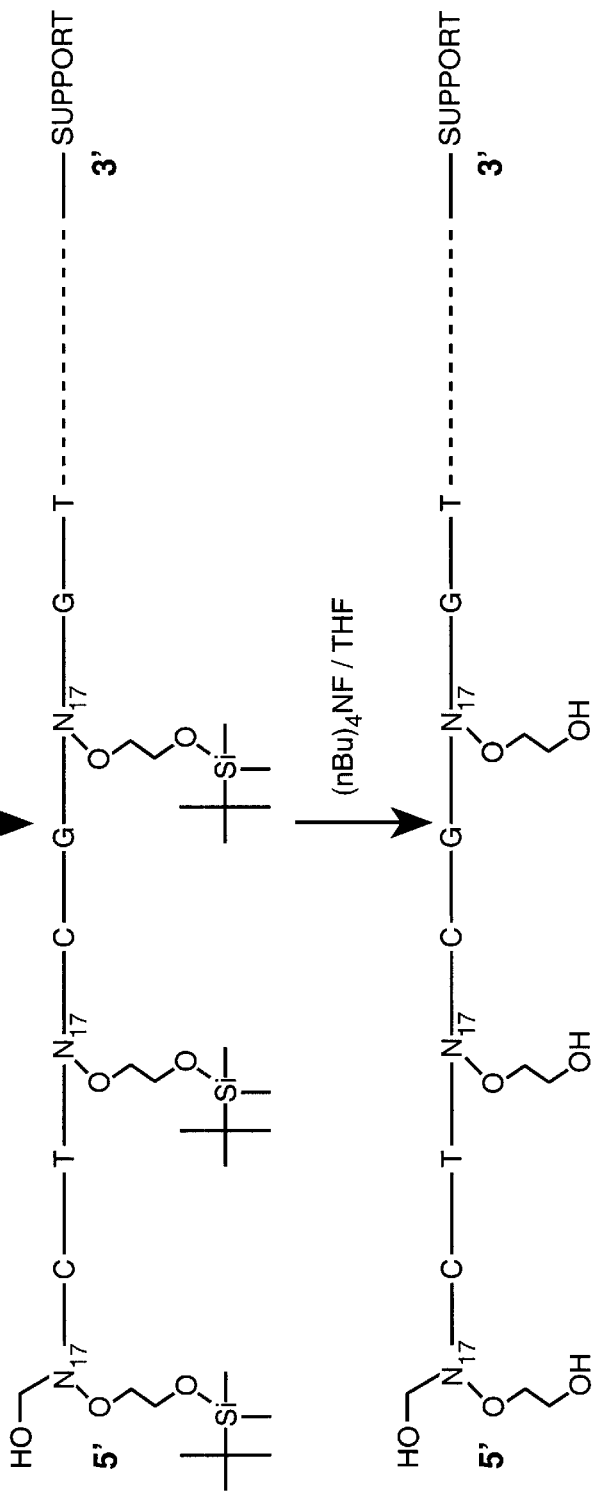
FIG._19A

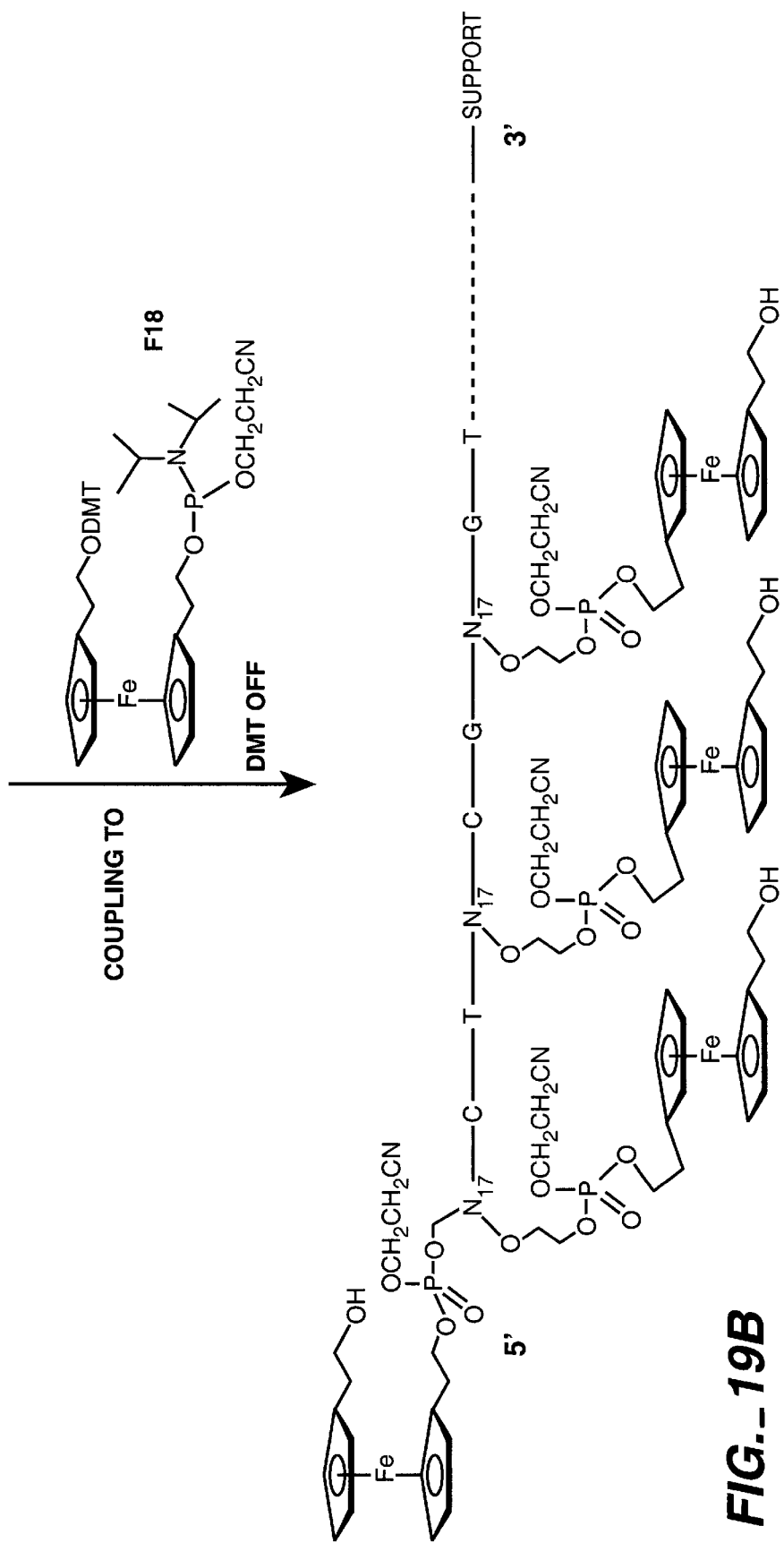
FIG._19B

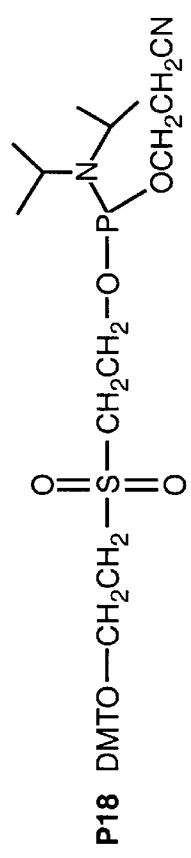
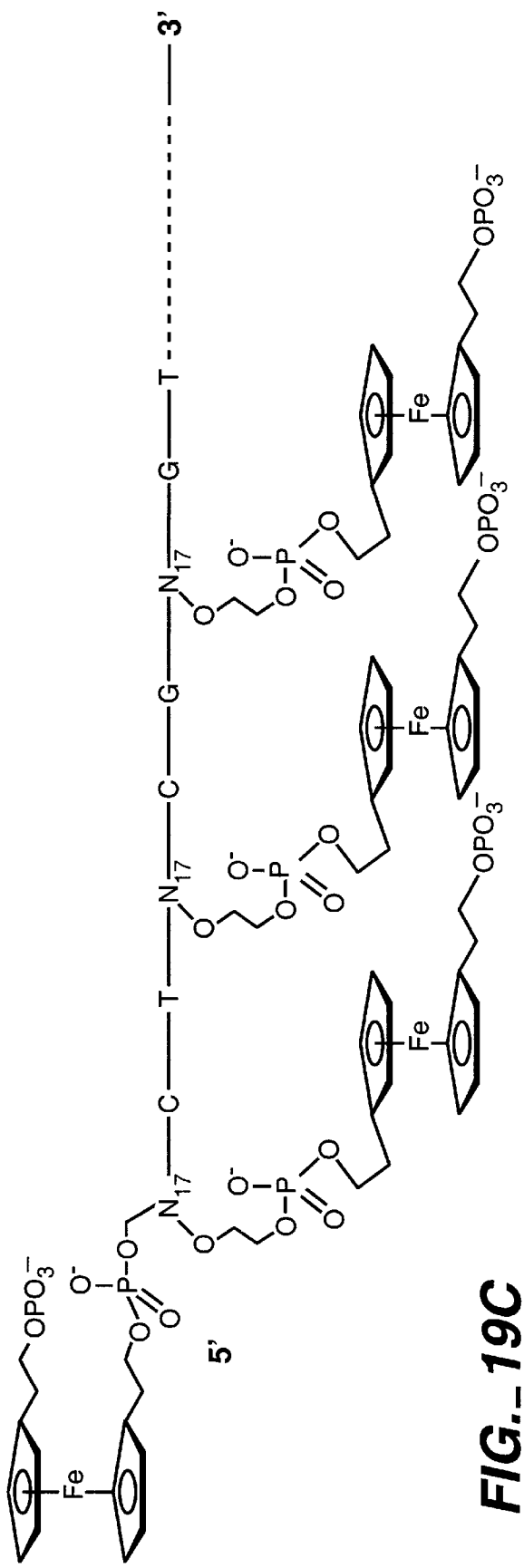
FIG._19C

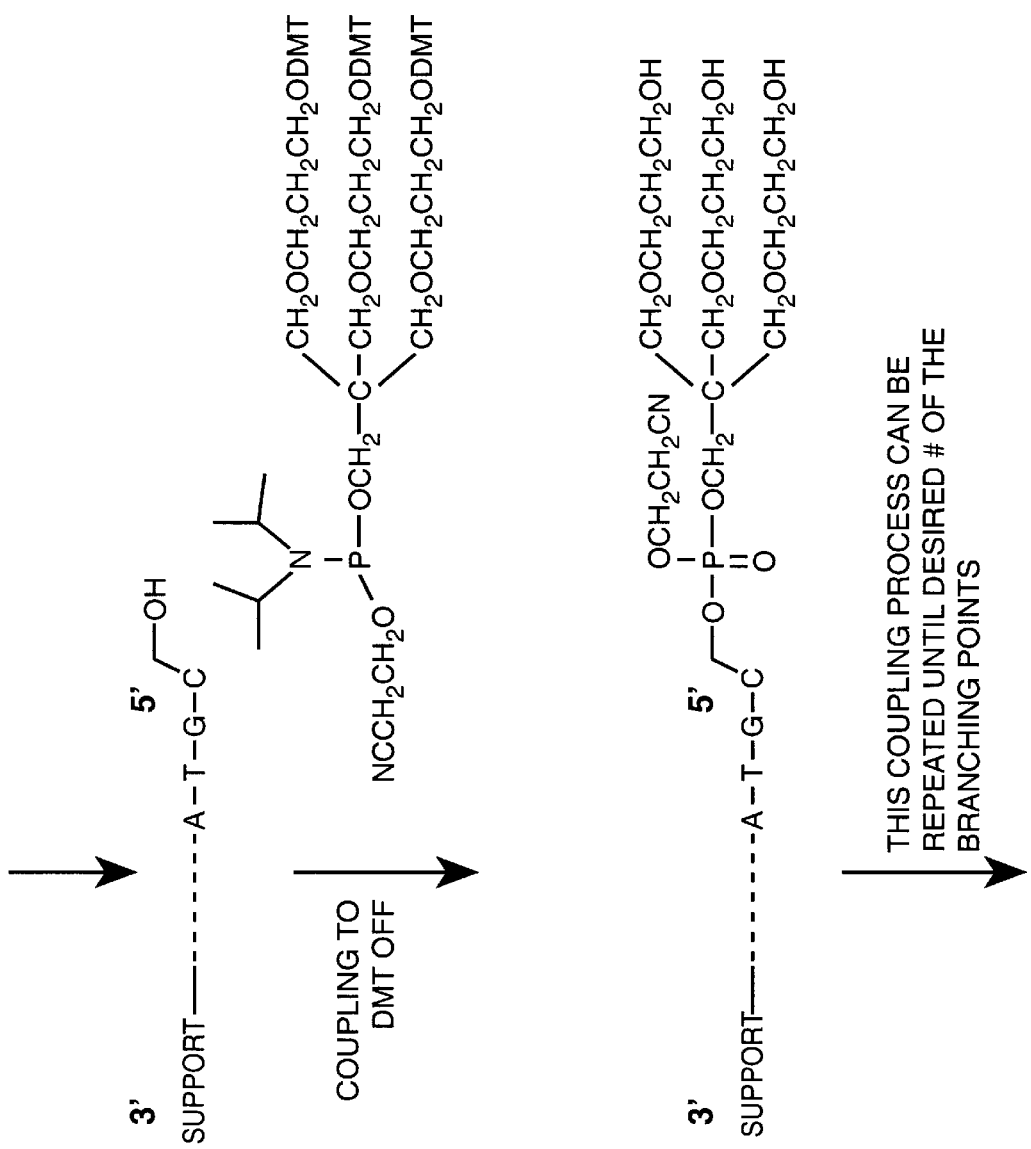
FIG._20
FIG._20A

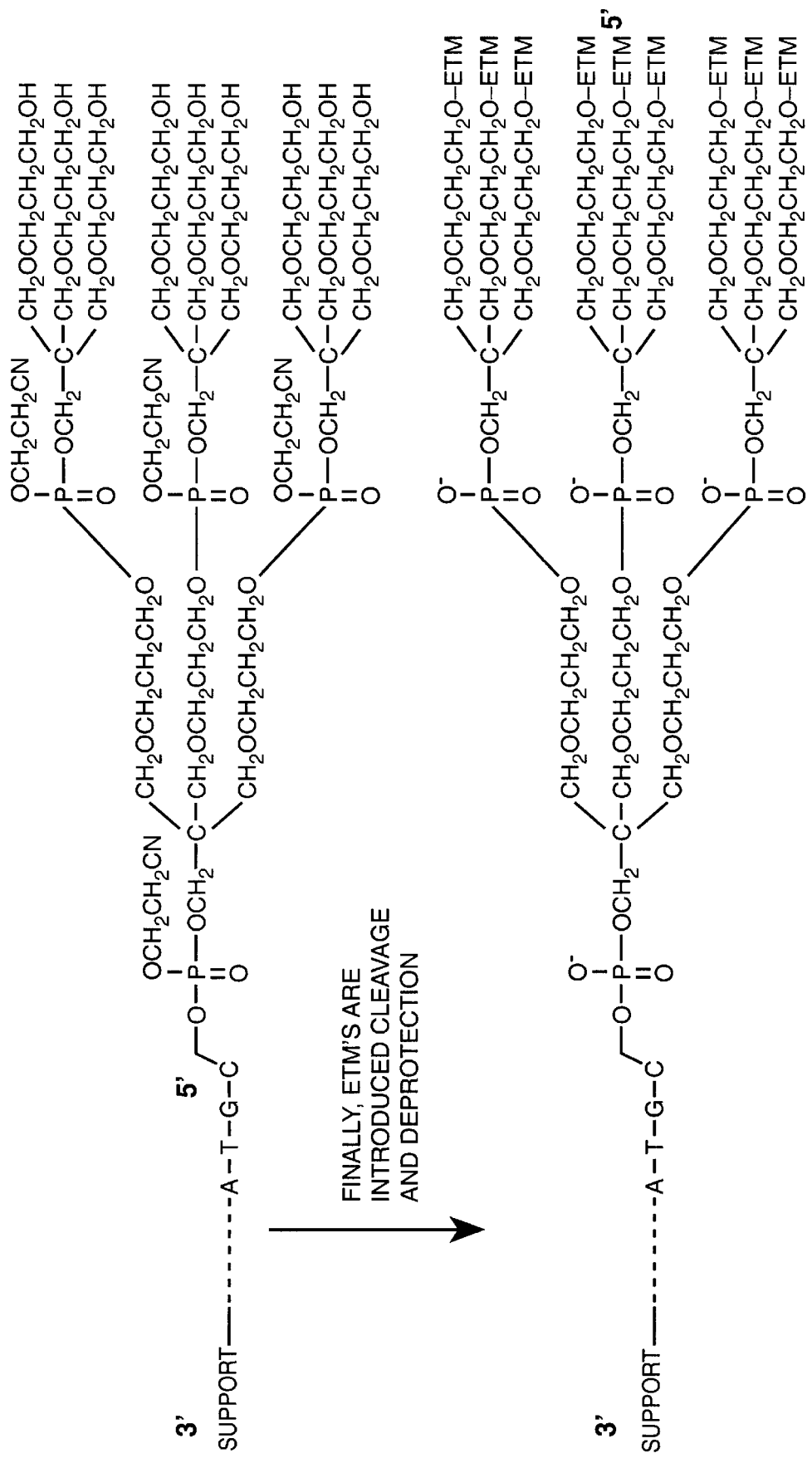
FIG._20B

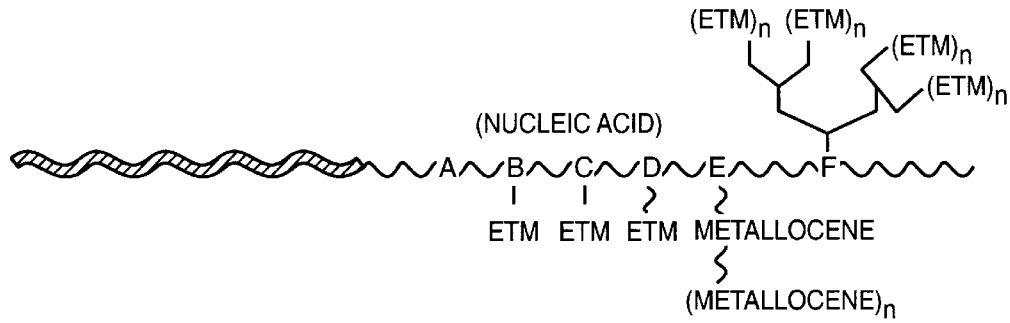
A = NUCLEOSIDE REPLACEMENT
B = ATTACHMENT TO A BASE
C = ATTACHMENT TO A RIBOSE
D = ATTACHMENT TO A PHOSPHATE
E = METALLOCENE POLYMER, ATTACHED TO A RIBOSE, PHOSPHATE, OR BASE
F = DENDRIMER STRUCTURE, ATTACHED VIA A RIBOSE, PHOSPHATE OR BASE
*FIG._21A*
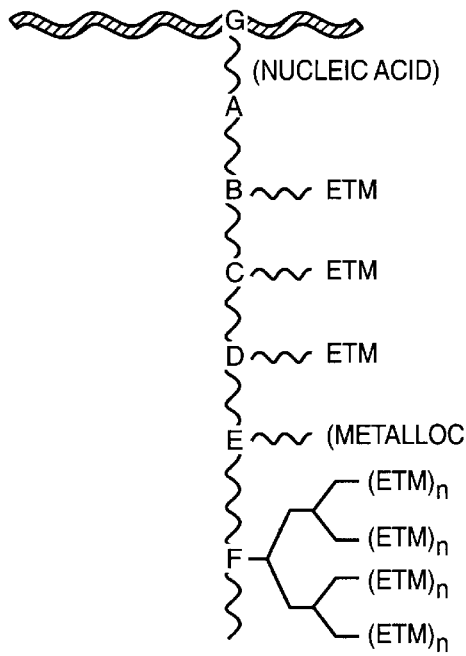
G = ATTACHMENT VIA A "BRANCHING STRUCTURE", THROUGH RIBOSE, PHOSPHATE OR BASE
*FIG._21B*

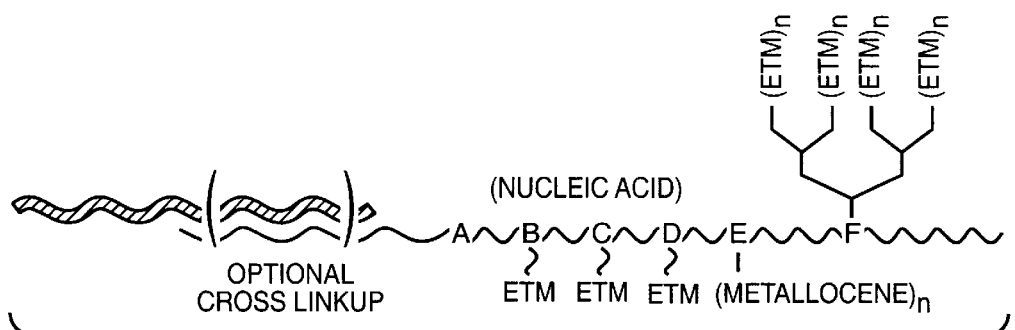
FIG._21C
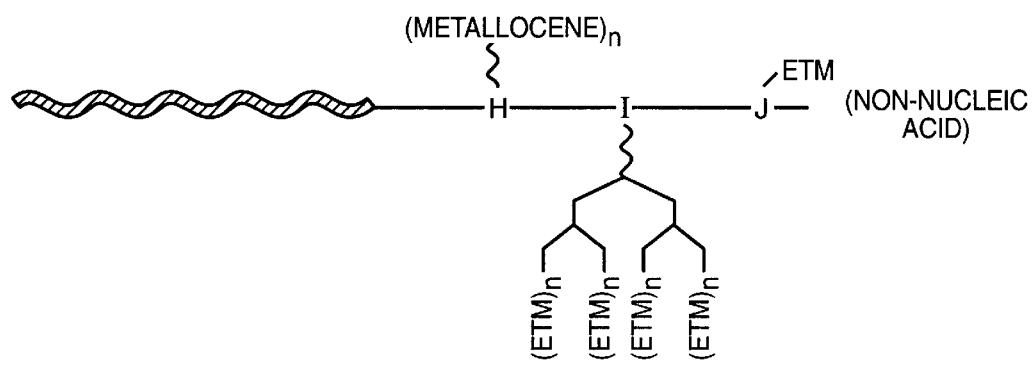
H = ATTACHMENT OF METALLOCENE POLYMERS
I = ATTACHMENT VIA DENDRIMER STRUCTURE
J = ATTACHMENT USING STANDARD LINKERS
FIG._21D
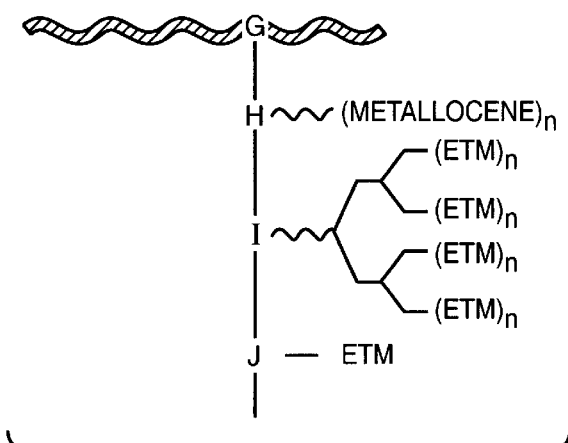
FIG._21E

D179
5' – A(C15)CCTGGTCTTGACATCCACGGAAGGCGTGGAAATACGTATTCGTGCCTA – 3'

D309 (Dendrimer)
5' – (W38)(Branching)(Branching)CATGGTTAACGTCAATTGCTGCGGTTATTAA – 3'

D295
5' – (N6)G(N6)CT(N6)C(N6)G(N6)C(N6)CCCATGGTTAGACTGAATTGCTGCGGTTATTAA – 3'

D297
5' – (N6)G(N6)CT(N6)C(N6)G(N6)C(N6)TATGCTCTTGATGGTGCTGTGGAAATCTACTGG – 3'

D298
5' – (N6)G(N6)CT(N6)C(N6)G(N6)C(N6)ATGGTGCTGTGGAAATCTACTGG – 3'

D296
5' – (N6)G(N6)CT(N6)C(N6)G(N6)C(N6)TGACTGAATTGCTGCGGTTATTAA – 3'

D112
5' – CTTCCGTGGATGTCAAGACCAGGAU – 4 unit wire (C11) – 3'

D94
5' – ACCATGGACACAGAU – 4 unit wire (C11) – 3'

D109
5' – CTGCGGTTATTAACU – 4 unit wire (C11) – 3'

2Tar
5' – TAG GCA CGA ATA CGT ATT TCC ACG ATA AAT ATA ATT AAT AAC CGC AGC AAT TGA CGT ATA AAG CTA TCC CAG TAG ATT TCC ACA GC – 3'

D349
5' – A(C15)C (C15)GT GTC CAT GGT AGT AGC TTA TCG TGG AAA TAC GTA TTC GTG CCT A – 3'

D382
5' – (Y63)G(Y63) CT(Y63) C(Y63)G (Y63)C(Y63) CCC ATG GTT AGA CTG AAT TGC TGC GGT TAT TAA – 3'

D383
5' – (Y63)G(Y63) CT(Y63) C(Y63)G (Y63)C(Y63) CCC ATG GTT AGA CTG GCT GTG GAA ATC TAC TGG – 3'

D468
5' – (N6)G(N6) CT(N6) C(N6)G (N6)C(N6) (glen)(glen)(glen) CTT TAC TCC CTT CCT CCC CGC TGA AAG TAC – 3'

D449
5' – CGG AGT TAG CCG GTG CTT CTT CTG CGG G(C131)(C131) (C131)(C131)(N6) G(N6)C T(N6)C (N6)G(N6) C(N6)T – 3'

D417
5' – CTT TAC TCC CTT CCT CCC CGC TGA AAG TAC TTT ACA ACC C – 3'

EU1
5' – ATC CTG GTC TTG ACA TCC ACG GAA GAT GTC CCT ACA GTC TCC ATC AGG CAG TTT CCC AGA CA – 3'

MT1
5' – TCT ACA TGC CGT ACA TAC GGA ACG TAC GGA GCA TCC TGG TCT TGA CAT CCA CGG AAG – 3'

D358
5' – (N6)G(N6) CT(N6) C(N6)G (N6)C(N6) CCG TAT GTA CGG CAT GTA GA – 3'

D334
5' – GCT ACT ACC ATG GAC ACA GAU – 4 unit wire (C11) – 3'

D335
5' – ACA GAC ATC AGA GTA ATC (N6)GC C(N6)G TC(N6) TGG (N6)T – 3'

LP280
5' – GAT TAC TCT GAT GTC TGT CCA TCT GTG TCC ATG GTA GTA GC – 3'

LN280
5' – GAT TAC TCT GAT GTC TGT CCT AGT ACG AGT CAG TCT CTC CA – 3'

NC112
5' – TCT ACA TGC CGT ACA TAC GGA ACG TAC GGA GCG ATT CGA CTG ACA GTC GTA ACC TCA – 3'

D336
5' – (N6)G(N6) CT(N6) C(N6)G (N6)C(N6) GCG ACA ACT GTA CCA TCT GTG TCC ATG GT – 3'

D405
5' – (C23)(C23)(C23) (C23)(C23)(C23) (C23)(C23)(C23) (C23)AT CTG TGT CCA TGG T – 3'

D429
5' – (N6)G(N6) CT(N6) C(N6)G (N6)C(N6) (C131)AT CTG TGT CCA TGG TAG TAG C – 3'

FIG._22B

SEQUENCE LISTING

<160> NUMBER OF SEQ ID NOS: 47

<210> SEQ ID NO 1
<211> LENGTH: 49
<212> TYPE: DNA
<213> ORGANISM: Artificial Sequence
<220> FEATURE:
<223> OTHER INFORMATION: Description of Artificial Sequence:  synthetic

<400> SEQUENCE: 1
acctggtctt gacatccacg gaaggcgtgg aaatacgtat tcgtgccta          49

<210> SEQ ID NO 2
<211> LENGTH: 31
<212> TYPE: DNA
<213> ORGANISM: Artificial Sequence
<220> FEATURE:
<223> OTHER INFORMATION: Description of Artificial Sequence:  synthetic

<400> SEQUENCE: 2
catggttaac gtcaattgct gcggttatta a                            31

<210> SEQ ID NO 3
<211> LENGTH: 39
<212> TYPE: DNA
<213> ORGANISM: Artificial Sequence
<220> FEATURE:
<223> OTHER INFORMATION: Description of Artificial Sequence:  synthetic

<400> SEQUENCE: 3
gctcgcccca tggttagact gaattgctgc ggttattaa                    39

<210> SEQ ID NO 4
<211> LENGTH: 39
<212> TYPE: DNA
<213> ORGANISM: Artificial Sequence
<220> FEATURE:
<223> OTHER INFORMATION: Description of Artificial Sequence:  synthetic

```
<400> SEQUENCE: 4
gctcgctatg ctcttgatgg tgctgtggaa atctactgg                    39

<210> SEQ ID NO 5
<211> LENGTH: 29
<212> TYPE: DNA
<213> ORGANISM: Artificial Sequence
<220> FEATURE:
<223> OTHER INFORMATION: Description of Artificial Sequence: synthetic

<400> SEQUENCE: 5
gctcgcatgg tgctgtggaa atctactgg                               29

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: synthetic

<400> SEQUENCE: 6
gctcgctgac tgaattgctg cggttattaa                              30

<210> SEQ ID NO 7
<211> LENGTH: 25
<212> TYPE: DNA
<213> ORGANISM: Artificial Sequence
<220> FEATURE:
<223> OTHER INFORMATION: Description of Combined DNA/RNA Molecule:
      synthetic
<220> FEATURE:
<223> OTHER INFORMATION: Description of Artificial Sequence: synthetic

<400> SEQUENCE: 7
cttccgtgga tgtcaagacc aggau                                   25

<210> SEQ ID NO 8
<211> LENGTH: 15
<212> TYPE: DNA
<213> ORGANISM: Artificial Sequence
<220> FEATURE:
<223> OTHER INFORMATION: Description of Combined DNA/RNA Molecule:
      synthetic
<220> FEATURE:
<223> OTHER INFORMATION: Description of Artificial Sequence: synthetic

<400> SEQUENCE: 8
accatggaca cagau                                              15

<210> SEQ ID NO 9
<211> LENGTH: 15
<212> TYPE: DNA
<213> ORGANISM: Artificial Sequence
<220> FEATURE:
<223> OTHER INFORMATION: Description of Combined DNA/RNA Molecule:
      synthetic
<220> FEATURE:
<223> OTHER INFORMATION: Description of Artificial Sequence: synthetic

<400> SEQUENCE: 9
ctgcggttat taacu                                              15

<210> SEQ ID NO 10
<211> LENGTH: 86
<212> TYPE: DNA
<213> ORGANISM: Artificial Sequence
```

-continued

<220> FEATURE:
<223> OTHER INFORMATION: Description of Artificial Sequence: synthetic

<400> SEQUENCE: 10
taggcacgaa tacgtatttc cacgataaat ataattaata accgcagcaa ttgacgtata        60
aagctatccc agtagatttc cacagc        86

<210> SEQ ID NO 11
<211> LENGTH: 47
<212> TYPE: DNA
<213> ORGANISM: Artificial Sequence
<220> FEATURE:
<223> OTHER INFORMATION: Description of Artificial Sequence: synthetic

<400> SEQUENCE: 11
acgtgtccat ggtagtagct tatcgtggaa atacgtattc gtgccta        47

<210> SEQ ID NO 12
<211> LENGTH: 39
<212> TYPE: DNA
<213> ORGANISM: Artificial Sequence
<220> FEATURE:
<223> OTHER INFORMATION: Description of Artificial Sequence: synthetic

<400> SEQUENCE: 12
gctcgcccca tggttagact gaattgctgc ggttattaa        39

<210> SEQ ID NO 13
<211> LENGTH: 39
<212> TYPE: DNA
<213> ORGANISM: Artificial Sequence
<220> FEATURE:
<223> OTHER INFORMATION: Description of Artificial Sequence: synthetic

<400> SEQUENCE: 13
gctcgcccca tggttagact ggctgtggaa atctactgg        39

<210> SEQ ID NO 14
<211> LENGTH: 36
<212> TYPE: DNA
<213> ORGANISM: Artificial Sequence
<220> FEATURE:
<223> OTHER INFORMATION: Description of Artificial Sequence: synthetic

<400> SEQUENCE: 14
gctcgccttt actcccttcc tccccgctga aagtac        36

<210> SEQ ID NO 15
<211> LENGTH: 35
<212> TYPE: DNA
<213> ORGANISM: Artificial Sequence
<220> FEATURE:
<223> OTHER INFORMATION: Description of Artificial Sequence: synthetic

<400> SEQUENCE: 15
cggagttagc cggtgcttct tctgcggggc tcgct        35

<210> SEQ ID NO 16
<211> LENGTH: 40
<212> TYPE: DNA
<213> ORGANISM: Artificial Sequence
<220> FEATURE:
<223> OTHER INFORMATION: Description of Artificial Sequence: synthetic

<400> SEQUENCE: 16
ctttactccc ttcctccccg ctgaaagtac tttacaaccc        40

<210> SEQ ID NO 17
<211> LENGTH: 62
<212> TYPE: DNA
<213> ORGANISM: Artificial Sequence
<220> FEATURE:
<223> OTHER INFORMATION: Description of Artificial Sequence: synthetic

<400> SEQUENCE: 17
atcctggtct tgacatccac ggaagatgtc cctacagtct ccatcaggca gtttcccaga        60
ca        62

<210> SEQ ID NO 18
<211> LENGTH: 57
<212> TYPE: DNA
<213> ORGANISM: Artificial Sequence
<220> FEATURE:
<223> OTHER INFORMATION: Description of Artificial Sequence: synthetic

<400> SEQUENCE: 18
tctacatgcc gtacatacgg aacgtacgga gcatcctggt cttgacatcc acggaag        57

<210> SEQ ID NO 19
<211> LENGTH: 26
<212> TYPE: DNA
<213> ORGANISM: Artificial Sequence
<220> FEATURE:
<223> OTHER INFORMATION: Description of Artificial Sequence: synthetic

<400> SEQUENCE: 19
gctcgcccgt atgtacggca tgtaga        26

<210> SEQ ID NO 20
<211> LENGTH: 21
<212> TYPE: DNA
<213> ORGANISM: Artificial Sequence
<220> FEATURE:
<223> OTHER INFORMATION: Description of Combined DNA/RNA Molecule:
      synthetic
<220> FEATURE:
<223> OTHER INFORMATION: Description of Artificial Sequence: synthetic

<400> SEQUENCE: 20
gctactacca tggacacaga u        21

<210> SEQ ID NO 21
<211> LENGTH: 28
<212> TYPE: DNA
<213> ORGANISM: Artificial Sequence
<220> FEATURE:
<223> OTHER INFORMATION: Description of Artificial Sequence: synthetic

<400> SEQUENCE: 21
acagacatca gagtaatcgc cgtctggt        28

<210> SEQ ID NO 22
<211> LENGTH: 41
<212> TYPE: DNA
<213> ORGANISM: Artificial Sequence
<220> FEATURE:
<223> OTHER INFORMATION: Description of Artificial Sequence: synthetic

<400> SEQUENCE: 22
gattactctg atgtctgtcc atctgtgtcc atggtagtag c                41

<210> SEQ ID NO 23
<211> LENGTH: 41
<212> TYPE: DNA
<213> ORGANISM: Artificial Sequence
<220> FEATURE:
<223> OTHER INFORMATION: Description of Artificial Sequence: synthetic

<400> SEQUENCE: 23
gattactctg atgtctgtcc tagtacgagt cagtctctcc a                41

<210> SEQ ID NO 24
<211> LENGTH: 57
<212> TYPE: DNA
<213> ORGANISM: Artificial Sequence
<220> FEATURE:
<223> OTHER INFORMATION: Description of Artificial Sequence: synthetic

<400> SEQUENCE: 24
tctacatgcc gtacatacgg aacgtacgga gcgattcgac tgacagtcgt aacctca       57

<210> SEQ ID NO 25
<211> LENGTH: 35
<212> TYPE: DNA
<213> ORGANISM: Artificial Sequence
<220> FEATURE:
<223> OTHER INFORMATION: Description of Artificial Sequence: synthetic

<400> SEQUENCE: 25
gctcgcgcga caactgtacc atctgtgtcc atggt                       35

<210> SEQ ID NO 26
<211> LENGTH: 15
<212> TYPE: DNA
<213> ORGANISM: Artificial Sequence
<220> FEATURE:
<223> OTHER INFORMATION: Description of Artificial Sequence: synthetic

<400> SEQUENCE: 26
atctgtgtcc atggt                                             15

<210> SEQ ID NO 27
<211> LENGTH: 27
<212> TYPE: DNA
<213> ORGANISM: Artificial Sequence
<220> FEATURE:
<223> OTHER INFORMATION: Description of Artificial Sequence: synthetic

<400> SEQUENCE: 27
gctcgcatct gtgtccatgg tagtagc                                27

<210> SEQ ID NO 28
<211> LENGTH: 13
<212> TYPE: DNA
<213> ORGANISM: Artificial Sequence
<220> FEATURE:
<223> OTHER INFORMATION: Description of Artificial Sequence: synthetic

<400> SEQUENCE: 28
acgagtccat ggt                                               13

<210> SEQ ID NO 29
<211> LENGTH: 13
<212> TYPE: DNA
<213> ORGANISM: Artificial Sequence
<220> FEATURE:
<223> OTHER INFORMATION: Description of Artificial Sequence: synthetic

<400> SEQUENCE: 29
agcctagctg gtg                                                        13

<210> SEQ ID NO 30
<211> LENGTH: 13
<212> TYPE: DNA
<213> ORGANISM: Artificial Sequence
<220> FEATURE:
<223> OTHER INFORMATION: Description of Artificial Sequence: synthetic

<400> SEQUENCE: 30
acgagtccat ggt                                                        13

<210> SEQ ID NO 31
<211> LENGTH: 13
<212> TYPE: DNA
<213> ORGANISM: Artificial Sequence
<220> FEATURE:
<223> OTHER INFORMATION: Description of Artificial Sequence: synthetic

<400> SEQUENCE: 31
agcctagctg gtg                                                        13

<210> SEQ ID NO 32
<211> LENGTH: 15
<212> TYPE: DNA
<213> ORGANISM: Artificial Sequence
<220> FEATURE:
<223> OTHER INFORMATION: Description of Artificial Sequence: synthetic

<400> SEQUENCE: 32
aacagagtcc atggt                                                      15

<210> SEQ ID NO 33
<211> LENGTH: 15
<212> TYPE: DNA
<213> ORGANISM: Artificial Sequence
<220> FEATURE:
<223> OTHER INFORMATION: Description of Artificial Sequence: synthetic

<400> SEQUENCE: 33
atgtcctagc tggtg                                                      15

<210> SEQ ID NO 34
<211> LENGTH: 13
<212> TYPE: DNA
<213> ORGANISM: Artificial Sequence
<220> FEATURE:
<223> OTHER INFORMATION: Description of Artificial Sequence: synthetic

<400> SEQUENCE: 34
acgagtccat ggt                                                        13

<210> SEQ ID NO 35
<211> LENGTH: 13
<212> TYPE: DNA
<213> ORGANISM: Artificial Sequence
<220> FEATURE:

<223> OTHER INFORMATION: Description of Artificial Sequence: synthetic

<400> SEQUENCE: 35
agcctagctg gtg                                                        13

<210> SEQ ID NO 36
<211> LENGTH: 13
<212> TYPE: DNA
<213> ORGANISM: Artificial Sequence
<220> FEATURE:
<223> OTHER INFORMATION: Description of Artificial Sequence: synthetic

<400> SEQUENCE: 36
acgagtccat ggt                                                        13

<210> SEQ ID NO 37
<211> LENGTH: 13
<212> TYPE: DNA
<213> ORGANISM: Artificial Sequence
<220> FEATURE:
<223> OTHER INFORMATION: Description of Artificial Sequence: synthetic

<400> SEQUENCE: 37
agcctagctg gtg                                                        13

<210> SEQ ID NO 38
<211> LENGTH: 14
<212> TYPE: DNA
<213> ORGANISM: Artificial Sequence
<220> FEATURE:
<223> OTHER INFORMATION: Description of Artificial Sequence: synthetic

<400> SEQUENCE: 38
acagagtcca tggt                                                       14

<210> SEQ ID NO 39
<211> LENGTH: 14
<212> TYPE: DNA
<213> ORGANISM: Artificial Sequence
<220> FEATURE:
<223> OTHER INFORMATION: Description of Artificial Sequence: synthetic

<400> SEQUENCE: 39
agtcctagct ggtg                                                       14

<210> SEQ ID NO 40
<211> LENGTH: 13
<212> TYPE: DNA
<213> ORGANISM: Artificial Sequence
<220> FEATURE:
<223> OTHER INFORMATION: Description of Artificial Sequence: synthetic

<400> SEQUENCE: 40
aagagtccat ggt                                                        13

<210> SEQ ID NO 41
<211> LENGTH: 13
<212> TYPE: DNA
<213> ORGANISM: Artificial Sequence
<220> FEATURE:
<223> OTHER INFORMATION: Description of Artificial Sequence: synthetic

<400> SEQUENCE: 41
atcctagctg gtg                                                        13

```
<210> SEQ ID NO 42
<211> LENGTH: 13
<212> TYPE: DNA
<213> ORGANISM: Artificial Sequence
<220> FEATURE:
<223> OTHER INFORMATION: Description of Artificial Sequence:  synthetic

<400> SEQUENCE: 42
acgagtccat ggt                                                           13

<210> SEQ ID NO 43
<211> LENGTH: 13
<212> TYPE: DNA
<213> ORGANISM: Artificial Sequence
<220> FEATURE:
<223> OTHER INFORMATION: Description of Artificial Sequence:  synthetic

<400> SEQUENCE: 43
agcctagctg gtg                                                           13

<210> SEQ ID NO 44
<211> LENGTH: 13
<212> TYPE: DNA
<213> ORGANISM: Artificial Sequence
<220> FEATURE:
<223> OTHER INFORMATION: Description of Artificial Sequence:  synthetic

<400> SEQUENCE: 44
acgagtccat ggt                                                           13

<210> SEQ ID NO 45
<211> LENGTH: 13
<212> TYPE: DNA
<213> ORGANISM: Artificial Sequence
<220> FEATURE:
<223> OTHER INFORMATION: Description of Artificial Sequence:  synthetic

<400> SEQUENCE: 45
agcctagctg gtg                                                           13

<210> SEQ ID NO 46
<211> LENGTH: 15
<212> TYPE: DNA
<213> ORGANISM: Artificial Sequence
<220> FEATURE:
<223> OTHER INFORMATION: Description of Combined DNA/RNA Molecule:
      synthetic
<220> FEATURE:
<223> OTHER INFORMATION: Description of Artificial Sequence:  synthetic

<400> SEQUENCE: 46
accatggact ctgtu                                                         15

<210> SEQ ID NO 47
<211> LENGTH: 15
<212> TYPE: DNA
<213> ORGANISM: Artificial Sequence
<220> FEATURE:
<223> OTHER INFORMATION: Description of Combined DNA/RNA Molecule:
      synthetic
<220> FEATURE:
<223> OTHER INFORMATION: Description of Artificial Sequence:  synthetic

<400> SEQUENCE: 47
accatggact cagau                                                         15
```

ELECTRONIC METHODS FOR THE DETECTION OF ANALYTES UTILIZING MONOLAYERS

This is a continuing application of Serial No. 60/084,652 filed May 6, 1998, Ser. No. 60/084,509 filed May 6, 1998, and of Ser. No. 09/135,183 filed Aug. 17, 1998.

FIELD OF THE INVENTION

The present invention relates to the use of self-assembled monolayers with mixtures of conductive oligomers and insulators to detect target analytes.

BACKGROUND OF THE INVENTION

There are a number of assays and sensors for the detection of the presence and/or concentration of specific substances in fluids and gases. Many of these rely on specific ligand/antiligand reactions as the mechanism of detection. That is, pairs of substances (i.e. the binding pairs or ligand/antiligands) are known to bind to each other, while binding little or not at all to other substances. This has been the focus of a number of techniques that utilize these binding pairs for the detection of the complexes. These generally are done by labeling one component of the complex in some way, so as to make the entire complex detectable, using, for example, radioisotopes, fluorescent and other optically active molecules, enzymes, etc.

Other assays rely on electronic signals for detection, Of particular interest are biosensors. At least two types of biosensors are known; enzyme-based or metabolic biosensors and binding or bioaffinity sensors. See for example U.S. Pat. Nos. 4,713,347; 5,192,507; 4,920,047; 3,873,267; and references disclosed therein. While some of these known sensors use alternating current (AC) techniques, these techniques are generally limited to the detection of differences in bulk (or dielectric) impedance.

The use of self-assembled monolayers (SAMs) on surfaces for binding and detection of biological molecules has recently been explored. See for example WO98/20162; PCT US98/12430; PCT US98/12082; PCT US99/01705; and U.S. Pat. No. 5,620,850; and references cited therein.

Accordingly, it is an object of the invention to provide novel methods and compositions for the electronic detection of target analytes using self-assembled monolayers.

SUMMARY OF THE INVENTION

In accordance with the objects outlined above, the present invention provides compositions comprising electrodes comprising a monolayer comprising conductive oligomers, and a capture binding ligand. The composition further comprises a recruitment linker that comprises at least one covalently attached electron transfer moiety, and a solution binding ligand that will bind to a target analyte.

In a further embodiment, the invention provides methods of detecting a target analyte in a test sample comprising attaching said target analyte to an electrode comprising a monolayer of conductive oligomers via binding to a capture binding ligand. Recruitment linkers, or signal carriers, are directly or indirectly attached to the target analyte to form an assay complex. The method further comprises detecting electron transfer between said ETM and said electrode.

Kits and apparatus comprising the compositions of the method are also provided.

BRIEF DESCRIPTION OF THE DRAWINGS

FIGS. 1A, 1B and 1C depict three preferred embodiments for attaching a target nucleic acid sequence to the electrode.

FIG. 1A depicts a target sequence 120 hybridized to a capture probe 100 linked via a attachment linker 106, which as outlined herein may be either a conductive oligomer or an insulator. The electrode 105 comprises a monolayer of passivation agent 107, which can comprise conductive oligomers (herein depicted as 108) and/or insulators (herein depicted as 109), and preferably both. As for all the embodiments depicted in the figures, n is an integer of at least 1, although as will be appreciated by those in the art, the system may not utilize a capture probe at all (i.e. n is zero), although this is generally not preferred. The upper limit of n will depend on the length of the target sequence and the required sensitivity. FIG. 1B depicts the use of a single capture extender probe 110 with a first portion 111 that will hybridize to a first portion of the target sequence 120 and a second portion that will hybridize to the capture probe 100. FIG. 1C depicts the use of two capture extender probes 110 and 130. The first capture extender probe 110 has a first portion 111 that will hybridize to a first portion of the target sequence 120 and a second portion 112 that will hybridize to a first portion 102 of the capture probe 100. The second capture extender probe 130 has a first portion 132 that will hybridize to a second portion of the target sequence 120 and a second portion 131 that will hybridize to a second portion 101 of the capture probe 100. As will be appreciated by those in the art, while these systems depict nucleic acid targets, these attachment configurations may be used with non-nucleic acid capture binding ligands; see for example FIG. 2C.

FIGS. 2A, 2B, 2C and 2D depict several embodiments of the invention. FIG. 2A is directed to the use of a capture binding ligand 200 attached via an attachment linker 106 to the electrode 105. Target analyte 210 binds to the capture binding ligand 200, and a solution binding ligand 22 with a directly attached recruitment linker 230 with ETMs 135. FIG. 2B depicts a similar embodiment using an indirectly attached recruitment linker 145 that binds to a second portion 240 of the solution binding ligand 220. FIG. 2C depicts the use of an anchor ligand 100 (referred to herein as an anchor probe when the ligand comprises nucleic acid) to bind the capture binding ligand 200 comprising a portion 120 that will bind to the anchor probe 100. As will be appreciated by those in the art, any of the FIG. 1 embodiments may be used here as well. FIG. 2D depicts the use of an amplifier probe 145. As will be appreciated by those in the art, any of the FIG. 3 amplifier probe configurations may be used here as well.

FIGS. 3A, 3B, 3C, 3D, 3E, 3F, 3G and 3H depict some of the embodiments of the invention. While depicted for nucleic acids, they can be used in non-nucleic acid embodiments as well. All of the monolayers depicted herein show the presence of both conductive oligomers 108 and insulators 107 in roughly a 1:1 ratio, although as discussed herein, a variety of different ratios may be used, or the insulator may be completely absent. In addition, as will be appreciated by those in the art, any one of these structures may be repeated for a particular target sequence; that is, for long target sequences, there may be multiple assay complexes formed. Additionally, any of the electrode-attachment embodiments of FIG. 3 may be used in any of these systems.

FIGS. 3A, 3B and 3D have the target sequence 120 containing the ETMs 135; as discussed herein, these may be added enzymatically, for example during a PCR reaction using nucleotides modified with ETMs, resulting in essentially random incorporation throughout the target sequence, or added to the terminus of the target sequence. FIG. 3C depicts the use of two different capture probes 100 and 100', that hybridize to different portions of the target sequence 120. As will be appreciated by those in the art, the 5'–3' orientation of the two capture probes in this embodiment is different.

FIG. 3C depicts the use of recruitment linkers (referred to herein as label probes when nucleic acids are used) 145 that hybridize directly to the target sequence 120. FIG. 3C shows the use of a label probe 145, comprising a first portion 141 that hybridizes to a portion of the target sequence 120, a second portion 142 comprising ETMs 135.

FIGS. 3E, 3F and 3G depict systems utilizing label probes 145 that do not hybridize directly to the target, but rather to amplifier probes 150 that are directly (FIG. 3E) or indirectly (FIGS. 3F and 3G) hybridized to the target sequence. FIG. 3E utilizes an amplifier probe 150 has a first portion 151 that hybridizes to the target sequence 120 and at least one second portion 152, i.e. the amplifier sequence, that hybridizes to the first portion 141 of the label probe. FIG. 3F is similar, except that a first label extender probe 160 is used, comprising a first portion 161 that hybridizes to the target sequence 120 and a second portion 162 that hybridizes to a first portion 151 of amplifier probe 150. A second portion 152 of the amplifier-probe 150 hybridizes to a first portion 141 of the label probe 140, which also comprises a recruitment linker 142 comprising ETMs 135. FIG. 3G adds a second label extender probe 170, with a first portion 171 that hybridizes to a portion of the target sequence 120 and a second portion that hybridizes to a portion of the amplifier probe.

FIG. 3H depicts a system that utilizes multiple label probes. The first portion 141 of the label probe 140 can hybridize to all or part of the recruitment linker 142.

FIGS. 4A and 4B show two competitive type assays of the invention. FIG. 4A utilizes the replacement of a target analyte 210 with a target analyte analog 310 comprising a directly attached recruitment linker 145. As will be appreciated by those in the art, an indirectly attached recruitment linker can also be used, as shown in FIG. 2B. FIG. 4B shows a competitive assay wherein the target analyte 210 and the target analyte analog 310 attached to the surface compete for binding of a solution binding ligand 220 with a directly attached recruitment linker 145 (again, an indirectly attached recruitment linker can also be used, as shown in FIG. 2B). In this case, a loss of signal may be seen.

FIGS. 5A, 5B, 5C, 5D and 5E depict additional embodiments of the invention. FIG. 5A shows a conformation wherein the addition of target alters the conformation of the binding ligands, causing the recruitment linker 145 to be placed near the monolayer surface. FIG. 5B shows the use of the present invention in candidate bioactive agent screening, wherein the addition of a drug candidate to target causes the solution binding ligand to dissociate, causing a loss of signal. In addition, the solution binding ligand may be added to another surface and be bound, as is generally depicted in FIG. 5C for enzymes. FIG. 5C depicts the use of an enzyme to cleave a substrate 260 comprising a recruitment linker 145, causing a loss of signal. The cleaved piece may also be added to an additional electrode, causing an increase in signal. FIG. 5D shows the use of two different capture binding ligands 200; these may also be attached to the electrode using capture extender ligands. FIG. 5E adds an additional "sandwich component" in the form of an additional solution binding ligand 250.

FIGS. 6A–6R depict nucleic acid detection systems. FIGS. 6A and 6B have the target sequence 5 containing the ETMs 6; as discussed herein, these may be added enzymatically, for example during a PCR reaction using nucleotides modified with ETMs, resulting in essentially random incorporation throughout the target sequence, or added to the terminus of the target sequence. FIG. 6A shows attachment of a capture probe 10 to the electrode 20 via a linker 15, which as discussed herein can be either a conductive oligomer 25 or an insulator 30. The target sequence 5 contains ETMs 6. FIG. 6B depicts the use of a capture extender probe 11, comprising a first portion 12 that hybridizes to a portion of the target sequence and a second portion 13 that hybridizes to the capture probe 10.

FIG. 6C depicts the use of two different capture probes 10 and 10', that hybridize to different portions of the target sequence 5. As will be appreciated by those in the art, the 5'-3' orientation of the two capture probes in this embodiment is different.

FIGS. 6D to 6H depict the use of label probes 40 that hybridize directly to the target sequence 5. FIG. 6D shows the use of a label probe 40, comprising a first portion 41 that hybridizes to a portion of the target sequence 5, a second portion 42 that hybridizes to the capture probe 10 and a recruitment linker 50 comprising ETMs 6. A similar embodiment is shown in FIG. 6E, where the label probe 40 has an additional recruitment linker 50. FIG. 6F depicts a label probe 40 comprising a first portion 41 that hybridizes to a portion of the target sequence 5 and a recruitment linker 50 with attached ETMs 6. The parentheses highlight that for any particular target sequence 5 more than one label probe 40 may be used, with n being an integer of at least 1. FIG. 6G depicts the use of the FIG. 6E label probe structures but includes the use of a single capture extender probe 11, with a first portion 12 that hybridizes to a portion of the target sequence and a second portion 13 that hybridizes to the capture probe 10. FIG. 6H depicts the use of the FIG. 6F label probe structures but utilizes two capture extender probes 11 and 16. The first capture extender probe 11 has a first portion 12 that hybridizes to a portion of the target sequence 5 and a second portion 13 that hybridizes to a first portion 14 of the capture probe 10. The second capture extender probe 16 has a first portion 18 that hybridizes to a second portion of the target sequence 5 and a second portion 17 that hybridizes to a second portion 19 of the capture probe 10.

FIGS. 6I, 6J and 6K depict systems utilizing label probes 40 that do not hybridize directly to the target, but rather to amplifier probes. Thus the amplifier probe 60 has a first portion 65 that hybridizes to the target sequence 5 and at least one second portion 70, i.e. the amplifier sequence, that hybridizes to the first portion 41 of the label probe.

FIGS. 6L, 6M and 6N depict systems that utilize a first label extender probe 80. In these embodiments, the label extender probe 80 has a first portion 81 that hybridizes to a portion of the target sequence 5, and a second portion 82 that hybridizes to the first portion 65 of the amplifier probe 60.

FIG. 6O depicts the use of two label extender probes 80 and 90. The first label extender probe 80 has a first portion 81 that hybridizes to a portion of the target sequence 5, and a second portion 82 that hybridizes to a first portion 62 of the amplifier probe 60. The second label extender probe 90 has a first portion 91 that hybridizes to a second portion of the target sequence 5 and a second portion 92 that hybridizes to a second portion 61 of the amplifier probe 60.

FIG. 6P depicts a system utilizing a label probe 40 hybridizing to the terminus of a target sequence 5.

FIGS. 6Q and 6R depict systems that utilizes multiple label probes. The first portion 41 of the label probe 40 can hybridize to all (FIG. 6R) or part (FIG. 6Q) of the recruitment linker 50.

FIG. 7 depicts the use of an activated carboxylate for the addition of a nucleic acid functionalized with a primary amine to a pre-formed SAM.

FIG. 8 shows a representative hairpin structure. 500 is a target binding sequence, 510 is a loop sequence, 520 is a self-complementary region, 530 is substantially complementary to a detection probe, and 530 is the "sticky end", that is, a portion that does not hybridize to any other portion of the probe, that contains the ETMs.

FIG. 9 depicts the synthesis of an adenosine comprising a ferrocene linked to the ribose.

FIG. 10 depicts the synthesis of a "branch" point (in this case an adenosine), to allow the addition of ETM polymers.

FIG. 11 depicts the synthetic scheme of a preferred attachment of an ETM, in this case ferrocene, to a nucleoside via the phosphate.

FIG. 12 depicts the synthetic scheme of ethylene glycol terminated conductive oligomers.

FIG. 13 depicts the synthesis of an insulator to the ribose of a nucleoside for attachment to an electrode.

FIGS. 14A, 14B, 14C, 14D, 14E, 14F, 14G, 14H, 14I, 14J and 14K depict a number of embodiments of the invention; the results are shown in Example 7.

FIGS. 15A–15O depict depict a number of different compositions of the invention; the results are shown in Example 7 and 8. FIG. 15A depicts I, also referred to as P290. FIG. 15B depicts II, also referred to as P291. FIG. 15C depicts III, also referred to as W31. FIG. 15D depicts IV, also referred to as N6. FIG. 15E depicts V, also referred to as P292. FIG. 51F depicts II, also referred to as C23. FIG. 15G depicts VII, also referred to as C15. FIG. 15H depicts VIII, also referred to as C95. FIG. 15I depicts Y63. FIG. 1J depicts another compound of the invention. FIG. 15K depicts N11. FIG. 15L depicts C131, with a phosphoramidite group and a DMT protecting group. FIG. 15M depicts W38, also with a phosphoramidite group and a DMT protecting group. FIG. 15N depicts the commercially available moiety that enables "branching" to occur, as its incorporation into a growing oligonucleotide chain results in addition at both the DMT protected oxygens. FIG. 15O depicts glen, also with a phosphoramidite group and a DMT protecting group, that serves as a non-nucleic acid linker. FIGS. 15A to 15G and 15J are shown without the phosphoramidite and protecting groups (i.e. DMT) that are readily added.

FIGS. 16A–16B depict representative scans from the experiments outlined in Example 7. Unless otherwise noted, all scans were run at initial voltage –0.11 V, final voltage 0.5 V, with points taken every 10 mV, amplitude of 0.025, frequency of 10 Hz, a sample period of 1 sec, a quiet time of 2 sec. FIG. 16A has a peak potential of 0.160 V, a peak current of $1.092 \times 10^{-8}$ A, and a peak A of $7.563 \times 10^{-10}$ VA.

FIGS. 18A and 18B depicts two phosphate attachments of conductive oligomers that can be used to add the conductive oligomers at the 5' position, or any position.

FIG. 19 depicts a schematic of the synthesis of simultaneous incorporation of multiple ETMs into a nucleic acid, using a "branch" point nucleoside.

FIG. 20 depicts a schematic of an alternate method of adding large numbers of ETMs simultaneously to a nucleic acid using a "branch" point phosphoramidite, as is known in the art. As will be appreciated by those in the art, each end point can contain any number of ETMs.

FIGS. 21A, 21B, 21C, 21D and 21E depict different possible configurations of label probes and attachments of ETMs. In FIGS. 21A–C, the recruitment linker is nucleic acid; in FIGS. 21D and E, is is not. A=nucleoside replacement; B=attachment to a base; C=attachment to a ribose; D=attachment to a phosphate; E=metallocene polymer (although as described herein, this can be a polymer of other ETMs as well), attached to a base, ribose or phosphate (or other backbone analogs); F=dendrimer structure, attached via a base, ribose or phosphate (or other backbone analogs); G=attachment via a "branching" structure, through base, ribose or phosphate (or other backbone analogs); H=attachment of metallocene (or other ETM) polymers; I=attachment via a dendrimer structure; J=attachment using standard linkers.

FIGS. 22A and 22B depict some of the sequences used in the Examples.

DETAILED DESCRIPTION OF THE INVENTION

Figure 17:
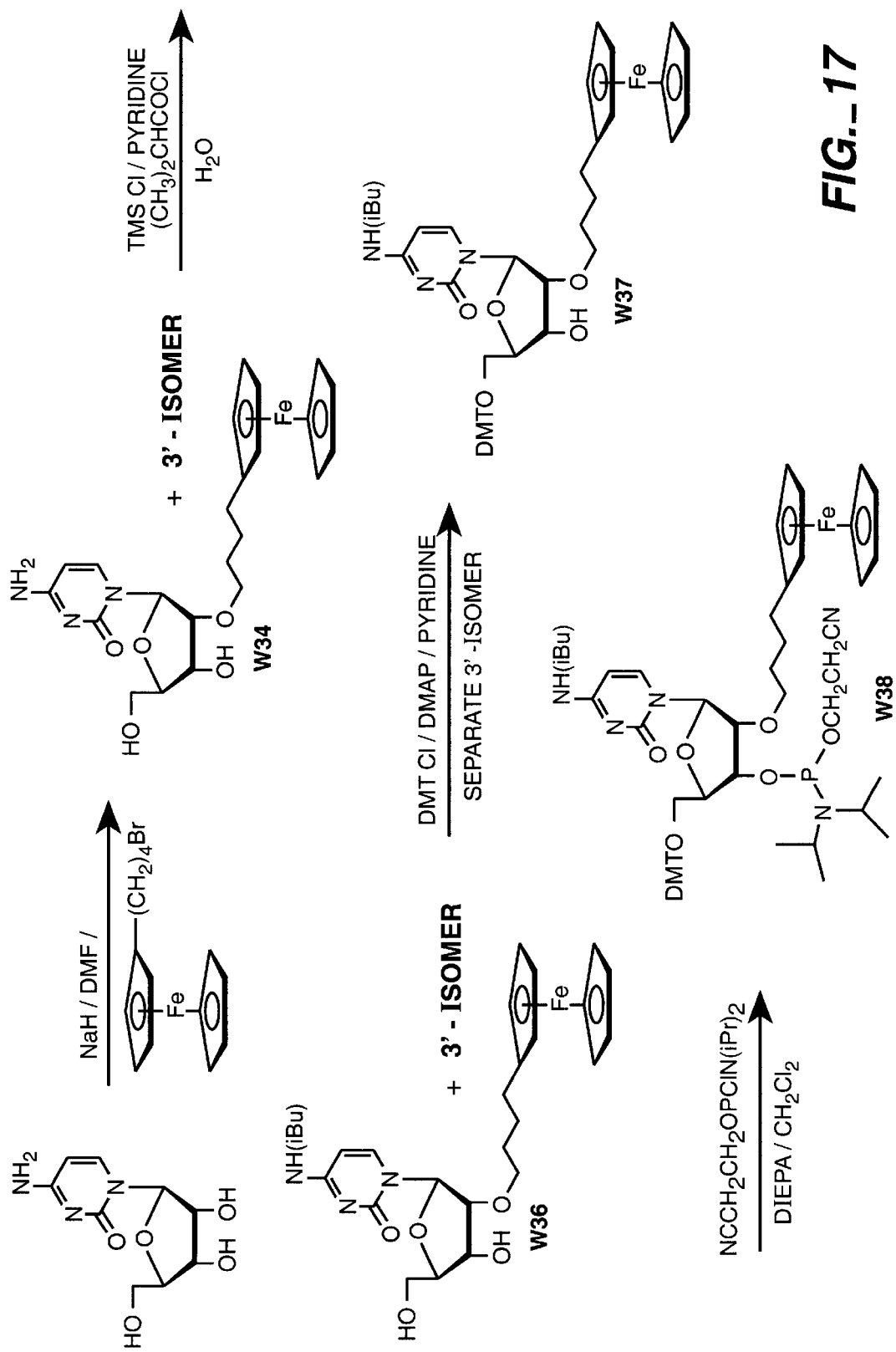
FIG. 17 depicts the synthetic scheme for a ribose linked ETM, W38.

The present invention is directed to the electronic detection of analytes. Previous work, described in PCT US97/20014, is directed to the detection of nucleic acids, and utilizes nucleic acids covalently attached to electrodes using conductive oligomers, i.e. chemical "wires". Upon formation of double stranded nucleic acids containing electron transfer moieties (ETMs), electron transfer can proceed through the stacked π-orbitals of the heterocyclic bases to the electrode, thus enabling electronic detection of target nucleic acids. In the absence of the stacked π-orbitals, i.e. when the target strand is not present, electron transfer is negligible, thus allowing the use of the system as an assay. This previous work also reported on the use of self-assembled monolayers (SAMs) to electronically shield the electrodes from solution components and significantly decrease the amount of non-specific binding to the electrodes.

The present invention is directed to the discovery that present or absence of ETMs can be directly detected on a surface of a monolayer if the monolayer comprises conductive oligomers, and preferably mixtures of conductive oligomers and insulators. Thus, for example, when the target analyte is a nucleic acid, the electrons from the ETMs need not travel through the stacked n orbitals in order to generate a signal. Instead, the presence of ETMs on the surface of a SAM, that comprises conductive oligomers, can be directly detected. Thus, upon binding of a target analyte to a binding species on the surface, a recruitment linker comprising an ETM is brought to the surface, and detection of the ETM can proceed. Thus, the role of the target analyte and binding species is to provide specificity for a recruitment of ETMs to the surface, where they can be detected using the electrode. Without being bound by theory, one possible mechanism is that the role of the SAM comprising the conductive oligomers is to "raise" the electronic surface of the electrode, while still providing the benefits of shielding the electrode from solution components and reducing the amount of non-specific binding to the electrodes.

The invention can be generally described as follows, with a number of possible embodiments depicted in the Figures. In a preferred embodiment, as depicted in FIG. 2, an electrode comprising a self-assembled monolayer (SAM) of conductive oligomers, and preferably a mixture of conductive oligomers and insulators, and a covalently attached target analyte binding ligand (frequently referred to herein as a "capture binding ligand") is made. The target analyte is added, which binds to the support-bound binding ligand. A solution binding ligand is added, which may be the same or different from the first binding ligand, which can also bind to the target analyte, forming a "sandwich" of sorts. The solution binding ligand either comprises a recruitment linker containing ETMs, or comprises a portion that will either directly or indirectly bind a recruitment linker containing the ETMs. This "recruitment" of ETMs to the surface of the monolayer allows electronic detection via electron transfer between the ETM and the electrode. In the absence of the target analyte, the recruitment linker is either washed away or not in sufficient proximity to the surface to allow detection.

In an alternate preferred embodiment, as depicted in FIG. 4, a competitive binding type assay is run. In this embodiment, the target analyte in the sample is replaced by a target analyte analog as is described below and generally known in the art. The analog comprises a directly or indirectly attached recruitment linker comprising at least one ETM. The binding of the analog to the capture binding ligand recruits the ETM to the surface and allows detection based on electron transfer between the ETM and the electrode.

In an additional preferred embodiment, as depicted in FIG. 4B, a competitive assay wherein the target analyte and a target analyte analog attached to the surface compete for binding of a solution binding ligand with a directly or indirectly attached recruitment linker. In this case, a loss of signal may be seen.

Accordingly, the present invention provides methods and compositions useful in the detection of target analytes. By "target analyte" or "analyte" or grammatical equivalents herein is meant any molecule or compound to be detected and that can bind to a binding species, defined below. Suitable analytes include, but not limited to, small chemical molecules such as environmental or clinical chemical or pollutant or biomolecule, including, but not limited to, pesticides, insecticides, toxins, therapeutic and abused drugs, hormones, antibiotics, antibodies, organic materials, etc. Suitable biomolecules include, but are not limited to, proteins (including enzymes, immunoglobulins and glycoproteins), nucleic acids, lipids, lectins, carbohydrates, hormones, whole cells (including procaryotic (such as pathogenic bacteria) and eucaryotic cells, including mammalian tumor cells), viruses, spores, etc. Particularly preferred analytes are proteins including enzymes; drugs, cells; antibodies; antigens; cellular membrane antigens and receptors (neural, hormonal, nutrient, and cell surface receptors) or their ligands.

By "proteins" or grammatical equivalents herein is meant proteins, oligopeptides and peptides, and analogs, including proteins containing non-naturally occuring amino acids and amino acid analogs, and peptidomimetic structures.

As will be appreciated by those in the art, a large number of analytes may be detected using the present methods; basically, any target analyte for which a binding ligand, described below, may be made may be detected using the methods of the invention.

By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970) Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev: (1995) pp169–176). Several nucleic acid analogs are described in Rawls, C & E News Jun. 2, 1997 page 35. All of these references are hereby expressly incorporated by reference. These modifications of the ribose-phosphate backbone may be done to facilitate the addition of ETMs, or to increase the stability and half-life of such molecules in physiological environments.

As will be appreciated by those in the art, all of these nucleic acid analogs may find use in the present invention. In addition, mixtures of naturally occurring nucleic acids and analogs can be made; for example, at the site of conductive oligomer or ETM attachment, an analog structure may be used. Alternatively, mixtures of different nucleic acid analogs, and mixtures of naturally occuring nucleic acids and analogs may be made.

Particularly preferred are peptide nucleic acids (PNA) which includes peptide nucleic acid analogs. These backbones are substantially non-ionic under neutral conditions, in contrast to the highly charged phosphodiester backbone of naturally occurring nucleic acids. This results in two advantages. First, the PNA backbone exhibits improved hybridization kinetics. PNAs have larger changes in the melting temperature (Tm) for mismatched versus perfectly matched basepairs. DNA and RNA typically exhibit a 2–4° C. drop in Tm for an internal mismatch. With the non-ionic PNA backbone, the drop is closer to 7–9° C. Similarly, due to their non-ionic nature, hybridization of the bases attached to these backbones is relatively insensitive to salt concentration. This is particularly advantageous in the systems of the present invention, as a reduced salt hybridization solution has a lower Faradaic current than a physiological salt solution (in the range of 150 mM).

The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc. A preferred embodiment utilizes isocytosine and isoguanine in nucleic acids designed to be complementary to other probes, rather than target sequences, as this reduces non-specific hybridization, as is generally described in U.S. Pat. No. 5,681,702. As used herein, the term "nucleoside" includes nucleotides as well as nucleoside and nucleotide analogs, and modified nucleosides such as amino modified nucleosides. In addition, "nucleoside" includes non-naturally occuring analog structures. Thus for example the individual units of a peptide nucleic acid, each containing a base, are referred to herein as a nucleoside.

In one embodiment, nucleic acid target analytes are not preferred.

As will be appreciated by those in the art, a large number of analytes may be detected using the present methods; basically, any target analyte for which a binding ligand, described below, may be made may be detected using the methods of the invention.

Accordingly, the present invention provides methods and compositions useful in the detection of target analytes. In a preferred embodiment, the compositions comprise an electrode comprising a monolayer. By "electrode" herein is meant a composition, which, when connected to an electronic device, is able to sense a current or charge and convert it to a signal. Thus, an electrode is an ETM as described herein. Preferred electodes are known in the art and include, but are not limited to, certain metals and their oxides, including gold; platinum; palladium; silicon; aluminum; metal oxide electrodes including platinum oxide, titanium oxide, tin oxide, indium tin oxide, palladium oxide, silicon oxide, aluminum oxide, molybdenum oxide ($Mo_2O_6$), tungsten oxide ($WO_3$) and ruthenium oxides; and carbon (including glassy carbon electrodes, graphite and carbon paste). Preferred electrodes include gold, silicon, carbon and metal oxide electrodes, with gold being particularly preferred.

The electrodes described herein are depicted as a flat surface, which is only one of the possible conformations of the electrode and is for schematic purposes only. The conformation of the electrode will vary with the detection method used. For example, flat planar electrodes may be preferred for optical detection methods, or when arrays of nucleic acids are made, thus requiring addressable locations for both synthesis and detection. Alternatively, for single probe analysis, the electrode may be in the form of a tube, with the SAMs comprising conductive oligomers and nucleic acids bound to the inner surface. This allows a maximum of surface area containing the nucleic acids to be exposed to a small volume of sample.

The electrode comprises a monolayer, comprising conductive oligomers. By "monolayer" or "self-assembled monolayer" or "SAM" herein is meant a relatively ordered assembly of molecules spontaneously chemisorbed on a surface, in which the molecules are oriented approximately parallel to each other and roughly perpendicular to the surface. Each of the molecules includes a functional group that adheres to the surface, and a portion that interacts with neighboring molecules in the monolayer to form the relatively ordered array. A "mixed" monolayer comprises a heterogeneous monolayer, that is, where at least two different molecules make up the monolayer. The SAM may comprise conductive oligomers alone, or a mixture of conductive oligomers and insulators. As outlined herein, the use of a monolayer reduces the amount of non-specific binding of biomolecules to the surface, and, in the case of nucleic acids, increases the efficiency of oligonucleotide hybridization as a result of the distance of the oligonucleotide from the electrode. Thus, a monolayer facilitates the maintenance of the target analyte away from the electrode surface. In addition, a monolayer serves to keep charge carriers away from the surface of the electrode. Thus, this layer helps to prevent electrical contact between the electrodes and the ETMs, or between the electrode and charged species within the solvent. Such contact can result in a direct "short circuit" or an indirect short circuit via charged species which may be present in the sample. Accordingly, the monolayer is preferably tightly packed in a uniform layer on the electrode surface, such that a minimum of "holes" exist. The monolayer thus serves as a physical barrier to block solvent accesibility to the electrode.

In a preferred embodiment, the monolayer comprises conductive oligomers. By "conductive oligomer" herein is meant a substantially conducting oligomer, preferably linear, some embodiments of which are referred to in the literature as "molecular wires". By "substantially conducting" herein is meant that the oligomer is capable of transfering electrons at 100 Hz. Generally, the conductive oligomer has substantially overlapping π-orbitals, i.e. conjugated π-orbitals, as between the monomeric units of the conductive oligomer, although the conductive oligomer may also contain one or more sigma (σ) bonds. Additionally, a conductive oligomer may be defined functionally by its ability to inject or receive electrons into or from an associated ETM. Furthermore, the conductive oligomer is more conductive than the insulators as defined herein. Additionally, the conductive oligomers of the invention are to be distinguished from electroactive polymers, that themselves may donate or accept electrons.

In a preferred embodiment, the conductive oligomers have a conductivity, S, of from between about $10^{-6}$ to about $10^4$ $\Omega^{-1}cm^{-1}$, with from about $10^{-5}$ to about $10^3$ $\Omega^{-1}cm^{-1}$ being preferred, with these S values being calculated for molecules ranging from about 20 Å to about 200 Å. As described below, insulators have a conductivity S of about $10^{-7}$ $\Omega^{-1}cm^{-1}$ or lower, with less than about $10^{-8}$ $\Omega^{-1}cm^{-1}$ being preferred. See generally Gardner et al., Sensors and Actuators A 51 (1995) 57–66, incorporated herein by reference.

Desired characteristics of a conductive oligomer include high conductivity, sufficient solubility in organic solvents and/or water for synthesis and use of the compositions of the invention, and preferably chemical resistance to reactions that occur i) during nucleic acid synthesis (such that nucleosides containing the conductive oligomers may be added to a nucleic acid synthesizer during the synthesis of the compositions of the invention), ii) during the attachment of the conductive oligomer to an electrode, or iii) during hybridization assays. In addition, conductive oligomers that will promote the formation of self-assembled monolayers are preferred.

The oligomers of the invention comprise at least two monomeric subunits, as described herein. As is described more fully below, oligomers include homo- and heterooligomers, and include polymers.

In a preferred embodiment, the conductive oligomer has the structure depicted in Structure 1:

Structure 1

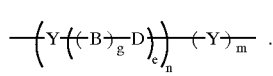

As will be understood by those in the art, all of the structures depicted herein may have additional atoms or structures; i.e. the conductive oligomer of Structure 1 may be attached to ETMs, such as electrodes, transition metal complexes, organic ETMs, and metallocenes, and to capture binding ligands such as nucleic acids, or to several of these. Unless otherwise noted, the conductive oligomers depicted herein will be attached at the left side to an electrode; that is, as depicted in Structure 1, the left "Y" is connected to the electrode as described herein. If the conductive oligomer is to be attached to a binding ligand, the right "Y", if present, is attached to the capture binding ligand, either directly or through the use of a linker, as is described herein.

In this embodiment, Y is an aromatic group, n is an integer from 1 to 50, g is either 1 or zero, e is an integer from zero to 10, and m is zero or 1. When g is 1, B—D is a conjugated bond, preferably selected from acetylene, alkene, substituted alkene, amide, azo, —C=N— (including —N=C—, —CR=N— and —N=CR—), —Si=Si—, and —Si=C— (including —C=Si—, —Si=CR— and —CR=Si—). When g is zero, e is preferably 1, D is preferably carbonyl, or a heteroatom moiety, wherein the heteroatom is selected from oxygen, sulfur, nitrogen, silicon or phosphorus. Thus, suitable heteroatom moieties include, but are not limited to, —NH and —NR, wherein R is as defined herein; substituted sulfur; sulfonyl (—SO$_2$—) sulfoxide (—SO—); phosphine oxide (—PO— and —RPO—); and thiophosphine (—PS— and —RPS—). However, when the conductive oligomer is to be attached to a gold electrode, as outlined below, sulfur derivatives are not preferred.

By "aromatic group" or grammatical equivalents herein is meant an aromatic monocyclic or polycyclic hydrocarbon moiety generally containing 5 to 14 carbon atoms (although larger polycyclic rings structures may be made) and any carbocylic ketone or thioketone derivative thereof, wherein the carbon atom with the free valence is a member of an aromatic ring. Aromatic groups include arylene groups and aromatic groups with more than two atoms removed. For the purposes of this application aromatic includes heterocycle. "Heterocycle" or "heteroaryl" means an aromatic group wherein 1 to 5 of the indicated carbon atoms are replaced by a heteroatom chosen from nitrogen, oxygen, sulfur, phosphorus, boron and silicon wherein the atom with the free valence is a member of an aromatic ring, and any heterocyclic ketone and thioketone derivative thereof. Thus, heterocycle includes thienyl, furyl, pyrrolyl, pyrimidinyl, oxalyl, indolyl, purinyl, quinolyl, isoquinolyl, thiazolyl, imidozyl, etc.

Importantly, the Y aromatic groups of the conductive oligomer may be different, i.e. the conductive oligomer may be a heterooligomer. That is, a conductive oligomer may comprise a oligomer of a single type of Y groups, or of multiple types of Y groups.

The aromatic group may be substituted with a substitution group, generally depicted herein as R. R groups may be added as necessary to affect the packing of the conductive oligomers, i.e. R groups may be used to alter the association of the oligomers in the monolayer. R groups may also be added to 1) alter the solubility of the oligomer or of compositions containing the oligomers; 2) alter the conjugation or electrochemical potential of the system; and 3) alter the charge or characteristics at the surface of the monolayer.

In a preferred embodiment, when the conductive oligomer is greater than three subunits, R groups are preferred to increase solubility when solution synthesis is done. However, the R groups, and their positions, are chosen to minimally effect the packing of the conductive oligomers on a surface, particularly within a monolayer, as described below. In general, only small R groups are used within the monolayer, with larger R groups generally above the surface of the monolayer. Thus for example the attachment of methyl groups to the portion of the conductive oligomer within the monolayer to increase solubility is preferred, with attachment of longer alkoxy groups, for example, C3 to C10, is preferably done above the monolayer surface. In general, for the systems described herein, this generally means that attachment of sterically significant R groups is not done on any of the first two or three oligomer subunits, depending on the average length of the molecules making up the monolayer.

Suitable R groups include, but are not limited to, hydrogen, alkyl, alcohol, aromatic, amino, amido, nitro, ethers, esters, aldehydes, sulfonyl, silicon moieties, halogens, sulfur containing moieties, phosphorus containing moieties, and ethylene glycols. In the structures depicted herein, R is hydrogen when the position is unsubstituted. It should be noted that some positions may allow two substitution groups, R and R', in which case the R and R' groups may be either the same or different.

By "alkyl group" or grammatical equivalents herein is meant a straight or branched chain alkyl group, with straight chain alkyl groups being preferred. If branched, it may be branched at one or more positions, and unless specified, at any position. The alkyl group may range from about 1 to about 30 carbon atoms (C1–C30), with a preferred embodiment utilizing from about 1 to about 20 carbon atoms (C1–C20), with about C1 through about C12 to about C15 being preferred, and C1 to C5 being particularly preferred, although in some embodiments the alkyl group may be much larger. Also included within the definition of an alkyl group are cycloalkyl groups such as C5 and C6 rings, and heterocyclic rings with nitrogen, oxygen, sulfur or phosphorus. Alkyl also includes heteroalkyl, with heteroatoms of sulfur, oxygen, nitrogen, and silicone being preferred. Alkyl includes substituted alkyl groups. By "substituted alkyl group" herein is meant an alkyl group further comprising one or more substitution moieties "R", as defined above.

By "amino groups" or grammatical equivalents herein is meant —NH$_2$, —NHR and —NR$_2$ groups, with R being as defined herein.

By "nitro group" herein is meant an —NO$_2$ group.

By "sulfur containing moieties" herein is meant compounds containing sulfur atoms, including but not limited to, thia-, thio- and sulfo-compounds, thiols (—SH and —SR), and sulfides (—RSR—). By "phosphorus containing moieties" herein is meant compounds containing phosphorus, including, but not limited to, phosphines and phosphates. By "silicon containing moieties" herein is meant compounds containing silicon.

By "ether" herein is meant an —O—R group. Preferred ethers include alkoxy groups, with —O—(CH$_2$)$_2$CH$_3$ and —O—(CH$_2$)$_4$CH$_3$ being preferred.

By "ester" herein is meant a —COOR group.

By "halogen" herein is meant bromine, iodine, chlorine, or fluorine. Preferred substituted alkyls are partially or fully halogenated alkyls such as CF$_3$, etc.

By "aldehyde" herein is meant —RCHO groups.

By "alcohol" herein is meant —OH groups, and alkyl alcohols —ROH.

By "amido" herein is meant —RCONH— or RCONR— groups.

By "ethylene glycol" or "(poly)ethylene glycol" herein is meant a —(O—CH$_2$—CH$_2$)$_n$— group, although each carbon atom of the ethylene group may also be singly or doubly substituted, i.e. —(O—CR$_2$—CR$_2$)$_n$—, with R as described above. Ethylene glycol derivatives with other heteroatoms in place of oxygen (i.e. —(N—CH$_2$—CH$_2$)$_n$— or —(S—CH$_2$—CH$_2$)$_n$—, or with substitution groups) are also preferred.

Preferred substitution groups include, but are not limited to, methyl, ethyl, propyl, alkoxy groups such as —O—(CH$_2$)$_2$CH$_3$ and —O—(CH$_2$)$_4$CH$_3$ and ethylene glycol and derivatives thereof.

Preferred aromatic groups include, but are not limited to, phenyl, naphthyl, naphthalene, anthracene, phenanthroline, pyrole, pyridine, thiophene, porphyrins, and substituted derivatives of each of these, included fused ring derivatives.

In the conductive oligomers depicted herein, when g is 1, B—D is a bond linking two atoms or chemical moieties. In a preferred embodiment, B—D is a conjugated bond, containing overlapping or conjugated π-orbitals.

Preferred B—D bonds are selected from acetylene (—C≡C—, also called alkyne or ethyne), alkene (—CH=CH—, also called ethylene), substituted alkene (—CR=CR—, —CH=CR— and —CR=CH—), amide (—NH—CO— and —NR—CO— or —CO—NH— and —CO—NR—), azo (—N=N—), esters and thioesters (—CO—O—, —O—CO—, —CS—O— and —O—CS—) and other conjugated bonds such as (—CH=N—, —CR=N—, —N=CH— and —N=CR—), (—SiH=SiH—, —SiR=SiH—, —SiR=SiH—, and —SiR=SiR—), (—SiH=CH—, —SiR=CH—, —SiH=CR—, —SiR=CR—, —CH=SiH—, —CR=SiH—, —CH=SiR—, and —CR=SiR—). Particularly preferred B—D bonds are acetylene, alkene, amide, and substituted derivatives of these three, and azo. Especially preferred B—D bonds are acetylene, alkene and amide. The oligomer components attached to double bonds may be in the trans or cis conformation, or mixtures. Thus, either B or D may include carbon, nitrogen or silicon. The substitution groups are as defined as above for R.

When g=0 in the Structure 1 conductive oligomer, e is preferably 1 and the D moiety may be carbonyl or a heteroatom moiety as defined above.

As above for the Y rings, within any single conductive oligomer, the B—D bonds (or D moieties, when g=0) may be all the same, or at least one may be different. For example, when m is zero, the terminal B—D bond may be an amide bond, and the rest of the B—D bonds may be acetylene bonds. Generally, when amide bonds are present, as few amide bonds as possible are preferable, but in some embodiments all the B—D bonds are amide bonds. Thus, as outlined above for the Y rings, one type of B—D bond may be present in the conductive oligomer within a monolayer as described below, and another type above the monolayer level, for example to give greater flexibility for analyte-binding ligand binding, when the capture binding ligand is attached via a conductive oligomer.

In the structures depicted herein, n is an integer from 1 to 50, although longer oligomers may also be used (see for example Schumm et al., Angew. Chem. Int. Ed. Engl. 1994 33(13):1360). Without being bound by theory, it appears that for efficient association of binding ligands and targets, the reaction should occur at a distance from the surface. Thus, for example, for nucleic acid hybridization of target nucleic acids to capture probes on a surface, the hybridization should occur at a distance from the surface, i.e. the kinetics of hybridization increase as a function of the distance from the surface, particularly for long oligonucleotides of 200 to 300 basepairs. Accordingly, when a nucleic acid is attached via a conductive oligomer, as is more fully described below, the length of the conductive oligomer is such that the closest nucleotide of the nucleic acid is positioned from about 6 Å to about 100 Å (although distances of up to 500 Å may be used) from the electrode surface, with from about 15 Å to about 60 Å being preferred and from about 25 Å to about 60 Å also being preferred. Accordingly, n will depend on the size of the aromatic group, but generally will be from about 1 to about 20, with from about 2 to about 15 being preferred and from about 3 to about 10 being especially preferred.

In the structures depicted herein, m is either 0 or 1. That is, when m is 0, the conductive oligomer may terminate in the B—D bond or D moiety, i.e. the D atom is attached to the capture binding ligand either directly or via a linker. In some embodiments, for example when the conductive oligomer is attached to a phosphate of the ribose-phosphate backbone of a nucleic acid, there may be additional atoms, such as a linker, attached between the conductive oligomer and the nucleic acid. Additionally, as outlined below, the D atom may be the nitrogen atom of the amino-modified ribose. Alternatively, when m is 1, the conductive oligomer may terminate in Y, an aromatic group, i.e. the aromatic group is attached to the capture binding ligand or linker.

As will be appreciated by those in the art, a large number of possible conductive oligomers may be utilized. These include conductive oligomers falling within the Structure 1 and Structure 8 formulas, as well as other conductive oligomers, as are generally known in the art, including for example, compounds comprising fused aromatic rings or Teflon®-like oligomers, such as —(CF$_2$)$_n$—, —(CHF)$_n$— and —(CFR)$_n$—. See for example, Schumm et al., Angew. Chem. Intl. Ed. Engl. 33:1361 (1994); Grosshenny et al., Platinum Metals Rev. 40(1):26–35 (1996); Tour, Chem. Rev. 96:537–553 (1996); Hsung et al., Organometallics 14:4808–4815 (1995; and references cited therein, all of which are expressly incorporated by reference.

Particularly preferred conductive oligomers of this embodiment are depicted below:

Structure 2

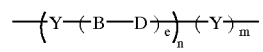

Structure 2 is Structure 1 when 9 is 1. Preferred embodiments of Structure 2 include: e is zero, Y is pyrole or substituted pyrole; e is zero, Y is thiophene or substituted thiophene; e is zero, Y is furan or substituted furan; e is zero, Y is phenyl or substituted phenyl; e is zero, Y is pyridine or substituted pyridine; e is 1, B—D is acetylene and Y is phenyl or substituted phenyl (see Structure 4 below). A preferred embodiment of Structure 2 is also when e is one, depicted as Structure 3 below:

Structure 3

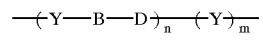

Preferred embodiments of Structure 3 are: Y is phenyl or substituted phenyl and B—D is azo; Y is phenyl or substituted phenyl and B—D is acetylene; Y is phenyl or substituted phenyl and B—D is alkene; Y is pyridine or substituted pyridine and B—D is acetylene; Y is thiophene or substituted thiophene and B—D is acetylene; Y is furan or substituted furan and B—D is acetylene; Y is thiophene or furan (or substituted thiophene or furan) and B—D are alternating alkene and acetylene bonds.

Most of the structures depicted herein utilize a Structure 3 conductive oligomer. However, any Structure 3 oligomers may be substituted with any of the other structures depicted herein, i.e. Structure 1 or 8 oligomer, or other conducting oligomer, and the use of such Structure 3 depiction is not meant to limit the scope of the invention.

Particularly preferred embodiments of Structure 3 include Structures 4, 5, 6 and 7, depicted below:

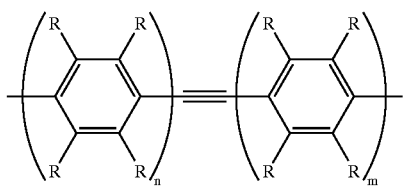

Structure 4

Particularly preferred embodiments of Structure 4 include: n is two, m is one, and R is hydrogen; n is three, m is zero, and R is hydrogen; and the use of R groups to increase solubility.

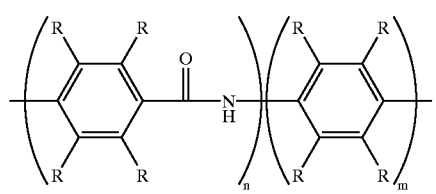

Structure 5

When the B—D bond is an amide bond, as in Structure 5, the conductive oligomers are pseudopeptide oligomers. Although the amide bond in Structure 5 is depicted with the carbonyl to the left, i.e. —CONH—, the reverse may also be used, i.e. —NHCO—. Particularly preferred embodiments of Structure 5 include: n is two, m is one, and R is hydrogen; n is three, m is zero, and R is hydrogen (in this embodiment, the terminal nitrogen (the D atom) may be the nitrogen of the amino-modified ribose); and the use of R groups to increase solubility.

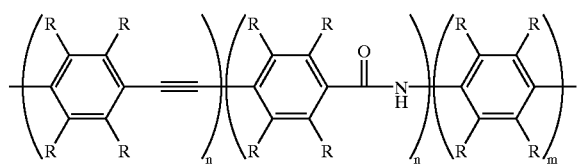

Structure 6

Preferred embodiments of Structure 6 include the first n is two, second n is one, m is zero, and all R groups are hydrogen, or the use of R groups to increase solubility.

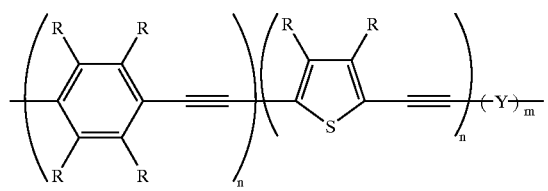

Structure 7

Preferred embodiments of Structure 7 include: the first n is three, the second n is from 1–3, with m being either 0 or 1, and the use of R groups to increase solubility.

In a preferred embodiment, the conductive oligomer has the structure depicted in Structure 8:

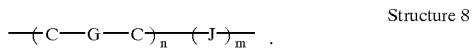

Structure 8

In this embodiment, C are carbon atoms, n is an integer from 1 to 50, m is 0 or 1, J is a heteroatom selected from the group consisting of oxygen, nitrogen, silicon, phosphorus, sulfur, carbonyl or sulfoxide, and G is a bond selected from alkane, alkene or acetylene, such that together with the two carbon atoms the C—G—C group is an alkene (—CH=CH—), substituted alkene (—CR=CR—) or mixtures thereof (—CH=CR— or —CR=CH—), acetylene (—C≡C—), or alkane (—CR$_2$—CR$_2$—, with R being either hydrogen or a substitution group as described herein). The G bond of each subunit may be the same or different than the G bonds of other subunits; that is, alternating oligomers of alkene and acetylene bonds could be used, etc. However, when G is an alkane bond, the number of alkane bonds in the oligomer should be kept to a minimum, with about six or less sigma bonds per conductive oligomer being preferred. Alkene bonds are preferred, and are generally depicted herein, although alkane and acetylene bonds may be substituted in any structure or embodiment described herein as will be appreciated by those in the art.

In some embodiments, for example when ETMs are not present, if m=0 then at least one of the G bonds is not an alkane bond.

In a preferred embodiment, the m of Structure 8 is zero. In a particularly preferred embodiment, m is zero and G is an alkene bond, as is depicted in Structure 9:

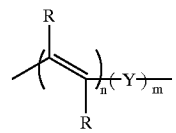

Structure 9

The alkene oligomer of structure 9, and others depicted herein, are generally depicted in the preferred trans configuration, although oligomers of cis or mixtures of trans and cis may also be used. As above, R groups may be added to alter the packing of the compositions on an electrode, the hydrophilicity or hydrophobicity of the oligomer, and the flexibility, i.e. the rotational, torsional or longitudinal flexibility of the oligomer. n is as defined above.

In a preferred embodiment, R is hydrogen, although R may be also alkyl groups and polyethylene glycols or derivatives.

In an alternative embodiment, the conductive oligomer may be a mixture of different types of oligomers, for example of structures 1 and 8.

In addition, the terminus of at least some of the conductive oligomers in the monolayer are electronically exposed. By "electronically exposed" herein is meant that upon the placement of an ETM in close proximity to the terminus, and after initiation with the appropriate signal, a signal dependent on the presence of the ETM may be detected. The conductive oligomers may or may not have terminal groups. Thus, in a preferred embodiment, there is no additional terminal group, and the conductive oligomer terminates with one of the groups depicted in Structures 1 to 9; for example, a B—D bond such as an acetylene bond. Alternatively, in a preferred embodiment, a terminal group is added, sometimes depicted herein as "Q". A terminal group may be used for several reasons; for example, to contribute to the electronic availability of the conductive oligomer for detection of ETMs, or to alter the surface of the SAM for other reasons, for example to prevent non-specific binding. For example, there may be negatively charged groups on the terminus to form a negatively charged surface such that when the target analyte is nucleic acid such as DNA or RNA, the nucleic acid is repelled or prevented from lying down on the surface, to facilitate hybridization. Preferred terminal groups include —$NH_2$, —OH, —COOH, and alkyl groups such as —$CH_3$, and (poly)alkyloxides such as (poly)ethylene glycol, with —$OCH_2CH_2OH$, —$(OCH_2CH_2O)_2H$, —$(OCH_2CH_2O)_3H$, and —$(OCH_2CH_2O)_4H$ being preferred.

In one embodiment, it is possible to use mixtures of conductive oligomers with different types of terminal groups. Thus, for example, some of the terminal groups may facilitate detection, and some may prevent non-specific binding.

It will be appreciated that the monolayer may comprise different conductive oligomer species, although preferably the different species are chosen such that a reasonably uniform SAM can be formed. Thus, for example, when capture binding ligands are covalently attached to the electrode using conductive oligomers, it is possible to have one type of conductive oligomer used to attach the capture binding ligand, and another type functioning to detect the ETM. Similarly, it may be desirable to have mixtures of different lengths of conductive oligomers in the monolayer, to help reduce non-specific signals. Thus, for example, preferred embodiments utilize conductive oligomers that terminate below the surface of the rest of the monolayer, i.e. below the insulator layer, if used, or below some fraction of the other conductive oligomers. Similarly, the use of different conductive oligomers may be done to facilitate monolayer formation, or to make monolayers with altered properties.

In a preferred embodiment, the monolayer may further comprise insulator moieties. By "insulator" herein is meant a substantially nonconducting oligomer, preferably linear. By "substantially nonconducting" herein is meant that the insulator will not transfer electrons at 100 Hz. The rate of electron transfer through the insulator is preferably slower than the rate through the conductive oligomers described herein.

In a preferred embodiment, the insulators have a conductivity, S, of about $10^{-7}$ $\Omega^{-1}cm^{-1}$ or lower, with less than about $10^{-8}$ $\Omega^{-1}cm^{-1}$ being preferred. See generally Gardner et al., supra.

Generally, insulators are alkyl or heteroalkyl oligomers or moieties with sigma bonds, although any particular insulator molecule may contain aromatic groups or one or more conjugated bonds. By "heteroalkyl" herein is meant an alkyl group that has at least one heteroatom, i.e. nitrogen, oxygen, sulfur, phosphorus, silicon or boron included in the chain. Alternatively, the insulator may be quite similar to a conductive oligomer with the addition of one or more heteroatoms or bonds that serve to inhibit or slow, preferably substantially, electron transfer.

Suitable insulators are known in the art, and include, but are not limited to, —$(CH_2)_n$—, —$(CRH)_n$—, and —$(CR_2)_n$—, ethylene glycol or derivatives using other heteroatoms in place of oxygen, i.e. nitrogen or sulfur (sulfur derivatives are not preferred when the electrode is gold).

As for the conductive oligomers, the insulators may be substituted with R groups as defined herein to alter the packing of the moieties or conductive oligomers on an electrode, the hydrophilicity or hydrophobicity of the insulator, and the flexibility, i.e. the rotational, torsional or longitudinal flexibility of the insulator. For example, branched alkyl groups may be used. Similarly, the insulators may contain terminal groups, as outlined above, particularly to influence the surface of the monolayer.

The length of the species making up the monolayer will vary as needed. As outlined above, it appears that binding is more efficient at a distance from the surface. The species to which capture binding ligands are attached (as outlined below, these can be either insulators or conductive oligomers) may be basically the same length as the monolayer forming species or longer than them, resulting in the nucleic acids being more accessible to the solvent for hybridization. In some embodiments, the conductive oligomers to which the capture binding ligands are attached may be shorter than the monolayer.

As will be appreciated by those in the art, the actual combinations and ratios of the different species making up the monolayer can vary widely. Generally, three component systems are preferred, with the first species comprising a capture binding ligand containing species (i.e. a capture probe, that can be attached to the electrode via either an insulator or a conductive oligomer, as is more fully described below). The second species are the conductive oligomers, and the third species are insulators. In this embodiment, the first species can comprise from about 90% to about 1%, with from about 20% to about 40% being preferred. When the capture binding ligands are nucleic acids and the target is nucleic acid as well, from about 30% to about 40% is especially preferred for short oligonucleotide targets and from about 10% to about 20% is preferred for longer targets. The second species can comprise from about 1% to about 90%, with from about 20% to about 90% being preferred, and from about 40% to about 60% being especially preferred. The third species can comprise from about 1% to about 90%, with from about 20% to about 40% being preferred, and from about 15% to about 30% being especially preferred. Preferred ratios of first:second:third species are 2:2:1 for short targets, 1:3:1 for longer targets, with total thiol concentration in the 500 $\mu$M to 1 mM range, and 833 $\mu$M being preferred.

In a preferred embodiment, two component systems are used, comprising the first and second species. In this embodiment, the first species can comprise from about 90% to about 1%, with from about 1% to about 40% being preferred, and from about 10% to about 40% being especially preferred. The second species can comprise from about 1% to about 90%, with from about 10% to about 60% being preferred, and from about 20% to about 40% being especially preferred.

The covalent attachment of the conductive oligomers and insulators may be accomplished in a variety of ways, depending on the electrode and the composition of the insulators and conductive oligomers used. In a preferred embodiment, the attachment linkers with covalently attached capture binding ligands as depicted herein are covalently attached to an electrode. Thus, one end or terminus of the attachment linker is attached to the capture binding ligand, and the other is attached to an electrode. In some embodiments it may be desirable to have the attachment linker attached at a position other than a terminus, or even to have a branched attachment linker that is attached to an electrode at one terminus and to two or more capture binding ligands at other termini, although this is not preferred. Similarly, the attachment linker may be attached at two sites to the electrode, as is generally depicted in Structures 11–13. Generally, some type of linker is used, as depicted below as "A" in Structure 10, where "X" is the conductive oligomer, "I" is an insulator and the hatched surface is the electrode:

Structure 10

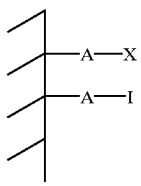

In this embodiment, A is a linker or atom. The choice of "A" will depend in part on the characteristics of the electrode. Thus, for example, A may be a sulfur moiety when a gold electrode is used. Alternatively, when metal oxide electrodes are used, A may be a silicon (silane) moiety attached to the oxygen of the oxide (see for example Chen et al., Langmuir 10:3332–3337 (1994); Lenhard et al., J. Electroanal. Chem. 78:195–201 (1977), both of which are expressly incorporated by reference). When carbon based electrodes are used, A may be an amino moiety (preferably a primary amine; see for example Deinhammer et al., Langmuir 10:1306–1313 (1994)). Thus, preferred A moieties include, but are not limited to, silane moieties, sulfur moieties (including alkyl sulfur moieties), and amino moieties. In a preferred embodiment, epoxide type linkages with redox polymers such as are known in the art are not used.

Although depicted herein as a single moiety, the insulators and conductive oligomers may be attached to the electrode with more than one "A" moiety; the "A" moieties may be the same or different. Thus, for example, when the electrode is a gold electrode, and "A" is a sulfur atom or moiety, multiple sulfur atoms may be used to attach the conductive oligomer to the electrode, such as is generally depicted below in Structures 11, 12 and 13. As will be appreciated by those in the art, other such structures can be made. In Structures 11, 12 and 13, the A moiety is just a sulfur atom, but substituted sulfur moieties may also be used.

Structure 11

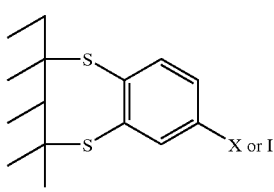

Structure 12

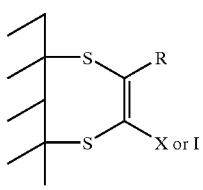

Structure 13

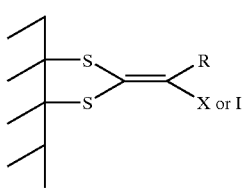

It should also be noted that similar to Structure 13, it may be possible to have a a conductive oligomer terminating in a single carbon atom with three sulfur moieties attached to the electrode. Additionally, although not always depicted herein, the conductive oligomers and insulators may also comprise a "Q" terminal group.

In a preferred embodiment, the electrode is a gold electrode, and attachment is via a sulfur linkage as is well known in the art, i.e. the A moiety is a sulfur atom or moiety. Although the exact characteristics of the gold-sulfur attachment are not known, this linkage is considered covalent for the purposes of this invention. A representative structure is depicted in Structure 14, using the Structure 3 conductive oligomer, although as for all the structures depicted herein, any of the conductive oligomers, or combinations of conductive oligomers, may be used. Similarly, any of the conductive oligomers or insulators may also comprise terminal groups as described herein. Structure 14 depicts the "A" linker as comprising just a sulfur atom, although additional atoms may be present (i.e. linkers from the sulfur to the conductive oligomer or substitution groups).

Structure 14

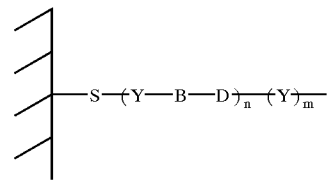

In a preferred embodiment, the electrode is a carbon electrode, i.e. a glassy carbon electrode, and attachment is via a nitrogen of an amine group. A representative structure is depicted in Structure 15. Again, additional atoms may be present, i.e. Z type linkers and/or terminal groups.

Structure 15

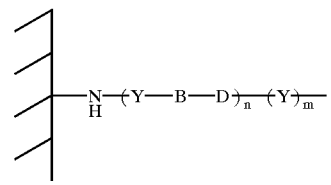

Structure 16

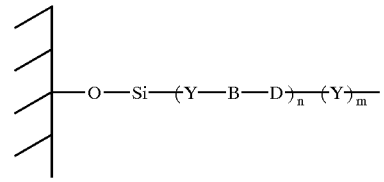

In Structure 16, the oxygen atom is from the oxide of the metal oxide electrode. The Si atom may also contain other atoms, i.e. be a silicon moiety containing substitution groups.

In a preferred embodiment, the electrode comprising the monolayer including conductive oligomers further comprises a capture binding ligand. By "capture binding ligand" or "capture binding species" or "capture probe" herein is meant a compound that is used to probe for the presence of the target analyte, that will bind to the target analyte. Generally, the capture binding ligand allows the attachment of a target analyte to the electrode, for the purposes of detection. As is more fully outlined below, attachment of the target analyte to the capture probe may be direct (i.e. the target analyte binds to the capture binding ligand) or indirect (one or more capture extender ligands are used). By "covalently attached" herein is meant that two moieties are attached by at least one bond, including sigma bonds, pi bonds and coordination bonds.

In a preferred embodiment, the binding is specific, and the binding ligand is part of a binding pair. By "specifically bind" herein is meant that the ligand binds the analyte, with specificity sufficient to differentiate between the analyte and other components or contaminants of the test sample. However, as will be appreciated by those in the art, it will be possible to detect analytes using binding which is not highly specific; for example, the systems may use different binding ligands, for example an array of different ligands, and detection of any particular analyte is via its "signature" of binding to a panel of binding ligands, similar to the manner in which "electronic noses" work. This finds particular utility in the detection of chemical analytes. The binding should be sufficient to remain bound under the conditions of the assay, including wash steps to remove non-specific binding. In some embodiments, for example in the detection of certain biomolecules, the binding constants of the analyte to the binding ligand will be at least about 104–106 M-1, with at least about 105 to 109 M-1 being preferred and at least about 107–109 M-1 being particularly preferred.

As will be appreciated by those in the art, the composition of the binding ligand will depend on the composition of the target analyte. Binding ligands to a wide variety of analytes are known or can be readily found using known techniques. For example, when the analyte is a single-stranded nucleic acid, the binding ligand may be a complementary nucleic acid. Similarly, the analyte may be a nucleic acid binding protein and the capture binding ligand is either single-stranded or double stranded nucleic acid; alternatively, the binding ligand may be a nucleic acid-binding protein when the analyte is a single or double-stranded nucleic acid. When the analyte is a protein, the binding ligands include proteins or small molecules. Preferred binding ligand proteins include peptides. For example, when the analyte is an enzyme, suitable binding ligands include substrates and inhibitors. As will be appreciated by those in the art, any two molecules that will associate may be used, either as an analyte or as the binding ligand. Suitable analyte/binding ligand pairs include, but are not limited to, antibodies/antigens, receptors/ligands, proteins/nucleic acid, enzymes/substrates and/or inhibitors, carbohydrates (including glycoproteins and glycolipids)/lectins, proteins/proteins, proteins/small molecules; and carbohydrates and their binding partners are also suitable analyte-binding ligand pairs. These may be wild-type or derivative sequences. In a preferred embodiment, the binding ligands are portions (particularly the extracellular portions) of cell surface receptors that are known to multimerize, such as the growth hormone receptor, glucose transporters (particularly GLUT 4 receptor), transferrin receptor, epidermal growth factor receptor, low density lipoprotein receptor, high density lipoprotein receptor, epidermal growth factor receptor, leptin receptor, interleukin receptors including IL-1, IL-2, IL-3, IL4, IL-5, IL-6, IL-7, IL-8, IL-9, IL-11, IL-12, IL-13, IL-15, and IL-17 receptors, human growth hormone receptor, VEGF receptor, PDGF receptor, EPO receptor, TPO receptor, ciliary neurotrophic factor receptor, prolactin receptor, and T-cell receptors.

The method of attachment of the capture binding ligand to the attachment linker will generally be done as is known in the art, and will depend on the composition of the attachment linker and the capture binding ligand. In general, the capture binding ligands are attached to the attachment linker through the use of functional groups on each that can then be used for attachment. Preferred functional groups for attachment are amino groups, carboxy groups, oxo groups and thiol groups. These functional groups can then be attached, either directly or through the use of a linker, sometimes depicted herein as "Z". Linkers are known in the art; for example, homo-or hetero-bifunctional linkers as are well known (see 1994 Pierce Chemical Company catalog, technical section on cross-linkers, pages 155–200, incorporated herein by reference). Preferred Z linkers include, but are not limited to, alkyl groups (including substituted alkyl groups and alkyl groups containing heteroatom moieties), with short alkyl groups, esters, amide, amine, epoxy groups and ethylene glycol and derivatives being preferred. Z may also be a sulfone group, forming sulfonamide.

In this way, capture binding ligands comprising proteins, lectins, nucleic acids, small organic molecules, carbohydrates, etc. can be added.

In a preferred embodiment, the capture binding ligand is attached directly to the electrode as outlined herein, for example via an attachment linker. Alternatively, the capture binding ligand may utilize a capture extender component, such as depicted in FIG. 2C. In this embodiment, the capture binding ligand comprises a first portion that will bind the target analyte and a second portion that can be used for attachment to the surface. FIG. 2C depicts the use of a nucleic acid component for binding to the surface, although this can be other binding partners as well.

A preferred embodiment utilizes proteinaceous capture binding ligands. As is known in the art, any number of techniques may be used to attach a proteinaceous capture binding ligand. "Protein" in this context includes proteins, polypeptides and peptides. A wide variety of techniques are known to add moieties to proteins. One preferred method is outlined in U.S. Pat. No. 5,620,850, hereby incorporated by reference in its entirety. The attachment of proteins to electrodes is known; see also Heller, Acc. Chem. Res. 23:128 (1990), and related work.

A preferred embodiment utilizes nucleic acids as the capture binding ligand, for example for when the target analyte is a nucleic acid or a nucleic acid binding protein, or when the nucleic acid serves as an aptamer for binding a protein; see U.S. Pat. Nos. 5,270,163, 5,475,096, 5,567,588, 5,595,877, 5,637,459, 5,683,867, 5,705,337, and related patents, hereby incorporated by reference. In this embodiment, the nucleic acid capture binding ligand is covalently attached to the electrode, via an "attachment linker", that can be either a conductive oligomer or via an insulator. Thus, one end of the attachment linker is attached to a nucleic acid, and the other end (although as will be appreciated by those in the art, it need not be the exact terminus for either) is attached to the electrode. Thus, any of structures 1–16 may further comprise a nucleic acid effectively as a terminal group. Thus, the present invention provides compositions comprising binding ligands covalently attached to electrodes as is generally depicted below in Structure 17 for a nucleic acid:

Structure 17

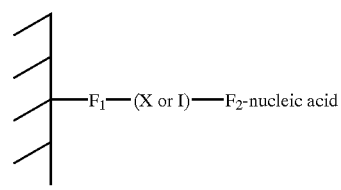

In Structure 17, the hatched marks on the left represent an electrode. X is a conductive oligomer and I is an insulator as defined herein. $F_1$ is a linkage that allows the covalent attachment of the electrode and the conductive oligomer or insulator, including bonds, atoms or linkers such as is described herein, for example as "A", defined below. $F_2$ is a linkage that allows the covalent attachment of the conductive oligomer or insulator to the binding ligand, a nucleic acid in Structure 17, and may be a bond, an atom or a linkage as is herein described. $F_2$ may be part of the conductive oligomer, part of the insulator, part of the binding ligand, or exogeneous to both, for example, as defined herein for "Z".

In general, the methods, synthetic schemes and compositions useful for the attachment of capture binding ligands, particularly nucleic acids, are outlined in WO98/20162, PCT US98/12430, PCT US98/12082; PCT US99/01705 and PCT US99/01703, all of which are expressly incorporated herein by reference in their entirety.

In a preferred embodiment, the capture binding ligand is covalently attached to the electrode via a conductive oligomer. The covalent attachment of the binding ligand and the conductive oligomer may be accomplished in several ways, as will be appreciated by those in the art.

In a preferred embodiment, the capture binding ligand is a nucleic acid, and the attachment is via attachment to the base of the nucleoside, via attachment to the backbone of the nucleic acid (either the ribose, the phosphate, or to an analogous group of a nucleic acid analog backbone), or via a transition metal ligand, as described below. The techniques outlined below are generally described for naturally occurring nucleic acids, although as will be appreciated by those in the art, similar techniques may be used with nucleic acid analogs.

In a preferred embodiment, the conductive oligomer is attached to the base of a nucleoside of the nucleic acid. This may be done in several ways, depending on the oligomer, as is described below. In one embodiment, the oligomer is attached to a terminal nucleoside, i.e. either the 3' or 5' nucleoside of the nucleic acid. Alternatively, the conductive oligomer is attached to an internal nucleoside.

The point of attachment to the base will vary with the base. Generally, attachment at any position is possible. In some embodiments, for example when the probe containing the ETMs may be used for hybridization, it is preferred to attach at positions not involved in hydrogen bonding to the complementary base. Thus, for example, generally attachment is to the 5 or 6 position of pyrimidines such as uridine, cytosine and thymine. For purines such as adenine and guanine, the linkage is preferably via the 8 position. Attachment to non-standard bases is preferably done at the comparable positions.

In one embodiment, the attachment is direct; that is, there are no intervening atoms between the conductive oligomer and the base. In this embodiment, for example, conductive oligomers with terminal acetylene bonds are attached directly to the base. Structure 18 is an example of this linkage, using a Structure 3 conductive oligomer and uridine as the base, although other bases and conductive oligomers can be used as will be appreciated by those in the art:

Structure 18

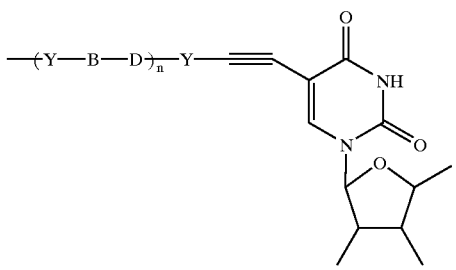

It should be noted that the pentose structures depicted herein may have hydrogen, hydroxy, phosphates or other groups such as amino groups attached. In addition, the pentose and nucleoside structures depicted herein are depicted non-conventionally, as mirror images of the normal rendering. In addition, the pentose and nucleoside structures may also contain additional groups, such as protecting groups, at any position, for example as needed during synthesis.

In addition, the base may contain additional modifications as needed, i.e. the carbonyl or amine groups may be altered or protected.

In an alternative embodiment, the attachment is any number of different Z linkers, including amide and amine linkages, as is generally depicted in Structure 19 using uridine as the base and a Structure 3 oligomer:

Structure 19

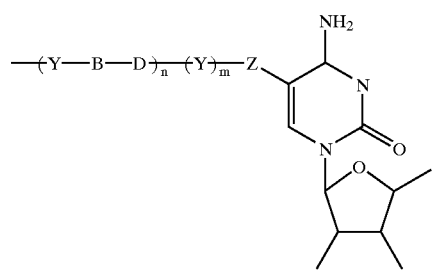

In this embodiment, Z is a linker. Preferably, Z is a short linker of about 1 to about 10 atoms, with from 1 to 5 atoms being preferred, that may or may not contain alkene, alkynyl, amine, amide, azo, imine, etc., bonds. Linkers are known in the art; for example, homo-or hetero-bifunctional linkers as are well known (see 1994 Pierce Chemical Company catalog, technical section on cross-linkers, pages 155–200, incorporated herein by reference). Preferred Z linkers include, but are not limited to, alkyl groups (including substituted alkyl groups and alkyl groups containing heteroatom moieties), with short alkyl groups, esters, amide, amine, epoxy groups and ethylene glycol and derivatives being preferred, with propyl, acetylene, and $C_2$ alkene being especially preferred. Z may also be a sulfone group, forming sulfonamide linkages as discussed below.

In a preferred embodiment, the attachment of the nucleic acid and the conductive oligomer is done via attachment to the backbone of the nucleic acid. This may be done in a number of ways, including attachment to a ribose of the ribose-phosphate backbone, or to the phosphate of the backbone, or other groups of analogous backbones.

As a preliminary matter, it should be understood that the site of attachment in this embodiment may be to a 3' or 5' terminal nucleotide, or to an internal nucleotide, as is more fully described below.

In a preferred embodiment, the conductive oligomer is attached to the ribose of the ribose-phosphate backbone. This may be done in several ways. As is known in the art, nucleosides that are modified at either the 2' or 3' position of the ribose with amino groups, sulfur groups, silicone groups, phosphorus groups, or oxo groups can be made (Imazawa et al., J. Org. Chem., 44:2039 (1979); Hobbs et al., J. Org. Chem. 42(4):714 (1977); Verheyden et al., J. Orrg. Chem. 36(2):250 (1971); McGee et al., J. Org. Chem. 61:781–785 (1996); Mikhailopulo et al., Liebigs. Ann. Chem. 513–519 (1993); McGee et al., Nucleosides & Nucleotides 14(6):1329 (1995), all of which are incorporated by reference). These modified nucleosides are then used to add the conductive oligomers.

A preferred embodiment utilizes amino-modified nucleosides. These amino-modified riboses can then be used to form either amide or amine linkages to the conductive oligomers. In a preferred embodiment, the amino group is attached directly to the ribose, although as will be appreciated by those in the art, short linkers such as those described herein for "Z" may be present between the amino group and the ribose.

In a preferred embodiment, an amide linkage is used for attachment to the ribose. Preferably, if the conductive oligomer of Structures 1–3 is used, m is zero and thus the conductive oligomer terminates in the amide bond. In this embodiment, the nitrogen of the amino group of the amino-modified ribose is the "D" atom of the conductive oligomer. Thus, a preferred attachment of this embodiment is depicted in Structure 20 (using the Structure 3 conductive oligomer):

Structure 20

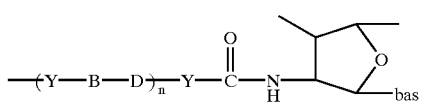

As will be appreciated by those in the art, Structure 20 has the terminal bond fixed as an amide bond.

In a preferred embodiment, a heteroatom linkage is used, i.e. oxo, amine, sulfur, etc. A preferred embodiment utilizes an amine linkage. Again, as outlined above for the amide linkages, for amine linkages, the nitrogen of the amino-modified ribose may be the "D" atom of the conductive oligomer when the Structure 3 conductive oligomer is used. Thus, for example, Structures 21 and 22 depict nucleosides with the Structures 3 and 9 conductive oligomers, respectively, using the nitrogen as the heteroatom, athough other heteroatoms can be used:

Structure 21

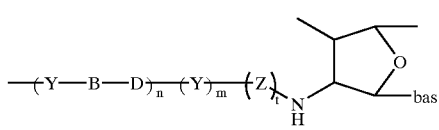

In Structure 21, preferably both m and t are not zero. A preferred Z here is a methylene group, or other aliphatic alkyl linkers. One, two or three carbons in this position are particularly useful for synthetic reasons.

Structure 22

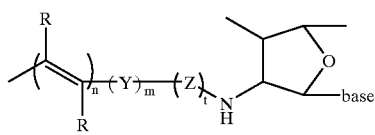

In Structure 22, Z is as defined above. Suitable linkers include methylene and ethylene.

In an alternative embodiment, the conductive oligomer is covalently attached to the nucleic acid via the phosphate of the ribose-phosphate backbone (or analog) of a nucleic acid. In this embodiment, the attachment is direct, utilizes a linker or via an amide bond. Structure 23 depicts a direct linkage, and Structure 24 depicts linkage via an amide bond (both utilize the Structure 3 conductive oligomer, although Structure 8 conductive oligomers are also possible). Structures 23 and 24 depict the conductive oligomer in the 3' position, although the 5' position is also possible. Furthermore, both Structures 23 and 24 depict naturally occurring phosphodiester bonds, although as those in the art will appreciate, non-standard analogs of phosphodiester bonds may also be used.

Structure 23

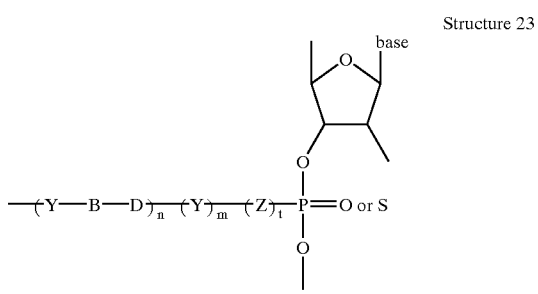

In Structure 23, if the terminal Y is present (i.e. m=1), then preferably Z is not present (i.e. t=0). If the terminal Y is not present, then Z is preferably present.

Structure 24 depicts a preferred embodiment, wherein the terminal B—D bond is an amide bond, the terminal Y is not present, and Z is a linker, as defined herein.

Structure 24

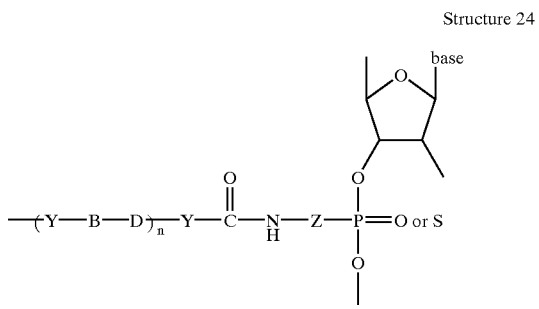

In a preferred embodiment, the conductive oligomer is covalently attached to the nucleic acid via a transition metal ligand. In this embodiment, the conductive oligomer is covalently attached to a ligand which provides one or more of the coordination atoms for a transition metal. In one embodiment, the ligand to which the conductive oligomer is attached also has the nucleic acid attached, as is generally depicted below in Structure 25. Alternatively, the conductive oligomer is attached to one ligand, and the nucleic acid is attached to another ligand, as is generally depicted below in Structure 26. Thus, in the presence of the transition metal, the conductive oligomer is covalently attached to the nucleic acid. Both of these structures depict Structure 3 conductive oligomers, although other oligomers may be utilized. Structures 25 and 26 depict two representative structures for nucleic acids; as will be appreciated by those in the art, it is possible to connect other types of capture binding ligands, for example proteinaceous binding ligands, in a similar manner:

Structure 25

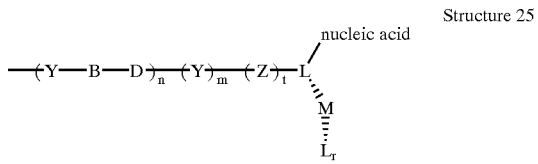

Structure 26

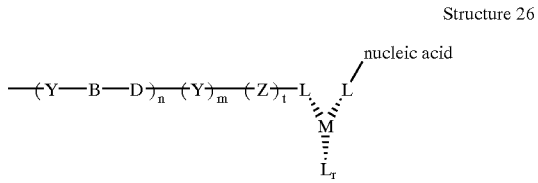

In the structures depicted herein, M is a metal atom, with transition metals being preferred. Suitable transition metals for use in the invention include, but are not limited to, cadmium (Cd), copper (Cu), cobalt (Co), palladium (Pd), zinc (Zn), iron (Fe), ruthenium (Ru), rhodium (Rh), osmium (Os), rhenium (Re), platinium (Pt), scandium (Sc), titanium (Ti), Vanadium (V), chromium (Cr), manganese (Mn), nickel (Ni), Molybdenum (Mo), technetium (Tc), tungsten (W), and iridium (Ir). That is, the first series of transition metals, the platinum metals (Ru, Rh, Pd, Os, Ir and Pt), along with Fe, Re, W, Mo and Tc, are preferred. Particularly preferred are ruthenium, rhenium, osmium, platinium, cobalt and iron. L are the co-ligands, that provide the coordination atoms for the binding of the metal ion. As will be appreciated by those in the art, the number and nature of the co-ligands will depend on the coordination number of the metal ion. Mono-, di- or polydentate co-ligands may be used at any position. Thus, for example, when the metal has a coordination number of six, the L from the terminus of the conductive oligomer, the L contributed from the nucleic acid, and r, add up to six. Thus, when the metal has a coordination number of six, r may range from zero (when all coordination atoms are provided by the other two ligands) to four, when all the co-ligands are monodentate. Thus generally, r will be from 0 to 8, depending on the coordination number of the metal ion and the choice of the other ligands.

In one embodiment, the metal ion has a coordination number of six and both the ligand attached to the conductive oligomer and the ligand attached to the nucleic acid are at least bidentate; that is, r is preferably zero, one (i.e. the remaining co-ligand is bidentate) or two (two monodentate co-ligands are used).

As will be appreciated in the art, the co-ligands can be the same or different. Suitable ligands fall into two categories: ligands which use nitrogen, oxygen, sulfur, carbon or phosphorus atoms (depending on the metal ion) as the coordination atoms (generally referred to in the literature as sigma (σ) donors) and organometallic ligands such as metallocene ligands (generally referred to in the literature as pi (π) donors, and depicted herein as $L_m$). Suitable nitrogen donating ligands are well known in the art and include, but are not limited to, $NH_2$; NHR; NRR'; pyridine; pyrazine; isonicotinamide; imidazole; bipyridine and substituted derivatives of bipyridine; terpyridine and substituted derivatives; phenanthrolines, particularly 1,10-phenanthroline (abbreviated phen) and substituted derivatives of phenanthrolines such as 4,7-dimethylphenanthroline and dipyridol [3,2-a:2',3'-c]phenazine (abbreviated dppz); dipyridophenazine; 1,4,5,8,9,12-hexaazatriphenylene (abbreviated hat); 9,10-phenanthrenequinone diimine (abbreviated phi); 1,4,5,8-tetraazaphenanthrene (abbreviated tap); 1,4,8,11-tetra-azacyclotetradecane (abbreviated cyclam), EDTA, EGTA and isocyanide. Substituted derivatives, including fused derivatives, may also be used. In some embodiments, porphyrins and substituted derivatives of the porphyrin family may be used. See for example, Comprehensive Coordination Chemistry, Ed. Wilkinson et al., Pergammon Press, 1987, Chapters 13.2 (pp73–98), 21.1 (pp. 813–898) and 21.3 (pp 915–957), all of which are hereby expressly incorporated by reference.

Suitable sigma donating ligands using carbon, oxygen, sulfur and phosphorus are known in the art. For example, suitable sigma carbon donors are found in Cotton and Wilkenson, Advanced Organic Chemistry, 5th Edition; John Wiley & Sons, 1988, hereby incorporated by reference; see page 38, for example. Similarly, suitable oxygen ligands include crown ethers, water and others known in the art. Phosphines and substituted phosphines are also suitable; see page 38 of Cotton and Wilkenson.

The oxygen, sulfur, phosphorus and nitrogen-donating ligands are attached in such a manner as to allow the heteroatoms to serve as coordination atoms.

In a preferred embodiment, organometallic ligands are used. In addition to purely organic compounds for use as redox moieties, and various transition metal coordination complexes with δ-bonded organic ligand with donor atoms as heterocyclic or exocyclic substituents, there is available a wide variety of transition metal organometallic compounds with π-bonded organic ligands (see Advanced Inorganic Chemistry, 5th Ed., Cotton & Wilkinson, John Wiley & Sons, 1988, chapter 26; Organometallics, A Concise Introduction, Elschenbroich et al., 2nd Ed., 1992, VCH; and Comprehensive Organometallic Chemistry II, A Review of the Literature 1982–1994, Abel et al. Ed., Vol. 7, chapters 7, 8, 10 & 11, Pergamon Press, hereby expressly incorporated by reference). Such organometallic ligands include cyclic aromatic compounds such as the cyclopentadienide ion $[C_5H_5(-1)]$ and various ring substituted and ring fused derivatives, such as the indenylide (−1) ion, that yield a class of bis(cyclopentadieyl) metal compounds, (i.e. the metallocenes); see for example Robins et al., J. Am. Chem. Soc. 104:1882–1893 (1982); and Gassman et al., J. Am. Chem. Soc. 108:4228–4229 (1986), incorporated by reference. Of these, ferrocene $[(C_5H_5)_2Fe]$ and its derivatives are prototypical examples which have been used in a wide variety of chemical (Connelly et al., Chem. Rev. 96:877–910 (1996), incorporated by reference) and electrochemical (Geiger et al., Advances in Organometallic Chemistry 23:1–93; and Geiger et al., Advances in Organometallic Chemistry 24:87, incorporated by reference) electron transfer or "redox" reactions. Metallocene derivatives of a variety of the first, second and third row transition metals are potential candidates as redox moieties that are covalently attached to either the ribose ring or the nucleoside base of nucleic acid. Other potentially suitable organometallic ligands include cyclic arenes such as benzene, to yield bis(arene)metal compounds and their ring substituted and ring fused derivatives, of which bis(benzene)chromium is a prototypical example, Other acyclic π-bonded ligands such as the allyl(−1) ion, or butadiene yield potentially suitable organometallic compounds, and all such ligands, in conjuction with other π-bonded and δ-bonded ligands constitute the general class of organometallic compounds in which there is a metal to carbon bond. Electrochemical studies of various dimers and oligomers of such compounds with bridging organic ligands, and additional non-bridging ligands, as well as with and without metal-metal bonds are potential candidate redox moieties in nucleic acid analysis.

When one or more of the co-ligands is an organometallic ligand, the ligand is generally attached via one of the carbon atoms of the organometallic ligand, although attachment may be via other atoms for heterocyclic ligands. Preferred organometallic ligands include metallocene ligands, including substituted derivatives and the metalloceneophanes (see page 1174 of Cotton and Wilkenson, supra). For example, derivatives of metallocene ligands such as methylcyclopentadienyl, with multiple methyl groups being preferred, such as pentamethylcyclopentadienyl, can be used to increase the stability of the metallocene. In a preferred embodiment, only one of the two metallocene ligands of a metallocene are derivatized.

As described herein, any combination of ligands may be used. Preferred combinations include: a) all ligands are nitrogen donating ligands; b) all ligands are organometallic ligands; and c) the ligand at the terminus of the conductive oligomer is a metallocene ligand and the ligand provided by the nucleic acid is a nitrogen donating ligand, with the other ligands, if needed, are either nitrogen donating ligands or metallocene ligands, or a mixture. These combinations are depicted in representative structures using the conductive oligomer of Structure 3 are depicted in Structures 27 (using phenanthroline and amino as representative ligands), 28 (using ferrocene as the metal-ligand combination) and 29 (using cyclopentadienyl and amino as representative ligands).

Structure 27

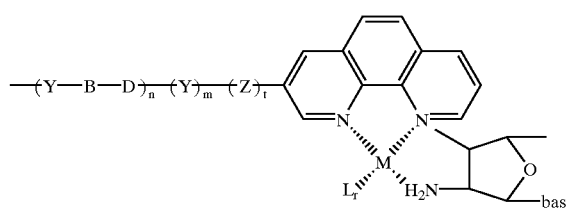

Structure 28

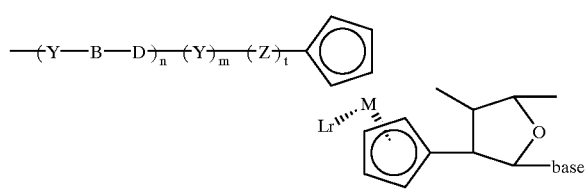

Structure 29

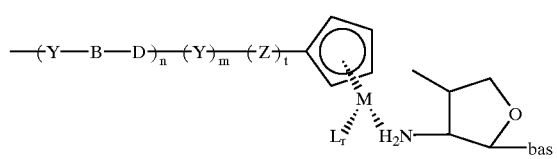

In a preferred embodiment, the ligands used in the invention show altered fluoroscent properties depending on the redox state of the chelated metal ion. As described below, this thus serves as an additional mode of detection of electron transfer between the ETM and the electrode.

In a preferred embodiment, as is described more fully below, the ligand attached to the nucleic acid is an amino group attached to the 2' or 3' position of a ribose of the ribose-phosphate backbone. This ligand may contain a multiplicity of amino groups so as to form a polydentate ligand which binds the metal ion. Other preferred ligands include cyclopentadiene and phenanthroline.

The use of metal ions to connect the binding ligands such as nucleic acids can serve as an internal control or calibration of the system, to evaluate the number of available binding ligands on the surface. However, as will be appreciated by those in the art, if metal ions are used to connect the binding ligands such as nucleic acids to the conductive oligomers, it is generally desirable to have this metal ion complex have a different redox potential than that of the ETMs used in the rest of the system, as described below. This is generally true so as to be able to distinguish the presence of the capture probe from the presence of the target analyte. This may be useful for identification, calibration and/or quantification. Thus, the amount of capture probe on an electrode may be compared to the amount of target analyte to quantify the amount of target sequence in a sample. This is quite significant to serve as an internal control of the sensor or system. This allows a measurement either prior to the addition of target or after, on the same molecules that will be used for detection, rather than rely on a similar but different control system. Thus, the actual molecules that will be used for the detection can be quantified prior to any experiment. This is a significant advantage over prior methods.

In a preferred embodiment, the capture binding ligands are covalently attached to the electrode via an insulator. The attachment of a variety of binding ligands such as proteins and nucleic acids to insulators such as alkyl groups is well known, and can be done to the nucleic acid bases or the backbone, including the ribose or phosphate for backbones containing these moieties, or to alternate backbones for nucleic acid analogs, or to the side chains or backbone of the amino acids.

In a preferred embodiment, there may be one or more different capture binding ligand species (sometimes referred to herein as "anchor ligands", "anchor probes" or "capture probes" with the phrase "probe" generally referring to nucleic acid species) on the surface, as is generally depicted in the Figures. In some embodiments, there may be one type of capture binding ligand, or one type of capture binding ligand extender, as is more fully described below. Alternatively, different capture binding ligands, or one capture binding ligand with a multiplicity of different capture extender binding ligands can be used. Similarly, when nucleic acid systems are used, it may be desirable to use auxiliary capture probes that comprise relatively short probe sequences, that can be used to "tack down" components of the system, for example the recruitment linkers, to increase the concentration of ETMs at the surface.

Thus the present invention provides electrodes comprising monolayers comprising conductive oligomers and capture binding ligands, useful in target analyte detection systems.

In a preferred embodiment, the compositions further comprise a solution binding ligand. Solution binding ligands are similar to capture binding ligands, in that they bind to target analytes. The solution binding ligand may be the same or different from the capture binding ligand. Generally, the solution binding ligands are not directly attached to the surface, although as depicted in FIG. 5A they may be. The solution binding ligand either directly comprises a recruitment linker that comprises at least one ETM, or the recruitment linker is part of a label probe that will bind to the solution binding ligand.

Thus, "recruitment linkers" or "signal carriers" with covalently attached ETMs are provided. The terms "electron donor moiety", "electron acceptor moiety", and "ETMs" (ETMs) or grammatical equivalents herein refers to molecules capable of electron transfer under certain conditions. It is to be understood that electron donor and acceptor capabilities are relative; that is, a molecule which can lose an electron under certain experimental conditions will be able to accept an electron under different experimental conditions. It is to be understood that the number of possible electron donor moieties and electron acceptor moieties is very large, and that one skilled in the art of electron transfer compounds will be able to utilize a number of compounds in the present invention. Preferred ETMs include, but are not limited to, transition metal complexes, organic ETMs, and electrodes.

In a preferred embodiment, the ETMs are transition metal complexes. Transition metals are those whose atoms have a partial or complete d shell of electrons. Suitable transition metals for use in the invention are listed above.

The transition metals are complexed with a variety of ligands, L, defined above, to form suitable transition metal complexes, as is well known in the art.

In addition to transition metal complexes, other organic electron donors and acceptors may be covalently attached to the nucleic acid for use in the invention. These organic molecules include, but are not limited to, riboflavin, xanthene dyes, azine dyes, acridine orange, N,N'-dimethyl-2,7-diazapyrenium dichloride ($DAP^{2+}$), methylviologen, ethidium bromide, quinones such as N,N'-dimethylanthra(2,1,9-def6,5,10-d'e'f')diisoquinoline dichloride ($ADIQ^{2+}$); porphyrins ([meso-tetrakis(N-methyl-x-pyridinium) porphyrin tetrachloride], varlamine blue B hydrochloride, Bindschedler's green; 2,6-dichloroindophenol, 2,6-dibromophenolindophenol; Brilliant crest blue (3-amino-9-dimethyl-amino-10-methylphenoxyazine chloride), methylene blue; Nile blue A (aminoaphthodiethylaminophenoxazine sulfate), indigo-5,5',7,7'-tetrasulfonic acid, indigo-5,5',7-trisulfonic acid; phenosafranine, indigo-5-monosulfonic acid; safranine T; bis(dimethylglyoximato)-iron(II) chloride; induline scarlet, neutral red, anthracene, coronene, pyrene, 9-phenylanthracene, rubrene, binaphthyl, DPA, phenothiazene, fluoranthene, phenanthrene, chrysene, 1,8-diphenyl-1,3,5,7-octatetracene, naphthalene, acenaphthalene, perylene, TMPD and analogs and subsitituted derivatives of these compounds.

In one embodiment, the electron donors and acceptors are redox proteins as are known in the art. However, redox proteins in many embodiments are not preferred.

The choice of the specific ETMs will be influenced by the type of electron transfer detection used, as is generally outlined below. Preferred ETMs are metallocenes, with ferrocene being particularly preferred.

In a preferred embodiment, a plurality of ETMs are used. As is shown in the examples, the use of multiple ETMs provides signal amplification and thus allows more sensitive detection limits. Accordingly, pluralities of ETMs are preferred, with at least about 2 ETMs per recruitment linker being preferred, and at least about 10 being particularly preferred, and at least about 20 to 50 being especially preferred. In some instances, very large numbers of ETMs (100 to 1000) can be used.

As will be appreciated by those in the art, the portion of the label probe (or target, in some embodiments) that comprises the ETMs (termed herein a "recruitment linker" or "signal carrier") can be nucleic acid, or it can be a non-nucleic acid linker that links the solution binding ligand to the ETMs. Thus, as will be appreciated by those in the art, there are a variety of configurations that can be used. In a preferred embodiment, the recruitment linker is nucleic acid (including analogs), and attachment of the ETMs can be via (1) a base; (2) the backbone, including the ribose, the phosphate, or comparable structures in nucleic acid analogs; (3) nucleoside replacement, described below; or (4) metallocene polymers, as described below. In a preferred embodiment, the recruitment linker is non-nucleic acid, and can be either a metallocene polymer or an alkyl-type polymer (including heteroalkyl, as is more fully described below) containing ETM substitution groups. These options are generally depicted in FIGS. 14A–14K, 15A–15O and 21A–E.

In a preferred embodiment, the recruitment linker is a nucleic acid, and comprises covalently attached ETMs. The ETMs may be attached to nucleosides within the nucleic acid in a variety of positions. Preferred embodiments include, but are not limited to, (1) attachment to the base of the nucleoside, (2) attachment of the ETM as a base replacement, (3) attachment to the backbone of the nucleic acid, including either to a ribose of the ribose-phosphate backbone or to a phosphate moiety, or to analogous structures in nucleic acid analogs, and (4) attachment via metallocene polymers, with the latter being preferred.

In addition, as is described below, when the recruitment linker is nucleic acid, it may be desirable to use secondary label probes, that have a first portion that will hybridize to a portion of the primary label probes and a second portion comprising a recruitment linker as is defined herein. This is generally depicted in FIGS. 3A–3H; this is similar to the use of an amplifier probe, except that both the primary and the secondary label probes comprise ETMs.

In a preferred embodiment, the ETM is attached to the base of a nucleoside as is generally outlined above for attachment of the conductive oligomer. Attachment can be to an internal nucleoside or a terminal nucleoside.

The covalent attachment to the base will depend in part on the ETM chosen, but in general is similar to the attachment of conductive oligomers to bases, as outlined above. Attachment may generally be done to any position of the base. In a preferred embodiment, the ETM is a transition metal complex, and thus attachment of a suitable metal ligand to the base leads to the covalent attachment of the ETM. Alternatively, similar types of linkages may be used for the attachment of organic ETMs, as will be appreciated by those in the art.

In one embodiment, the C4 attached amino group of cytosine, the C6 attached amino group of adenine, or the C2 attached amino group of guanine may be used as a transition metal ligand.

Ligands containing aromatic groups can be attached via acetylene linkages as is known in the art (see Comprehensive Organic Synthesis, Trost et al., Ed., Pergamon Press, Chapter 2.4: Coupling Reactions Between $sp^2$ and sp Carbon Centers, Sonogashira, pp521–549, and pp950–953, hereby incorporated by reference). Structure 30 depicts a representative structure in the presence of the metal ion and any other necessary ligands; Structure 30 depicts uridine, although as for all the structures herein, any other base may also be used.

Structure 30

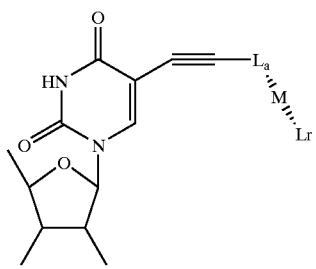

$L_a$ is a ligand, which may include nitrogen, oxygen, sulfur or phosphorus donating ligands or organometallic ligands such as metallocene ligands. Suitable $L_a$ ligands include, but not limited to, phenanthroline, imidazole, bpy and terpy. $L_r$ and M are as defined above. Again, it will be appreciated by those in the art, a linker ("Z") may be included between the nucleoside and the ETM.

Similarly, as for the conductive oligomers, the linkage may be done using a linker, which may utilize an amide linkage (see generally Telser et al., J. Am. Chem. Soc. 111:7221–7226 (1989); Telser et al., J. Am. Chem. Soc. 111:7226–7232 (1989), both of which are expressly incorporated by reference). These structures are generally depicted below in Structure 31, which again uses uridine as the base, although as above, the other bases may also be used:

Structure 31

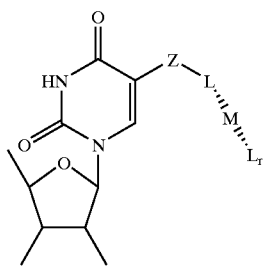

In this embodiment, L is a ligand as defined above, with $L_r$ and M as defined above as well. Preferably, L is amino, phen, byp and terpy.

In a preferred embodiment, the ETM attached to a nucleoside is a metallocene; i.e. the L and $L_r$ of Structure 31 are both metallocene ligands, $L_m$, as described above. Structure 32 depicts a preferred embodiment wherein the metallocene is ferrocene, and the base is uridine, although other bases may be used:

Structure 32

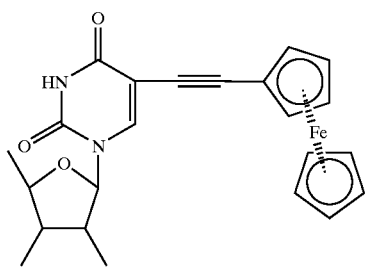

Preliminary data suggest that Structure 32 may cyclize, with the second acetylene carbon atom attacking the carbonyl oxygen, forming a furan-like structure. Preferred metallocenes include ferrocene, cobaltocene and osmiumocene.

In a preferred embodiment, the ETM is attached to a ribose at any position of the ribose-phosphate backbone of the nucleic acid, i.e. either the 5' or 3' terminus or any internal nucleoside. Ribose in this case can include ribose analogs. As is known in the art, nucleosides that are modified at either the 2' or 3' position of the ribose can be made, with nitrogen, oxygen, sulfur and phosphorus-containing modifications possible. Amino-modified and oxygen-modified ribose is preferred. See generally PCT publication WO 95/15971, incorporated herein by reference. These modification groups may be used as a transition metal ligand, or as a chemically functional moiety for attachment of other transition metal ligands and organometallic ligands, or organic electron donor moieties as will be appreciated by those in the art. In this embodiment, a linker such as depicted herein for "Z" may be used as well, or a conductive oligomer between the ribose and the ETM. Preferred embodiments utilize attachment at the 2' or 3' position of the ribose, with the 2' position being preferred. Thus for example, the conductive oligomers depicted in Structure 13, 14 and 15 may be replaced by ETMs; alternatively, the ETMs may be added to the free terminus of the conductive oligomer.

In a preferred embodiment, a metallocene serves as the ETM, and is attached via an amide bond as depicted below in Structure 33. The examples outline the synthesis of a preferred compound when the metallocene is ferrocene.

Structure 33

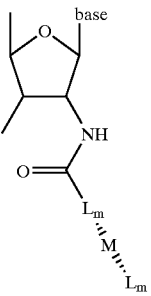

In a preferred embodiment, amine linkages are used, as is generally depicted in Structure 34.

Structure 34

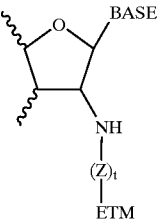

Z is a linker, as defined herein, with 1–16 atoms being preferred, and 2–4 atoms being particularly preferred, and t is either one or zero.

In a preferred embodiment, oxo linkages are used, as is generally depicted in Structure 35.

Structure 35

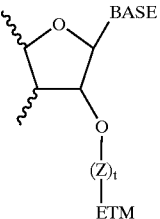

In Structure 35, Z is a linker, as defined herein, and t is either one or zero. Preferred Z linkers include alkyl groups including heteroalkyl groups such as $(CH_2)_n$ and $(CH_2CH_2O)_n$, with n from 1 to 10 being preferred, and n=1 to 4 being especially preferred, and n=4 being particularly preferred.

Linkages utilizing other heteroatoms are also possible.

In a preferred embodiment, an ETM is attached to a phosphate at any position of the ribose-phosphate backbone of the nucleic acid. This may be done in a variety of ways. In one embodiment, phosphodiester bond analogs such as phosphoramide or phosphoramidite linkages may be incorporated into a nucleic acid, where the heteroatom (i.e. nitrogen) serves as a transition metal ligand (see PCT publication WO 95/15971, incorporated by reference). Alternatively, the conductive oligomers depicted in Structures 23 and 24 may be replaced by ETMs. In a preferred embodiment, the composition has the structure shown in Structure 36.

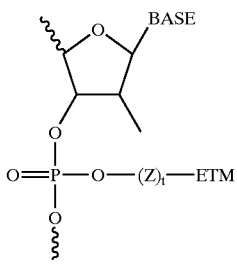

Structure 36

In Structure 361, the ETM is attached via a phosphate linkage, generally through the use of a linker, Z. Preferred Z linkers include alkyl groups, including heteroalkyl groups such as $(CH_2)_n$, $(CH_2CH_2O)_n$, with n from 1 to 10 being preferred, and n=1 to 4 being especially preferred, and n=4 being particularly preferred.

When the ETM is attached to the base or the backbone of the nucleoside, it is possible to attach the ETMs via "dendrimer" structures, as is more fully outlined below. As is generally depicted in FIG. 20, alkyl-based linkers can be used to create multiple branching structures comprising one or more ETMs at the terminus of each branch. Generally, this is done by creating branch points containing multiple hydroxy groups, which optionally can then be used to add additional branch points. The terminal hydroxy groups can then be used in phosphoramidite reactions to add ETMs, as is generally done below for the nucleoside replacement and metallocene polymer reactions.

In a preferred embodiment, an ETM such as a metallocene is used as a "nucleoside replacement", serving as an ETM. For example, the distance between the two cyclopentadiene rings of ferrocene is similar to the orthongonal distance between two bases in a double stranded nucleic acid. Other metallocenes in addition to ferrocene may be used, for example, air stable metallocenes such as those containing cobalt or ruthenium. Thus, metallocene moieties may be incorporated into the backbone of a nucleic acid, as is generally depicted in Structure 37 (nucleic acid with a ribose-phosphate backbone) and Structure 38 (peptide nucleic acid backbone). Structures 37 and 38 depict ferrocene, although as will be appreciated by those in the art, other metallocenes may be used as well. In general, air stable metallocenes are preferred, including metallocenes utilizing ruthenium and cobalt as the metal.

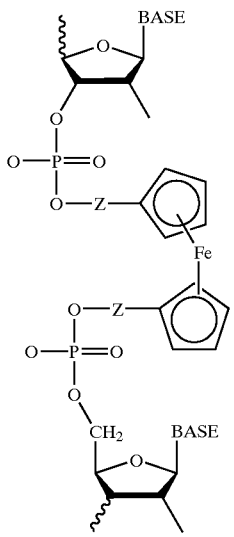

Structure 37

In Structure 37, Z is a linker as defined above, with generally short, alkyl groups, including heteroatoms such as oxygen being preferred. Generally, what is important is the length of the linker, such that minimal perturbations of a double stranded nucleic acid is effected, as is more fully described below. Thus, methylene, ethylene, ethylene glycols, propylene and butylene are all preferred, with ethylene and ethylene glycol being particularly preferred. In addition, each Z linker may be the same or different. Structure 37 depicts a ribose-phosphate backbone, although as will be appreciated by those in the art, nucleic acid analogs may also be used, including ribose analogs and phosphate bond analogs.

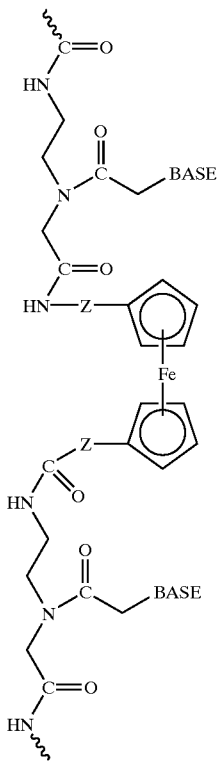

Structure 38

In Structure 38, preferred Z groups are as listed above, and again, each Z linker can be the same or different. As above, other nucleic acid analogs may be used as well.

In addition, although the structures and discussion above depicts metallocenes, and particularly ferrocene, this same general idea can be used to add EfMs in addition to metallocenes, as nucleoside replacements or in polymer embodiments, described below. Thus, for example, when the ETM is a transition metal complex other than a metallocene, comprising one, two or three (or more) ligands, the ligands can be functionalized as depicted for the ferrocene to allow the addition of phosphoramidite groups. Particularly preferred in this embodiment are complexes comprising at least two ring (for example, aryl and substituted aryl) ligands, where each of the ligands comprises functional groups for attachment via phosphoramidite chemistry. As will be appreciated by those in the art, this type of reaction, creating polymers of ETMs either as a portion of the backbone of the nucleic acid or as "side groups" of the nucleic acids, to allow amplification of the signals generated herein, can be done with virtually any ETM that can be functionalized to contain the correct chemical groups.

Thus, by inserting a metallocene such as ferrocene (or other ETM) into the backbone of a nucleic acid, nucleic acid analogs are made; that is, the invention provides nucleic acids having a backbone comprising at least one metallocene. This is distinguished from nucleic acids having metallocenes attached to the backbone, i.e. via a ribose, a phosphate, etc. That is, two nucleic acids each made up of a traditional nucleic acid or analog (nucleic acids in this case including a single nucleoside), may be covalently attached to each other via a metallocene. Viewed differently, a metallocene derivative or substituted metallocene is provided, wherein each of the two aromatic rings of the metallocene has a nucleic acid substitutent group.

In addition, as is more fully outlined below, it is possible to incorporate more than one metallocene into the backbone, either with nucleotides in between and/or with adjacent metallocenes. When adjacent metallocenes are added to the backbone, this is similar to the process described below as "metallocene polymers"; that is, there are areas of metallocene polymers within the backbone.

In addition to the nucleic acid substitutent groups, it is also desirable in some instances to add additional substituent groups to one or both of the aromatic rings of the metallocene (or ETM). For example, as these nucleoside replacements are generally part of probe sequences to be hybridized with a substantially complementary nucleic acid, for example a target sequence or another probe sequence, it is possible to add substitutent groups to the metallocene rings to facilitate hydrogen bonding to the base or bases on the opposite strand. These may be added to any position on the metallocene rings. Suitable substituent groups include, but are not limited to, amide groups, amine groups, carboxylic acids, and alcohols, including substituted alcohols. In addition, these substitutent groups can be attached via linkers as well, although in general this is not preferred.

In addition, substituent groups on an ETM, particularly metallocenes such as ferrocene, may be added to alter the redox properties of the ETM. Thus, for example, in some embodiments, as is more fully described below, it may be desirable to have different ETMs attached in different ways (i.e. base or ribose attachment), on different probes, or for different purposes (for example, calibration or as an internal standard). Thus, the addition of substituent groups on the metallocene may allow two different ETMs to be distinguished.

In order to generate these metallocene-backbone nucleic acid analogs, the intermediate components are also provided. Thus, in a preferred embodiment, the invention provides phosphoramidite metallocenes, as generally depicted in Structure 39:

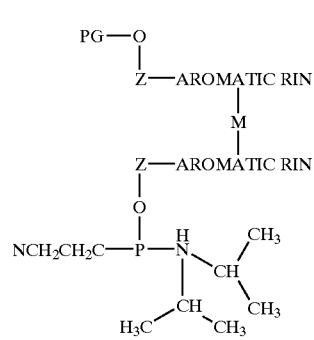

Structure 39

In Structure 39, PG is a protecting group, generally suitable for use in nucleic acid synthesis, with DMT, MMT and TMT all being preferred. The aromatic rings can either be the rings of the metallocene, or aromatic-rings of ligands for transition metal complexes or other organic ETMs. The aromatic rings may be the same or different, and may be substituted as discussed herein.

Structure 40 depicts the ferrocene derivative:

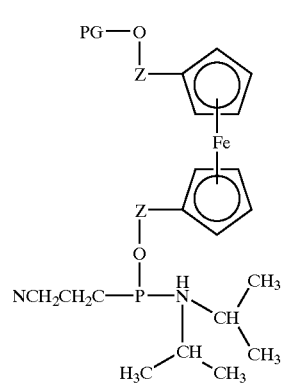

Structure 40

These phosphoramidite analogs can be added to standard oligonucleotide syntheses as is known in the art.

Structure 41 depicts the ferrocene peptide nucleic acid (PNA) monomer, that can be added to PNA synthesis (or regular protein synthesis) as is known in the art and depicted within the Figures and Examples:

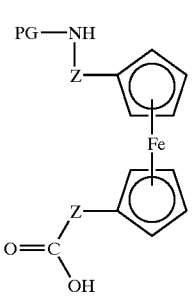

Structure 41

In Structure 41, the PG protecting group is suitable for use in peptide nucleic acid synthesis, with MMT, boc and Fmoc being preferred.

These same intermediate compounds can be used to form ETM or metallocene polymers, which are added to the nucleic acids, rather than as backbone replacements, as is more fully described below.

In a preferred embodiment, the ETMs are attached as polymers, for example as metallocene polymers, in a "branched" configuration similar to the "branched DNA" embodiments herein and as outlined in U.S. Pat. No. 5,124,246, using modified functionalized nucleotides. The general idea is as follows. A modified phosphoramidite nucleotide is generated that can ultimately contain a free hydroxy group that can be used in the attachment of phosphoramidite ETMs such as metallocenes. This free hydroxy group could be on the base or the backbone, such as the ribose or the phosphate (although as will be appreciated by those in the art, nucleic acid analogs containing other structures can also be used). The modified nucleotide is incorporated into a nucleic acid, and any hydroxy protecting groups are removed, thus leaving the free hydroxyl. Upon the addition of a phosphoramidite ETM such as a metallocene, as described above in structures 39 and 40, ETMs, such as metallocene ETMs, are added. Additional phosphoramidite ETMs such as metallocenes can be added, to form "ETM polymers", including "metallocene polymers" as depicted in FIGS. 21A–21E with ferrocene. In addition, in some embodiments, it is desirable to increase the solubility of the polymers by adding a "capping" group to the terminal ETM in the polymer, for example a final phosphate group to the metallocene as is generally depicted in FIGS. 21A–21E. Other suitable solubility enhancing "capping" groups will be appreciated by those in the art. It should be noted that these solubility enhancing groups can be added to the polymers in other places, including to the ligand rings, for example on the metallocenes as discussed herein A preferred embodiment of this general idea is outlined in the Figures. In this embodiment, the 2' position of a ribose of a phosphoramidite nucleotide is first functionalized to contain a protected hydroxy group, in this case via an oxo-linkage, although any number of linkers can be used, as is generally described herein for Z linkers. The protected modified nucleotide is then incorporated via standard phosphoramidite chemistry into a growing nucleic acid. The protecting group is removed, and the free hydroxy group is used, again using standard phosphoramidite chemistry to add a phosphoramidite metallocene such as ferrocene. A similar reaction is possible for nucleic acid analogs. For example, using peptide nucleic acids and the metallocene monomer shown in Structure 41, peptide nucleic acid structures containing metallocene polymers could be generated.

Thus, the present invention provides recruitment linkers of nucleic acids comprising "branches" of metallocene polymers as is generally depicted in FIGS. 21A–21E. Preferred embodiments also utilize metallocene polymers from one to about 50 metallocenes in length, with from about 5 to about 20 being preferred and from about 5 to about 10 being especially preferred.

In addition, when the recruitment linker is nucleic acid, any combination of ETM attachments may be done.

In a preferred embodiment, the recruitment linker is not nucleic acid, and instead may be any sort of linker or polymer. As will be appreciated by those in the art, generally any linker or polymer that can be modified to contain ETMs can be used. In general, the polymers or linkers should be reasonably soluble and contain suitable functional groups for the addition of ETMs.

As used herein, a "recruitment polymer" comprises at least two or three subunits, which are covalently attached. At least some portion of the monomeric subunits contain functional groups for the covalent attachment of ETMs. In some embodiments coupling moieties are used to covalently link the subunits with the ETMs. Preferred functional groups for attachment are amino groups, carboxy groups, oxo groups and thiol groups, with amino groups being particularly preferred. As will be appreciated by those in the art, a wide variety of recruitment polymers are possible.

Suitable linkers include, but are not limited to, alkyl linkers (including heteroalkyl (including (poly)ethylene glycol-type structures), substituted alkyl, aryalkyl linkers, etc. As above for the polymers, the linkers will comprise one or more functional groups for the attachment of ETMs, which will be done as will be appreciated by those in the art, for example through the use homo-or hetero-bifunctional linkers as are well known (see 1994 Pierce Chemical Company catalog, technical section on cross-linkers, pages 155–200, incorporated herein by reference).

Suitable recruitment polymers include, but are not limited to, functionalized styrenes, such as amino styrene, functionalized dextrans, and polyamino acids. Preferred polymers are polyamino acids (both poly-D-amino acids and poly-L-amino acids), such as polylysine, and polymers containing lysine and other amino acids being particularly preferred. Other suitable polyamino acids are polyglutamic acid, polyaspartic acid, co-polymers of lysine and glutamic or aspartic acid, co-polymers of lysine with alanine, tyrosine, phenylalanine, serine, tryptophan, and/or proline.

In a preferred embodiment, the recruitment linker comprises a metallocene polymer, as is described above.

The attachment of the recruitment linkers to either the solution binding ligand or the first portion of the label probe will depend on the composition of the recruitment linker and of the label and/or binding ligand, as will be appreciated by those in the art. When either the label probe or the binding ligand is nucleic acid, nucleic acid recruitment linkers are generally formed during the synthesis of the first species, with incorporation of nucleosides containing ETMs as required. Alternatively, the first portion of the label probe or the binding ligand and the recruitment linker may be made separately, and then attached. When they are both nucleic acid, there may be an overlapping section of complementarity, forming a section of double stranded nucleic acid that can then be chemically crosslinked, for example by using psoralen as is known in the art.

When non-nucleic acid recruitment linkers are used, attachment of the linker/polymer of the recruitment linker will be done generally using standard chemical techniques, such as will be appreciated by those in the art. For example, when alkyl-based linkers are used, attachment can be similar to the attachment of insulators to nucleic acids.

In addition, it is possible to have recruitment linkers that are mixtures of nucleic acids and non-nucleic acids, either in a linear form (i.e. nucleic acid segments linked together with alkyl linkers) or in branched forms (nucleic acids with alkyl "branches" that may contain ETMs and may be additionally branched).

It is also possible to have ETMs connected to probe sequences, i.e. sequences designed to hybridize to complementary sequences. Thus, ETMs may be added to non-recruitment linkers as well. For example, there may be ETMs added to sections of label probes that do hybridize to components of the assay complex, for example the first portion, or to the target sequence as outlined above and depicted in FIGS. 2A–2D. These ETMs may be used for electron transfer detection in some embodiments, or they may not, depending on the location and system. For example, in some embodiments, when for example the target sequence containing randomly incorporated ETMs is hybridized directly to the capture probe, as is depicted in FIGS. 2A–2D, there may be ETMs in the portion hybridizing to the capture probe. If the capture probe is attached to the electrode using a conductive oligomer, these ETMs can be used to detect electron transfer as has been previously described. Alternatively, these ETMs may not be specifically detected.

Similarly, in some embodiments, when the recruitment linker is nucleic acid, it may be desirable in some instances to have some or all of the recruitment linker be double stranded. In one embodiment, there may be a second recruitment linker, substantially complementary to the first recruitment linker, that can hybridize to the first recruitment linker. In a preferred embodiment, the first recruitment linker comprises the covalently attached ETMs. In an alternative embodiment, the second recruitment linker contains the ETMs, and the first recruitment linker does not, and the ETMs are recruited to the surface by hybridization of the second recruitment linker to the first. In yet another embodiment, both the first and second recruitment linkers comprise ETMs. It should be noted, as discussed above, that nucleic acids comprising a large number of ETMs may not hybridize as well, i.e. the $T_m$ may be decreased, depending on the site of attachment and the characteristics of the ETM. Thus, in general, when multiple ETMs are used on hybridizing strands, generally there are less than about 5, with less than about 3 being preferred, or alternatively the ETMs should be spaced sufficiently far apart that the intervening nucleotides can sufficiently hybridize to allow good kinetics.

In one embodiment, when nucleic acid targets and/or binding ligands and/or recruitment linkers are used, non-covalently attached ETMs may be used. In one embodiment, the ETM is a hybridization indicator. Hybridization indicators serve as an ETM that will preferentially associate with double stranded nucleic acid is added, usually reversibly, similar to the method of Millan et al., Anal. Chem. 65:2317–2323 (1993); Milian et al., Anal. Chem. 662943–2948 (1994), both of which are hereby expressly incorporated by reference. In this embodiment, increases in the local concentration of ETMs, due to the association of the ETM hybridization indicator with double stranded nucleic acid at the surface, can be monitored using the monolayers comprising the conductive oligomers. Hybridization indicators include intercalators and minor and/or major groove binding moieties. In a preferred embodiment, intercalators may be used; since intercalation generally only occurs in the. presence of double stranded nucleic acid, only in the presence of double stranded nucleic acid will the ETMs concentrate. Intercalating transition metal complex ETMs are known in the art. Similarly, major or minor groove binding moieties, such as methylene blue, may also be used in this embodiment.

Similarly, the systems of the invention may utilize non-covalently attached ETMs, as is generally described in Napier et al., Bioconj. Chem. 8:906 (1997), hereby expressly incorporated by reference. In this embodiment, changes in the redox state of certain molecules as a result of the presence of DNA (i.e. guanine oxidation by ruthenium complexes) can be detected using the SAMs comprising conductive oligomers as well.

Thus, the present invention provides electrodes comprising monolayers comprising conductive oligomers, generally including capture binding ligands, and either binding ligands or label probes that will bind to the binding ligands comprising recruitment linkers containing ETMs.

In a preferred embodiment, the compositions of the invention are used to detect target analytes in a sample. In a preferred embodiment, the target analyte is a nucleic acid, and thus detection of target sequences is done. The term "target sequence" or grammatical equivalents herein means a nucleic acid sequence on a single strand of nucleic acid. The target sequence may be a portion of a gene, a regulatory sequence, genomic DNA, cDNA, RNA including mRNA and rRNA, or others. It may be any length, with the understanding that longer sequences are more specific. As will be appreciated by those in the art, the complementary target sequence may take many forms. For example, it may be contained within a larger nucleic acid sequence, i.e. all or part of a gene or mRNA, a restriction fragment of a plasmid or genomic DNA, among others. As is outlined more fully below, probes are made to hybridize to target sequences to determine the presence or absence of the target sequence in a sample. Generally speaking, this term will be understood by those skilled in the art. The target sequence may also be comprised of different target domains; for example, a first target domain of the sample target sequence may hybridize to a capture probe or a portion of capture extender probe, a second target domain may hybridize to a portion of an amplifier probe, a label probe, or a different capture or capture extender probe, etc. The target domains may be adjacent or separated. The terms "first" and "second" are not meant to confer an orientation of the sequences with respect to the 5'-3' orientation of the target sequence. For example, assuming a 5'-3' orientation of the complementary target sequence, the first target domain may be located either 5' to the second domain, or 3' to the second domain.

If required, the target analyte is prepared using known techniques. For example, the sample may be treated to lyse the cells, using known lysis buffers, electroporation, etc., with purification occuring as needed, as will be appreciated by those in the art. In a preferred embodiment, when the target analyte is nucleic acid, amplification may be done, including PCR and other amplification techniques as outlined in PCT US99/01705, incorporated herein by reference in its entirety.

When the target analyte is a nucleic acid, probes of the present invention are designed to be complementary to a target sequence (either the target sequence of the sample or to other probe sequences, as is described below), such that hybridization of the target sequence and the probes of the present invention occurs. As outlined below, this complementarity need not be perfect; there may be any number of base pair mismatches which will interfere with hybridization between the target sequence and the single stranded nucleic acids of the present invention. However, if the number of mutations is so great that no hybridization can occur under even the least stringent of hybridization conditions, the sequence is not a complementary target sequence. Thus, by "substantially complementary" herein is meant that the probes are sufficiently complementary to the target sequences to hybridize under normal reaction conditions.

Generally, the nucleic acid compositions of the invention are useful as oligonucleotide probes. As is appreciated by those in the art, the length of the probe will vary with the length of the target sequence and the hybridization and wash conditions. Generally, oligonucleotide probes range from about 8 to about 50 nucleotides, with from about 10 to about 30 being preferred and from about 12 to about 25 being especially preferred. In some cases, very long probes may be used, e.g. 50 to 200–300 nucleotides in length. Thus, in the structures depicted herein, nucleosides may be replaced with nucleic acids.

A variety of hybridization conditions may be used in the present invention, including high, moderate and low stringency conditions; see for example Maniatis et al., Molecular Cloning: A Laboratory Manual, 2d Edition, 1989, and Short Protocols in Molecular Biology, ed. Ausubel, et al, hereby incorporated by referenece. The hybridization conditions may also vary when a non-ionic backbone, i.e. PNA is used, as is known in the art. In addition, cross-linking agents may be added after target binding to cross-link, i.e. covalently attach, the two strands of the hybridization complex.

As will be appreciated by those in the art, the nucleic acid systems of the invention may take on a large number of different configurations, as is generally depicted in the figures. In general, there are three types of systems that can be used: (1) systems in which the target analyte itself is labeled with ETMs (i.e. the use of a target analyte analog, for non-nucleic acid systems, or, for nucleic acid systems, the target sequence is labeled; see FIGS. 6A, 6B and 6C); (2) systems in which label probes (or capture binding ligands with recruitment linkers) directly bind (i.e. hybridize for nucleic acids) to the target analytes (see FIGS. 6D–6H for nucleic acid embodiments and FIG. 2A and 2C for non-nucleic acid embodiments); and (3) systems in which label probes comprising recruitment linkers are indirectly bound to the target analytes, for example through the use of amplifier probes (see FIGS. 6I, 6J and 6K for nucleic acid embodiments and FIG. 2B and 2D for non-nucleic acid embodiments).

In all three of these systems, it is preferred, although not required, that the target analyte be immobilized on the electrode surface. This is preferably done using capture binding ligands and optionally one or more capture extender ligands. When only capture binding ligands are utilized, it is necessary to have unique capture binding ligands for each target analyte; that is, the surface must be customized to contain unique capture binding ligands. Alternatively, the use of capture extender ligands, particularly when the capture extender ligands are capture extender probes (i.e. nucleic acids) may be used, that allow a "universal" surface, i.e. a surface containing a single type of capture probe that can be used to detect any target sequence.

Capture extender probes or moieties may take on a variety of different conformations, depending on the identity of the target analyte and of the binding ligands. In a preferred embodiment, the target analyte and the binding ligand are nucleic acids. In this embodiment, the "capture extender" probes are generally depicted in FIG. 6 and have a first portion that will hybridize to all or part of the capture probe, and a second portion that will hybridize to a portion of the target sequence. This then allows the generation of customized soluble probes, which as will be appreciated by those in the art is generally simpler and less costly. As shown herein (e.g. FIG. 6H), two capture extender probes may be used. This has generally been done to stabilize assay complexes (for example when the target sequence is large, or when large amplifier probes (particularly branched or dendrimer amplifier probes) are used.

When the capture binding ligand is not a nucleic acid, capture extender components may still be used. In one embodiment, as depicted in FIG. 2C, the capture binding ligand has an associated capture extender of nucleic acid (although as will be appreciated by those in the art, it could be part of a binding pair as well), that can be used to target to the electrode surface. Alternatively, an additional capture extender component can be used, to allow a "generic" surface (see FIG. 1).

In a preferred embodiment, the capture binding ligands are added after the formation of the SAM ((4) above). This may be done in a variety of ways, as will be appreciated by those in the art. In one embodiment, conductive oligomers with terminal functional groups are made, with preferred embodiments utilizing activated carboxylates and isothiocyanates, that will react with primary amines that are put onto the binding ligand, as is generally depicted in FIG. 7 using an activated carboxylate and nucleic acid, although other capture ligands may be attached in this way as well. These two reagents have the advantage of being stable in aqueous solution, yet react with primary alkylamines. This allows the spotting of probes (either capture or detection probes, or both) using known methods (ink jet, spotting, etc.) onto the surface.

In addition, there are a number of non-nucleic acid methods that can be used to immobilize a capture binding ligand on a surface. For example, binding partner pairs can be utilized; i.e. one binding partner is attached to the terminus of the conductive oligomer, and the other to the end of the binding ligand. This may also be done without using a nucleic acid capture probe; that is, one binding partner serves as the capture probe and the other is attached to either the target sequence or a capture extender probe. That is, either the target sequence comprises the binding partner, or a capture extender probe that will hybridize to the target sequence comprises the binding partner. Suitable binding partner pairs include, but are not limited to, hapten pairs such as biotin/streptavidin; antigens/antibodies; NTA/histidine tags; etc. In general, smaller binding partners are preferred.

In a preferred embodiment, when the target sequence itself is modified to contain a binding partner, the binding partner is attached via a modified nucleotide that can be enzymatically attached to the target sequence, for example during a PCR target amplification step. Alternatively, the binding partner should be easily attached to the target sequence.

Alternatively, a capture extender probe may be utilized that has a nucleic acid portion for hybridization to the target as well as a binding partner (for example, the capture extender probe may comprise a non-nucleic acid portion such as an alkyl linker that is used to attach a binding partner). In this embodiment, it may be desirable to cross-link the double-stranded nucleic acid of the target and capture extender probe for stability, for example using psoralen as is known in the art.

In one embodiment, the target is not bound to the electrode surface using capture binding ligands. In this embodiment, what is important, as for all the assays herein, is that excess label probes be removed prior to detection and that the assay complex (comprising the recruitment linker) be in proximity to the surface. As will be appreciated by those in the art, this may be accomplished in other ways. For example, the assay complex may be present on beads that are added to the electrode comprising the monolayer. The recruitment linkers comprising the ETMs may be placed in proximity to the conductive oligomer surface using techniques well known in the art, including gravity settling of the beads on the surface, electrostatic or magnetic interactions between bead components and the surface, using binding partner attachment as outlined above. Alternatively, after the removal of excess reagents such as excess label probes, the assay complex may be driven down to the surface, for example by pulsing the system with a voltage sufficient to drive the assay complex to the surface.

However, preferred embodiments utilize assay complexes attached via capture binding ligands.

For nucleic acid systems, a preferred embodiments utilize the target sequence itself containing the ETMs. As discussed above, this may be done using target sequences that have ETMs incorporated at any number of positions, as outlined above. Representative examples are depicted in FIGS. 6A, 6B and 6C. In this embodiment, as for the others of the system, the 3'-5' orientation of the probes and targets is chosen to get the ETM-containing structures (i.e. recruitment linkers or target sequences) as close to the surface of the monolayer as possible, and in the correct orientation. This may be done using attachment via insulators or conductive oligomers as is generally shown in the Figures. In addition, as will be appreciated by those in the art, multiple capture probes can be utilized, either in a configuration such as depicted in FIG. 6C, wherein the 5'-3' orientation of the capture probes is different, or where "loops" of target form when multiples of capture probes as depicted in FIGS. 6A and 6B are used.

For nucleic acid systems, a preferred embodiments utilize the label probes directly hybridizing to the target sequences, as is generally depicted in FIGS. 6D–6I. In these embodiments, the target sequence is preferably, but not required to be, immobilized on the surface using capture probes, including capture extender probes. Label probes are then used to bring the ETMs into proximity of the surface of the monolayer comprising conductive oligomers. In a preferred embodiment, multiple label probes are used; that is, label probes are designed such that the portion that hybridizes to the target sequence (labeled 41 in the figures) can be different for a number of different label probes, such that amplification of the signal occurs, since multiple label probes can bind for every target sequence. Thus, as depicted in the figures, n is an integer of at least one. Depending on the sensitivity desired, the length of the target sequence, the number of ETMs per label probe, etc., preferred ranges of n are from 1 to 50, with from about 1 to about 20 being particularly preferred, and from about 2 to about 5 being especially preferred. In addition, if "generic" label probes are desired, label extender probes can be used as generally described below for use with amplifier probes.

As above, generally in this embodiment the configuration of the system and the label probes (recruitment linkers) are designed to recruit the ETMs as close as possible to the monolayer surface.

In a preferred embodiment, the label probes are bound to the target analyte indirectly. That is, the present invention finds use in novel combinations of signal amplification technologies and electron transfer detection on electrodes, which may be particularly useful in sandwich hybridization assays, for nucleic acid detection, as generally depicted in FIGS. 6I et seq. In these embodiments, the amplifier probes of the invention are bound to the target sequence in a sample either directly or indirectly. Since the amplifier probes preferably contain a relatively large number of amplification sequences that are available for binding of label probes, the detectable signal is significantly increased, and allows the detection limits of the target to be significantly improved. These label and amplifier probes, and the detection methods described herein, may be used in essentially any known nucleic acid hybridization formats, such as those in which the target is bound directly to a solid phase or in sandwich hybridization assays in which the target is bound to one or more nucleic acids that are in turn bound to the solid phase.

In general, these embodiments may be described as follows. An amplifier probe is hybridized to the target sequence, either directly (e.g. FIG. 6I), or through the use of a label extender probe (e.g. FIG. 6N and 6O), which serves to allow "generic" amplifier probes to be made. The target sequence is preferably, but not required to be, immobilized on the electrode using capture probes. Preferably, the amplifier probe contains a multiplicity of amplification sequences, although in some embodiments, as described below, the amplifier probe may contain only a single amplification sequence. The amplifier probe may take on a number of different forms; either a branched conformation, a dendrimer conformation, or a linear "string" of amplification sequences. These amplification sequences are used to form hybridization complexes with label probes, and the ETMs can be detected using the electrode.

Accordingly, the present invention provides assay complexes comprising at least one amplifier probe. By "amplifier probe" or "nucleic acid multimer" or "amplification multimer" or grammatical equivalents herein is meant a nucleic acid probe that is used to facilitate signal amplification. Amplifier probes comprise at least a first single-stranded nucleic acid probe sequence, as defined below, and at least one single-stranded nucleic acid amplification sequence, with a multiplicity of amplification sequences being preferred. In some embodiments, it is possible to use amplifier binding ligands, that are non-nucleic acid based but that comprise a plurality of binding sites for the later association/binding of label ligands comprising recruitment linkers. However, amplifier probes are preferred in nucleic acid systems.

Amplifier probes comprise a first probe sequence that is used, either directly or indirectly; to hybridize to the target sequence. That is, the amplifier probe itself may have a first probe sequence that is substantially complementary to the target sequence (e.g. FIG. 6I), or it has a first probe sequence that is substantially complementary to a portion of an additional probe, in this case called a label extender probe, that has a first portion that is substantially complementary to the target sequence (e.g. FIG. 6N). In a preferred embodiment, the first probe sequence of the amplifier probe is substantially complementary to the target sequence, as is generally depicted in FIG. 6I.

In general, as for all the probes herein, the first probe sequence is of a length sufficient to give specificity and stability. Thus generally, the probe sequences of the invention that are designed to hybridize to another nucleic acid (i.e. probe sequences, amplification sequences, portions or domains of larger probes) are at least about 5 nucleosides long, with at least about 10 being preferred and at least about 15 being especially preferred.

In a preferred embodiment, as is depicted in FIG. 8, the amplifier probes, or any of the other probes of the invention, may form hairpin stem-loop structures in the absence of their target. The length of the stem double-stranded sequence will be selected such that the hairpin structure is not favored in the presence of target. The use of these type of probes, in the systems of the invention or in any nucleic acid detection systems, can result in a significant decrease in non-specific binding and thus an increase in the signal to noise ratio.

Generally, these hairpin structures comprise four components. The first component is a target binding sequence; i.e. a region complementary to the target (which may be the sample target sequence or another probe sequence to which binding is desired), that is about 10 nucleosides long, with about 15 being preferred. The second component is a loop sequence, that can facilitate the formation of nucleic acid loops. Particularly preferred in this regard are repeats of GTC, which has been identified in Fragile X Syndrome as forming turns. (When PNA analogs are used, turns comprising proline residues may be preferred). Generally, from three to five repeats are used, with four to five being preferred. The third component is a self-complementary region, which has a first portion that is complementary to a portion of the target sequence region and a second portion that comprises a first portion of the label probe binding sequence. The fourth component is substantially complementary to a label probe (or other probe, as the case may be). The fourth component further comprises a "sticky end", that is, a portion that does not hybridize to any other portion of the probe, and preferably contains most, if not all, of the ETMs. The general structure is depicted in FIGS. 3E–3G. As will be appreciated by those in the art, the any or all of the probes described herein may be configured to form hairpins in the absence of their targets, including the amplifier, capture, capture extender, label and label extender probes.

In a preferred embodiment, several different amplifier probes are used, each with first probe sequences that will hybridize to a different portion of the target sequence. That is, there is more than one level of amplification; the amplifier probe provides an amplification of signal due to a multiplicity of labelling events, and several different amplifier probes, each with this multiplicity of labels, for each target sequence is used. Thus, preferred embodiments utilize at least two different pools of amplifier probes, each pool having a different probe sequence for hybridization to different portions of the target sequence; the only real limitation on the number of different amplifier probes will be the length of the original target sequence. In addition, it is also possible that the different amplifier probes contain different amplification sequences, although this is generally not preferred.

In a preferred embodiment, the amplifier probe does not hybridize to the sample target sequence directly, but instead hybridizes to a first portion of a label extender probe, as is generally depicted in FIGS. 3E–3G. This is particularly useful to allow the use of "generic" amplifier probes, that is, amplifier probes that can be used with a variety of different targets. This may be desirable since several of the amplifier probes require special synthesis techniques. Thus, the addition of a relatively short probe as a label extender probe is preferred. Thus, the first probe sequence of the amplifier probe is substantially complementary to a first portion or domain of a first label extender single-stranded nucleic acid probe. The label extender probe also contains a second portion or domain that is substantially complementary to a portion of the target sequence. Both of these portions are preferably at least about 10 to about 50 nucleotides in length, with a range of about 15 to about 30 being preferred. The terms "first" and "second" are not meant to confer an orientation of the sequences with respect to the 5'-3' orientation of the target or probe sequences. For example, assuming a 5'-3' orientation of the complementary target sequence, the first portion may be located either 5' to the second portion, or 3' to the second portion. For convenience herein, the order of probe sequences are generally shown from left to right.

In a preferred embodiment, more than one label extender probe-amplifier probe pair may be used, tht is, n is more than 1. That is, a plurality of label extender probes may be used, each with a portion that is substantially complementary to a different portion of the target sequence; this can serve as another level of amplification. Thus, a preferred embodiment utilizes pools of at least two label extender probes, with the upper limit being set by the length of the target sequence.

In a preferred embodiment, more than one label extender probe is used with a single amplifier probe to reduce non-specific binding, as is depicted in FIG. 6O and generally outlined in U.S. Pat. No. 5,681,697, incorporated by reference herein. In this embodiment, a first portion of the first label extender probe hybridizes to a first portion of the target sequence, and the second portion of the first label extender probe hybridizes to a first probe sequence of the amplifier probe. A first portion of the second label extender probe hybridizes to a second portion of the target sequence, and the second portion of the second label extender probe hybridizes to a second probe sequence of the amplifier probe. These form structures sometimes referred to as "cruciform" structures or configurations, and are generally done to confer stability when large branched or dendrimeric amplifier probes are used.

In addition, as will be appreciated by those in the art, the label extender probes may interact with a preamplifier probe, described below, rather than the amplifier probe directly.

Similarly, as outlined above, a preferred embodiment utilizes several different amplifier probes, each with first probe sequences that will hybridize to a different portion of the label extender probe. In addition, as outlined above, it is also possible that the different amplifier probes contain different amplification sequences, although this is generally not preferred.

In addition to the first probe sequence, the amplifier probe also comprises at least one amplification sequence. An "amplification sequence" or "amplification segment" or grammatical equivalents herein is meant a sequence that is used, either directly or indirectly, to bind to a first portion of a label probe as is more fully described below. Preferably, the amplifier probe comprises a multiplicity of amplification sequences, with from about 3 to about 1000 being preferred, from about 10 to about 100 being particularly preferred, and about 50 being especially preferred. In some cases, for example when linear amplifier probes are used, from 1 to about 20 is preferred with from about 5 to about 10 being particularly preferred. Again, when non-nucleic acid amplifier moieties are used, the amplification segment can bind label ligands.

The amplification sequences may be linked to each other in a variety of ways, as will be appreciated by those in the art. They may be covalently linked directly to each other, or to intervening sequences or chemical moieties, through nucleic acid linkages such as phosphodiester bonds, PNA bonds, etc., or through interposed linking agents such amino acid, carbohydrate or polyol bridges, or through other cross-linking agents or binding partners. The site(s) of linkage may be at the ends of a segment, and/or at one or more internal nucleotides in the strand. In a preferred embodiment, the amplification sequences are attached via nucleic acid linkages.

In a preferred embodiment, branched amplifier probes are used, as are generally described in U.S. Pat. No. 5,124,246, hereby incorporated by reference. Branched amplifier probes may take on "fork-like" or "comb-like" conformations. "Fork-like" branched amplifier probes generally have three or more oligonucleotide segments emanating from a point of origin to form a branched structure. The point of origin may be another nucleotide segment or a multifunctional molecule to whcih at least three segments can be covalently or tightly bound. "Comb-like" branched amplifier probes have a linear backbone with a multiplicity of sidechain oligonucleotides extending from the backbone. In either conformation, the pendant segments will normally depend from a modified nucleotide or other organic moiety having the appropriate functional groups for attachment of oligonucleotides. Furthermore, in either conformation, a large number of amplification sequences are available for binding, either directly or indirectly, to detection probes. In general, these structures are made as is known in the art, using modified multifunctional nucleotides, as is described in U.S. Pat. Nos. 5,635,352 and 5,124,246, among others.

In a preferred embodiment, dendrimer amplifier probes are used, as are generally described in U.S. Pat. No. 5,175,270, hereby expressly incorporated by reference. Dendrimeric amplifier probes have amplification sequences that are attached via hybridization, and thus have portions of double-stranded nucleic acid as a component of their structure. The outer surface of the dendrimer amplifier probe has a multiplicity of amplification sequences.

In a preferred embodiment, linear amplifier probes are used, that have individual amplification sequences linked end-to-end either directly or with short intervening sequences to form a polymer. As with the other amplifier configurations, there may be additional sequences or moieties between the amplification sequences. In addition, as outlined herein, linear amplification probes may form hairpin stem-loop structures, as is depicted in FIG. 8.

In one embodiment, the linear amplifier probe has a single amplification sequence. This may be useful when cycles of hybridization/disassociation occurs, forming a pool of amplifier probe that was hybridized to the target and then removed to allow more probes to bind, or when large numbers of ETMs are used for each label probe. However, in a preferred embodiment, linear amplifier probes comprise a multiplicity of amplification sequences.

In addition, the amplifier probe may be totally linear, totally branched, totally dendrimeric, or any combination thereof.

The amplification sequences of the amplifier probe are used, either directly or indirectly, to bind to a label probe to allow detection. In a preferred embodiment, the amplification sequences of the amplifier probe are substantially complementary to a first portion of a label probe. Alternatively, amplifier extender probes are used, that have a first portion that binds to the amplification sequence and a second portion that binds to the first portion of the label probe.

In addition, the compositions of the invention may include "preamplifier" molecules, which serves a bridging moiety between the label extender molecules and the amplifier probes. In this way, more amplifier and thus more ETMs are ultimately bound to the detection probes. Preamplifier molecules may be either linear or branched, and typically contain in the range of about 30–3000 nucleotides.

The reactions outlined below may be accomplished in a variety of ways, as will be appreciated by those in the art. Components of the reaction may be added simultaneously, or sequentially, in any order, with preferred embodiments outlined below. In addition, the reaction may include a variety of other reagents may be included in the assays. These include reagents like salts, buffers, neutral proteins, e.g. albumin, detergents, etc which may be used to facilitate optimal hybridization and detection, and/or reduce non-specific or background interactions. Also reagents that otherwise improve the efficiency of the assay, such as protease inhibitors, nuclease inhibitors, anti-microbial agents, etc., may be used, depending on the sample preparation methods and purity of the target.

Generally, the methods are as follows. In a preferred embodiment, the target is initially immobilized or attached to the electrode. For nucleic acids, this is done by forming a hybridization complex between a capture probe and a portion of the target sequence. A preferred embodiment utilizes capture extender probes; in this embodiment, a hybridization complex is formed between a portion of the target sequence and a first portion of a capture extender probe, and an additional hybridization complex between a second portion of the capture extender probe and a portion of the capture probe. Additional preferred embodiments utilize additional capture probes, thus forming a hybridization complex between a portion of the target sequence and a first portion of a second capture extender probe, and an additional hybridization complex between a second portion of the second capture extender probe and a second portion of the capture probe. Non-nucleic acid embodiments utilize capture binding ligands and optional capture extender ligands.

Alternatively, the attachment of the target sequence to the electrode is done simultaneously with the other reactions.

The method proceeds with the introduction of amplifier probes, if utilized. In a preferred embodiment, the amplifier probe comprises a first probe sequence that is substantially complementary to a portion of the target sequence, and at least one amplification sequence.

In one embodiment, the first probe sequence of the amplifier probe is hybridized to the target sequence, and any unhybridized amplifier probe is removed. This will generally be done as is known in the art, and depends on the type of assay. When the target sequence is immobilized on a surface such as an electrode, the removal of excess reagents generally is done via one or more washing steps, as will be appreciated by those in the art. In this embodiment, the target may be immobilized on any solid support. When the target sequence is not immobilized on a surface, the removal of excess reagents such as the probes of the invention may be done by adding beads (i.e. solid support particles) that contain complementary sequences to the probes, such that the excess probes bind to the beads. The beads can then be removed, for example by centrifugation, filtration, the application of magnetic or electrostatic fields, etc.

The reaction mixture is then subjected to conditions (temperature, high salt, changes in pH, etc.) under which the amplifier probe disassociates from the target sequence, and the amplifier probe is collected. The amplifier probe may then be added to an electrode comprising capture probes for the amplifier probes, label probes added, and detection is achieved.

In a preferred embodiment, a larger pool of probe is generated by adding more amplifier probe to the target sequence and the hybridization/disassociation reactions are repeated, to generate a larger pool of amplifier probe. This pool of amplifier probe is then added to an electrode comprising amplifier capture probes, label probes added, and detection proceeds.

In this embodiment, it is preferred that the target analyte be immobilized on a solid support, including an electrode, using the methods described herein; although as will be appreciated by those in the art, alternate solid support attachment technologies may be used, such as attachment to glass, polymers, etc. It is possible to do the reaction on one solid support and then add the pooled amplifier probe to an electrode for detection.

In a preferred embodiment, the amplifier probe comprises a multiplicity of amplification sequences.

In one embodiment, the first probe sequence of the amplifier probe is hybridized to the target sequence, and any unhybridized amplifier probe is removed. Again, preferred embodiments utilize immobilized target sequences, wherein the target sequences are immobilized by hybridization with capture probes that are attached to the electrode, or hybridization to capture extender probes that in turn hybridize with immobilized capture probes as is described herein. Generally, in these embodiments, the capture probes and the detection probes are immobilized on the electrode, generally at the same "address".

In a preferred embodiment, the first probe sequence of the amplifier probe is hybridized to a first portion of at least one label extender probe, and a second portion of the label extender probe is hybridized to a portion of the target sequence. Other preferred embodiments utilize more than one label extender probe, as is generally shown in FIG. 6O.

In a preferred embodiment, the amplification sequences of the amplifier probe are used directly for detection, by hybridizing at least one label probe sequence.

The invention thus provides assay complexes that minimally comprise a target sequence and a label probe. "Assay complex" herein is meant the collection of binding complexes comprising capture binding ligands, target analytes (or analogs, as described below) and label moieties comprising recruitment linkers that allows detection. The composition of the assay complex depends on the use of the different components outlined herein. Thus, in FIG. 6A, the assay complex comprises the capture probe and the target sequence. The assay complexes may also include capture extender ligands (including probes), label extender ligands, and amplifier ligands, as outlined herein, depending on the configuration used.

The assays are generally run under conditions which allows formation of the assay complex only in the presence of target. Stringency can be controlled by altering a step parameter that is a thermodynamic variable, including, but not limited to, temperature, formamide concentration, salt concentration, chaotropic salt concentration pH, organic solvent concentration, etc.

These parameters may also be used to control non-specific binding for nucleic acids, as is generally outlined in U.S. Pat. No. 5,681,697. Thus it may be desirable to perform certain steps at higher stringency conditions; for example, when an initial hybridization step is done between the target sequence and the label extender and capture extender probes. Running this step at conditions which favor specific binding can allow the reduction of non-specific binding.

In a preferred embodiment, when all of the components outlined herein are used, a preferred method for nucleic acid detection is as follows. Single-stranded target sequence is incubated under hybridization conditions with the capture extender probes and the label extender probes. A preferred embodiment does this reaction in the presence of the electrode with immobilized capture probes, although this may also be done in two steps, with the initial incubation and the subsequent addition to the electrode. Excess reagents are washed off, and amplifier probes are then added. If preamplifier probes are used, they may be added either prior to the amplifier probes or simultaneously with the amplifier probes. Excess reagents are washed off, and label probes are then added. Excess reagents are washed off, and detection proceeds as outlined below.

In one embodiment, a number of capture probes (or capture probes and capture extender probes) that are each substantially complementary to a different portion of the target sequence are used.

Again, as outlined herein, when amplifier probes are used, the system is generally configured such that upon label probe binding, the recruitment linkers comprising the ETMs are placed in proximity to the monolayer surface. Thus for example, when the ETMs are attached via "dendrimer" type structures as outlined herein, the length of the linkers from the nucleic acid point of attachment to the ETMs may vary, particularly with the length of the capture probe when capture extender probes are used. That is, longer capture probes, with capture extenders, can result in the target sequences being "held" further away from the surface than for shorter capture probes. Adding extra linking sequences between the probe nucleic acid and the ETMs can result in the ETMs being spatially closer to the surface, giving better results.

In addition, if desirable, nucleic acids utilized in the invention may also be ligated together prior to detection, if applicable, by using standard molecular biology techniques such as the use of a ligase. Similarly, if desirable for stability, cross-linking agents may be added to hold the structures stable.

Other embodiments of the invention utilize different steps. For example, competitive assays may be run. In this embodiment, the target analyte in a sample may be replaced by a target analyte analog comprising a portion that either comprises a recruitment linker or can indirectly bind a recruitment linker. This may be done as is known in the art, for example by using affinity chromatography techniques that exchange the analog for the analyte, leaving the analyte bound and the analog free to interact with the capture binding ligands on the electrode surface. This is generally depicted in FIG. 4A.

Alternatively, a preferred embodiment utilizes a competitive binding assay when the solution binding ligand comprises a directly or indirectly associated recruitment linker comprising ETMs. In this embodiment, a target analyte or target analyte analog that will bind the solution binding ligand is attached to the surface. The solution binding ligand will bind to the surface bound analyte and give a signal. Upon introduction of the target analyte of the sample, a proportion of the solution binding. ligand will dissociate from the surface bound target and bind to the incoming target analyte. Thus, a loss of signal proportional to the amount of target analyte in the sample is seen.

The compositions of the invention are generally synthesized as outlined below, generally utilizing techniques well known in the art. As will be appreciated by those in the art, many of the techniques outlined below are directed to nucleic acids containing a ribose-phosphate backbone. However, as outlined above, many alternate nucleic acid analogs may be utilized, some of which may not contain either ribose or phosphate in the backbone. In these embodiments, for attachment at positions other than the base, attachment is done as will be appreciated by those in the art, depending on the backbone. Thus, for example, attachment can be made at the carbon atoms of the PNA backbone, as is described below, or at either terminus of the PNA.

The compositions may be made in several ways. A preferred method first synthesizes a conductive oligomer attached to a nucleoside, with addition of additional nucleosides to form the capture probe followed by attachment to the electrode. Alternatively, the whole capture probe may be made and then the completed conductive oligomer added, followed by attachment to the electrode. Alternatively, a monolayer of conductive oligomer (some of which have functional groups for attachment of capture probes) is attached to the electrode first, followed by attachment of the capture probe. The latter two methods may be preferred when conductive oligomers are used which are not stable in the solvents and under the conditions used in traditional nucleic acid synthesis.

In a preferred embodiment, the compositions of the invention are made by first forming the conductive oligomer covalently attached to the nucleoside, followed by the addition of additional nucleosides to form a capture probe nucleic acid, with the last step comprising the addition of the conductive oligomer to the electrode.

The attachment of the conductive oligomer to the nucleoside may be done in several ways. In a preferred embodiment, all or part of the conductive oligomer is synthesized first (generally with a functional group on the end for attachment to the electrode), which is then attached to the nucleoside. Additional nucleosides are then added as required, with the last step generally being attachment to the electrode. Alternatively, oligomer units are added one at a time to the nucleoside, with addition of additional nucleosides and attachment to the electrode. A number of representative syntheses are shown in the Figures of WO 98/20162, PCT US98/12430, PCT US99/01705 and PCT US99/01703, all of which are expressly incorporated by reference.

The conductive oligomer is then attached to a nucleoside that may contain one (or more) of the oligomer units, attached as depicted herein.

In a preferred embodiment, attachment is to a ribose of the ribose-phosphate backbone in a number of ways, including attachment via amide and amine linkages. In a preferred embodiment, there is at least a methylene group or other short aliphatic alkyl groups (as a Z group) between the nitrogen attached to the ribose and the aromatic ring of the conductive oligomer.

Alternatively, attachment is via a phosphate of the ribose-phosphate backbone.

In a preferred embodiment, attachment is via the base, and can include acetylene linkages and amide linkages. In a preferred embodiment, protecting groups may be added to the base prior to addition of the conductive oligomers. In addition, the palladium cross-coupling reactions may be altered to prevent dimerization problems; i.e. two conductive oligomers dimerizing, rather than coupling to the base.

Alternatively, attachment to the base may be done by making the nucleoside with one unit of the oligomer, followed by the addition of others.

Once the modified nucleosides are prepared, protected and activated, prior to attachment to the electrode, they may be incorporated into a growing oligonucleotide by standard synthetic techniques (Gait, Oligonucleotide Synthesis: A Practical Approach, IRL Press, Oxford, UK 1984; Eckstein) in several ways.

In one embodiment, one or more modified nucleosides are converted to the triphosphate form and incorporated into a growing oligonucleotide chain by using standard molecular biology techniques such as with the use of the enzyme DNA polymerase I, T4 DNA polymerase, T7 DNA polymerase, Taq DNA polymerase, reverse transcriptase, and RNA polymerases. For the incorporation of a 3' modified nucleoside to a nucleic acid, terminal deoxynucleotidyltransferase may be used. (Ratliff, Terminal deoxynucleotidyltransferase. In The Enzymes, Vol 14A. P. D. Boyer ed. pp 105–118. Academic Press, San Diego, Calif. 1981). Thus, the present invention provides deoxyribonucleoside triphosphates comprising a covalently attached ETM. Preferred embodiments utilize ETM attachment to the base or the backbone, such as the ribose (preferably in the 2' position), as is generally depicted below in Structures 42 and 43:

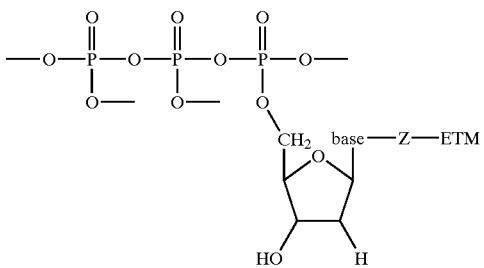

Structure 42

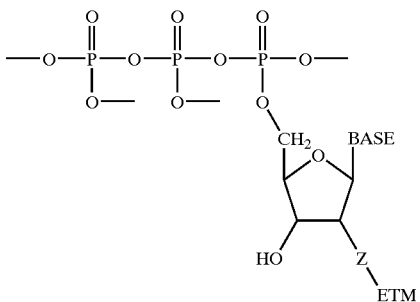

Structure 43

Thus, in some embodiments, it may be possible to generate the nucleic acids comprising ETMs in situ. For example, a target sequence can hybridize to a capture probe (for example on the surface) in such a way that the terminus of the target sequence is exposed, i.e. unhybridized. The addition of enzyme and triphosphate nucleotides labelled with ETMs allows the in situ creation of the label. Similarly, using labeled nucleotides recognized by polymerases can allow simultaneous PCR and detection; that is, the target sequences are generated in situ.

In a preferred embodiment, the modified nucleoside is converted to the phosphoramidite or H-phosphonate form, which are then used in solid-phase or solution syntheses of oligonucleotides. In this way the modified nucleoside, either for attachment at the ribose (i.e. amino- or thiol-modified nucleosides) or the base, is incorporated into the oligonucleotide at either an internal position or the 5' terminus. This is generally done in one of two ways. First, the 5' position of the ribose is protected with 4',4-dimethoxytrityl (DMT) followed by reaction with either 2-cyanoethoxy-bis-diisopropylaminophosphine in the presence of diisopropylammonium tetrazolide, or by reaction with chlorodiisopropylamino 2'-cyanoethyoxyphosphine, to give the phosphoramidite as is known in the art; although other techniques may be used as will be appreciated by those in the art. See Gait, supra; Caruthers, Science 230:281 (1985), both of which are expressly incorporated herein by reference.

For attachment of a group to the 3' terminus, a preferred method utilizes the attachment of the modified nucleoside (or the nucleoside replacement) to controlled pore glass (CPG) or other oligomeric supports. In this embodiment, the modified nucleoside is protected at the 5' end with DMT, and then reacted with succinic anhydride with activation. The resulting succinyl compound is attached to CPG or other oligomeric supports as is known in the art. Further phosphoramidite nucleosides are added, either modified or not, to the 5' end after deprotection. Thus, the present invention provides conductive oligomers or insulators covalently attached to nucleosides attached to solid oligomeric supports such as CPG, and phosphoramidite derivatives of the nucleosides of the invention.

The invention further provides methods of making label probes with recruitment linkers comprising ETMs. These synthetic reactions will depend on the character of the recruitment linker and the method of attachment of the ETM, as will be appreciated by those in the art. For nucleic acid recruitment linkers, the label probes are generally made as outlined herein with the incorporation of ETMs at one or more positions. When a transition metal complex is used as the ETM, synthesis may occur in several ways. In a preferred embodiment, the ligand(s) are added to a nucleoside, followed by the transition metal ion, and then the nucleoside with the transition metal complex attached is added to an oligonucleotide, i.e. by addition to the nucleic acid synthesizer. Alternatively, the ligand(s) may be attached, followed by incorporation into a growing oligonucleotide chain, followed by the addition of the metal ion.

In a preferred embodiment, ETMs are attached to a ribose of the ribose-phosphate backbone. This is generally done as is outlined herein for conductive oligomers, as described herein, and in PCT publication WO 95/15971, using amino-modified or oxo-modified nucleosides, at either the 2' or 3' position of the ribose. The amino group may then be used either as a ligand, for example as a transition metal ligand for attachment of the metal ion, or as a chemically. functional group that can be used for attachment of other ligands or organic ETMs, for example via amide linkages, as will be appreciated by those in the art. For example, the examples describe the synthesis of nucleosides with a variety of ETMs attached via the ribose.

In a preferred embodiment, ETMs are attached to a phosphate of the ribose-phosphate backbone. As outlined herein, this may be done using phosphodiester analogs such as phosphoramidite bonds, see generally PCT publication WO 95/15971, or the figures.

Attachment to alternate backbones, for example peptide nucleic acids or alternate phosphate linkages will be done as will be appreciated by those in the art.

In a preferred embodiment, ETMs are attached to a base of the nucleoside. This may be done in a variety of ways. In one embodiment, amino groups of the base, either naturally occurring or added as is described herein (see the figures, for example), are used either as ligands for transition metal complexes or as a chemically functional group that can be used to add other ligands, for example via an amide linkage, or organic ETMs. This is done as will be appreciated by those in the art. Alternatively, nucleosides containing halogen atoms attached to the heterocyclic ring are commercially available. Acetylene linked ligands may be added using the halogenated bases, as is generally known; see for example, Tzalis et al., Tetrahedron Lett. 36(34):6017–6020 (1995); Tzalis et al., Tetrahedron Lett. 36(2):3489–3490 (1995); and Tzalis et al., Chem. Communications (in press) 1996, all of which are hereby expressly incorporated by reference. See also the figures and the examples, which describes the synthesis of metallocenes (in this case, ferrocene) attached via acetylene linkages to the bases.

In one embodiment, the nucleosides are made with transition metal ligands, incorporated into a nucleic acid, and then the transition metal ion and any remaining necessary ligands are added as is known in the art. In an alternative embodiment, the transition metal ion and additional ligands are added prior to incorporation into the nucleic acid.

Once the nucleic acids of the invention are made, with a covalently attached attachment linker (i.e. either an insulator or a conductive oligomer), the attachment linker is attached to the electrode. The method will vary depending on the type of electrode used. As is described herein, the attachment linkers are generally made with a terminal "A" linker to facilitate attachment to the electrode. For the purposes of this application, a sulfur-gold attachment is considered a covalent attachment.

In a preferred embodiment, conductive oligomers, insulators, and attachment linkers are covalently attached via sulfur linkages to the electrode. However, surprisingly, traditional protecting groups for use of attaching molecules to gold electrodes are generally not ideal for use in both synthesis of the compositions described herein and inclusion in oligonucleotide synthetic reactions. Accordingly, the present invention provides novel methods for the attachment of conductive oligomers to gold electrodes, utilizing unusual protecting groups, including ethylpyridine, and trimethylsilylethyl as is depicted in the Figures. However, as will be appreciated by those in the art, when the conductive oligomers do not contain nucleic acids, traditional protecting groups such as acetyl groups and others may be used. See Greene et al., supra.

This may be done in several ways. In a preferred embodiment, the subunit of the conductive oligomer Which contains the sulfur atom for attachment to the electrode is protected with an ethyl-pyridine or trimethylsilylethyl group. For the former, this is generally done by contacting the subunit containing the sulfur atom (preferably in the form of a sulfhydryl) with a vinyl pyridine group or vinyl trimethylsilylethyl group under conditions whereby an ethylpyridine group or trimethylsilylethyl group is added to the sulfur atom.

This subunit also generally contains a functional moiety for attachment of additional subunits, and thus additional subunits are attached to form the conductive oligomer. The conductive oligomer is then attached to a nucleoside, and additional nucleosides attached. The protecting group is then removed and the sulfur-gold covalent attachment is made. Alternatively, all or part of the conductive oligomer is made, and then either a subunit containing a protected sulfur atom is added, or a sulfur atom is added and then protected. The conductive oligomer is then attached to a nucleoside, and additional nucleosides attached. Alternatively, the conductive oligomer attached to a nucleic acid is made, and then either a subunit containing a protected sulfur atom is added, or a sulfur atom is added and then protected. Alternatively, the ethyl pyridine protecting group may be used as above, but removed after one or more steps and replaced with a standard protecting group like a disulfide. Thus, the ethyl pyridine or trimethylsilylethyl group may serve as the protecting group for some of the synthetic reactions, and then removed and replaced with a traditional protecting group.

By "subunit" of a conductive polymer herein is meant at least the moiety of the conductive oligomer to which the sulfur atom is attached, although additional atoms may be present, including either functional groups which allow the addition of additional components of the conductive oligomer, or additional components of the conductive oligomer. Thus, for example, when Structure 1 oligomers are used, a subunit comprises at least the first Y group.

A preferred method comprises 1) adding an ethyl pyridine or trimethylsilylethyl protecting group to a sulfur atom attached to a first subunit of a conductive oligomer, generally done by adding a vinyl pyridine or trimethylsilylethyl group to a sulfhydryl; 2) adding additional subunits to form the conductive oligomer; 3) adding at least a first nucleoside to the conductive oligomer; 4) adding additional nucleosides to the first nucleoside to form a nucleic acid; 5) attaching the conductive oligomer to the gold electrode. This may also be done in the absence of nucleosides.

The above methods may also be used to attach insulator molecules to a gold electrode, and moieties comprising capture binding ligands.

In a preferred embodiment, a monolayer comprising conductive oligomers (and preferably insulators) is added to the electrode. Generally, the chemistry of addition is similar to or the same as the addition of conductive oligomers to the electrode, i.e. using a sulfur atom for attachment to a gold electrode, etc. Compositions comprising monolayers in addition to the conductive oligomers covalently attached to nucleic acids may be made in at least one of five ways: (1) addition of the monolayer, followed by subsequent addition of the attachment linker-nucleic acid complex; (2) addition of the attachment linker-nucleic acid complex followed by addition of the monolayer; (3) simultaneous addition of the monolayer and attachment linker-nucleic acid complex; (4) formation of a monolayer (using any of 1, 2 or 3) which includes attachment linkers which terminate in a functional moiety suitable for attachment of a completed nucleic acid; or (5) formation of a monolayer which includes attachment linkers which terminate in a functional moiety suitable for nucleic acid synthesis, i.e. the nucleic acid is synthesized on the surface of the monolayer as is known in the art. Such suitable functional moieties include, but are not limited to, nucleosides, amino groups, carboxyl groups, protected sulfur moieties, or hydroxyl groups for phosphoramidite additions. The examples describe the formation of a monolayer on a gold electrode using the preferred method (1).

In a preferred embodiment, the nucleic acid is a peptide nucleic acid or analog. In this embodiment, the invention provides peptide nucleic acids with at least one covalently attached ETM or attachment linker. In a preferred embodiment, these moieties are covalently attached to an monomeric subunit of the PNA. By "monomeric subunit of PNA" herein is meant the —NH—$CH_2CH_2$—N($COCH_2$-Base)—$CH_2$—CO— monomer, or derivatives (herein included within the definition of —nucleoside") of PNA. For example, the number of carbon atoms in the PNA backbone may be altered; see generally Nielsen et al., Chem. Soc. Rev. 1997 page 73, which discloses a number of PNA derivatives, herein expressly incorporated by reference. Similarly, the amide bond linking the base to the backbone may be altered; phosphoramide and sulfuramide bonds may be used. Alternatively, the moieties are attached to an internal monomeric subunit. By "internal" herein is meant that the monomeric subunit is not either the N-terminal monomeric subunit or the C-terminal monomeric subunit. In this embodiment, the moieties can be attached either to a base or to the backbone of the monomeric subunit. Attachment to the base is done as outlined herein or known in the literature. In general, the moieties are added to a base which is then incorporated into a PNA as outlined herein. The base may be either protected, as required for incorporation into the PNA synthetic reaction, or derivatized, to allow incorporation, either prior to the addition of the chemical substituent or afterwards. Protection and derivatization of the bases is shown in the Figures. The bases can then be incorporated into monomeric subunits; the figures depict two different chemical substituents, an ETM and a conductive oligomer, attached at a base.

In a preferred embodiment, the moieties are covalently attached to the backbone of the PNA monomer. The attachment is generally to one of the unsubstituted carbon atoms of the monomeric subunit, preferably the α-carbon of the backbone, as is depicted in the Figures, although attachment at either of the carbon 1 or 2 positions, or the α-carbon of the amide bond linking the base to the backbone may be done. In the case of PNA analogs, other carbons or atoms may be substituted as well. In a preferred embodiment, moieties are added at the α-carbon atoms, either to a terminal monomeric subunit or an internal one.

In this embodiment, a modified monomeric subunit is synthesized with an ETM or an attachment linker, or a functional group for its attachment, and then the base is added and the modified monomer can be incorporated into a growing PNA chain. The figures depict the synthesis of a conductive oligomer covalently attached to the backbone of a PNA monomeric subunit, and the synthesis of a ferrocene attached to the backbone of a monomeric subunit.

Once generated, the monomeric subunits with covalently attached moieties are incorporated into a PNA using the techniques outlined in Will et al., Tetrahedron 51(44):12069–12082 (1995), and Vanderlaan et al., Tett. Let. 38:2249–2252 (1997), both of which are hereby expressly incorporated in their entirety. These procedures allow the addition of chemical substituents to peptide nucleic acids without destroying the chemical substituents.

As will be appreciated by those in the art, electrodes may be made that have any combination of nucleic acids, conductive oligomers and insulators.

The compositions of the invention may additionally contain one or more labels at any position. By "label" herein is meant an element (e.g. an isotope) or chemical compound that is attached to enable the detection of the compound. Preferred labels are radioactive isotopic labels, and colored or fluorescent dyes. The labels may be incorporated into the compound at any position. In addition, the compositions of the invention may also contain other moieties such as cross-linking agents to facilitate cross-linking of the target-probe complex. See for example, Lukhtanov et al., Nucl. Acids. Res. 24(4):683 (1996) and Tabone et al., Biochem. 33:375 (1994), both of which are expressly incorporated by reference.

Once made, the compositions find use in a number of applications, as described herein. In particular, the compositions of the invention find use in target analyte assays. As will be appreciated by those in the art, electrodes can be made that have a single species of binding ligands such as nucleic acid, i.e. a single binding ligand, or multiple binding ligand species.

In addition, as outlined herein, the use of a solid support such as an electrode enables the use of these probes in an array form. The use of oligonucleotide arrays are well known in the art, and the methods and compositions herein allow the use of array formats for other target analytes as well. In addition, techniques are known for "addressing" locations within an electrode and for the surface modification of electrodes. Thus, in a preferred embodiment, arrays of different binding ligands are laid down on the electrode, each of which are covalently attached to the electrode via a conductive linker. In this embodiment, the number of different species may vary widely, from one to thousands, with from about 4 to about 100,000 being preferred, and from about 10 to about 10,000 being particularly preferred.

The invention finds use in the screening of candidate bioactive agents for therapeutic agents that can alter the binding of the analyte to the binding ligand, and thus may be involved in biological function. The term "agent" or "exogeneous compound" as used herein describes any molecule, e.g., protein, oligopeptide, small organic molecule, polysaccharide, polynucleotide, etc., with the capability of directly or indirectly altering target analyte binding. Generally a plurality of assay mixtures are run in parallel with different agent concentrations to obtain a differential response to the various concentrations. Typically, one of these concentrations serves as a negative control, i.e., at zero concentration or below the level of detection.

Candidate agents encompass numerous chemical classes, though typically they are organic molecules, preferably small organic compounds having a molecular weight of more than 100 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Particularly preferred are peptides.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

Candidate agents may be added either before or after the target analyte.

Once the assay complexes of the invention are made, that minimally comprise a target sequence and a label probe, detection proceeds with electronic initiation. Without being limited by the mechanism or theory, detection is based on the transfer of electrons from the ETM to the electrode.

Detection of electron transfer, i.e. the presence of the ETMs, is generally initiated electronically, with voltage being preferred. A potential is applied to the assay complex. Precise control and variations in the applied potential can be via a potentiostat and either a three electrode system (one reference, one sample (or working) and one counter electrode) or a two electrode system (one sample and one counter electrode). This allows matching of applied potential to peak potential of the system which depends in part on the choice of ETMs and in part on the conductive oligomer used, the composition and integrity of the monolayer, and what type of reference electrode is used. As described herein, ferrocene is a preferred ETM.

In a preferred embodiment, a co-reductant or co-oxidant (collectively, co-redoxant) is used, as an additional electron source or sink. See generally Sato et al., Bull. Chem. Soc. Jpn 66:1032 (1993); Uosaki et al., Electrochemical Acta 36:1799 (1991); and Alleman et al., J. Phys. Chem 100:17050 (1996); all of which are incorporated by reference.

In a preferred embodiment, an input electron source in solution is used in the initiation of electron transfer, preferably when initiation and detection are being done using DC current or at AC frequencies where diffusion is not limiting. In general, as will be appreciated by those in the art, preferred embodiments utilize monolayers that contain a minimum of "holes", such that short-circuiting of the system is avoided. This may be done in several general ways. In a preferred embodiment, an input electron source is used that has a lower or similar redox potential than the ETM of the label probe. Thus, at voltages above the redox potential of the input electron source, both the ETM and the input electron source are oxidized and can thus donate electrons; the ETM donates an electron to the electrode and the input source donates to the ETM. For example, ferrocene, as a ETM attached to the compositions of the invention as described in the examples, has a redox potential of roughly 200 mV in aqueous solution (which can change significantly depending on what the ferrocene is bound to, the manner of the linkage and the presence of any substitution groups). Ferrocyanide, an electron source, has a redox potential of roughly 200 mV as well (in aqueous solution). Accordingly, at or above voltages of roughly 200 mV, ferrocene is converted to ferricenium, which then transfers an electron to the electrode. Now the ferricyanide can be oxidized to transfer an electron to the ETM. In this way, the electron source (or co-reductant) serves to amplify the signal generated in the system, as the electron source molecules rapidly and repeatedly donate electrons to the ETM attached to the nucleic acid. The rate of electron donation or acceptance will be limited by the rate of diffusion of the co-reductant, the electron transfer between the co-reductant and the ETM, which in turn is affected by the concentration and size, etc.

Alternatively, input electron sources that have lower redox potentials than the ETM are used. At voltages less than the redox potential of the ETM, but higher than the redox potential of the electron source, the input source such as ferrocyanide is unable to be oxidized and thus is unable to donate an electron to the ETM; i.e. no electron transfer occurs. Once ferrocene is oxidized, then there is a pathway for electron transfer.

In an alternate preferred embodiment, an input electron source is used that has a higher redox potential than the ETM of the label probe. For example, luminol, an electron source, has a redox potential of roughly 720 mV. At voltages higher than the redox potential of the ETM, but lower than the redox potential of the electron source, i.e. 200–720 mV, the ferrocene is oxidized, and transfers a single electron to the electrode via the conductive oligomer. However, the ETM is unable to accept any electrons from the luminol electron source, since the voltages are less than the redox potential of the luminol. However, at or above the redox potential of luminol, the luminol then transfers an electron to the ETM, allowing rapid and repeated electron transfer. In this way, the electron source (or co-reductant) serves to amplify the signal generated in the system, as the electron source molecules rapidly and repeatedly donate electrons to the ETM of the label probe.

Luminol has the added benefit of becoming a chemiluminiscent species upon oxidation (see Jirka et al., Analytica Chimica Acta 284:345 (1993)), thus allowing photo-detection of electron transfer from the ETM to the electrode. Thus, as long as the luminol is unable to contact the electrode directly, i.e. in the presence of the SAM such that there is no efficient electron transfer pathway to the electrode, luminol can only be oxidized by transferring an electron to the ETM on the label probe. When the ETM is not present, i.e. when the target sequence is not hybridized to the composition of the invention, luminol is not significantly oxidized, resulting in a low photon emission and thus a low (if any) signal from the luminol. In the presence of the target, a much larger signal is generated. Thus, the measure of luminol oxidation by photon emission is an indirect measurement of the ability of the ETM to donate electrons to the electrode. Furthermore, since photon detection is generally more sensitive than electronic detection, the sensitivity of the system may be increased. Initial results suggest that luminescence may depend on hydrogen peroxide concentration, pH, and luminol concentration, the latter of which appears to be non-linear.

Suitable electron source molecules are well known in the art, and include, but are not limited to, ferricyanide, and luminol.

Alternatively, output electron acceptors or sinks could be used, i.e. the above reactions could be run in reverse, with the ETM such as a metallocene receiving an electron from the electrode, converting it to the metallicenium, with the output electron acceptor then accepting the electron rapidly and repeatedly. In this embodiment, cobalticenium is the preferred ETM.

The presence of the ETMs at the surface of the monolayer can be detected in a variety of ways. A variety of detection methods may be used, including, but not limited to, optical detection (as a result of spectral changes upon changes in redox states), which includes fluorescence, phosphorescence, luminiscence, chemiluminescence, electrochemiluminescence, and refractive index; and electronic detection, including, but not limited to, amperommetry, voltammetry, capacitance and impedance. These methods include time or frequency dependent methods based on AC or DC currents, pulsed methods, lock-in techniques, filtering (high pass, low pass, band pass), and time-resolved techniques including time-resolved fluorescence.

In one embodiment, the efficient transfer of electrons from the ETM to the electrode results in stereotyped changes in the redox state of the ETM. With many ETMs including the complexes of ruthenium containing bipyridine, pyridine and imidazole rings, these changes in redox state are associated with changes in spectral properties. Significant differences in absorbance are observed between reduced and oxidized states for these molecules. See for example Fabbrizzi et al., Chem. Soc. Rev. 1995 pp 197–202). These differences can be monitored using a spectrophotometer or simple photomultiplier tube device.

In this embodiment, possible electron donors and acceptors include all the derivatives listed above for photoactivation or initiation. Preferred electron donors and acceptors have characteristically large spectral changes upon oxidation and reduction resulting in highly sensitive monitoring of electron transfer. Such examples include $Ru(NH_3)_4py$ and $Ru(bpy)_2im$ as preferred examples. It should be understood that only the donor or acceptor that is being monitored by absorbance need have ideal spectral characteristics.

In a preferred embodiment, the electron transfer is detected fluorometrically. Numerous transition metal complexes, including those of ruthenium, have distinct fluorescence properties. Therefore, the change in redox state of the electron donors and electron acceptors attached to the nucleic acid can be monitored very sensitively using fluorescence, for example with $Ru(4,7-biphenyl_2-phenanthroline)_3^{2+}$. The production of this compound can be easily measured using standard fluorescence assay techniques. For example, laser induced fluorescence can be recorded in a standard single cell fluorimeter, a flow through "on-line" fluorimeter (such as those attached to a chromatography system) or a multi-sample "plate-reader" similar to those marketed for 96-well immuno assays.

Alternatively, fluorescence can be measured using fiber optic sensors with nucleic acid probes in solution or attached to the fiber optic. Fluorescence is monitored using a photomultiplier tube or other light detection instrument attached to the fiber optic. The advantage of this system is the extremely small volumes of sample that can be assayed.

In addition, scanning fluorescence detectors such as the FluorImager sold by Molecular Dynamics are ideally suited to monitoring the fluorescence of modified nucleic acid molecules arrayed on solid surfaces. The advantage of this system is the large number of electron transfer probes that can be scanned at once using chips covered with thousands of distinct nucleic acid probes.

Many transition metal complexes display fluorescence with large Stokes shifts. Suitable examples include bis- and trisphenanthroline complexes and bis- and trisbipyridyl complexes of transition metals such as ruthenium (see Juris, A., Balzani, V., et. al. Coord. Chem. Rev., V. 84, p. 85–277, 1988).

Preferred examples display efficient fluorescence (reasonably high quantum yields) as well as low reorganization energies. These include $Ru(4,7-biphenyl_2-phenanthroline)_3^{2+}$, $Ru(4,4'-diphenyl-2,2'-bipyridine)_3^{2+}$ and platinum complexes (see Cummings et al., J. Am. Chem. Soc. 118:1949–1960 (1996), incorporated by reference). Alternatively, a reduction in fluorescence associated with hybridization can be measured using these systems.

In a further embodiment, electrochemiluminescence is used as the basis of the electron transfer detection. With some ETMs such as $Ru^{2+}(bpy)_3$, direct luminescence accompanies excited state decay. Changes in this property are associated with nucleic acid hybridization and can be monitored with a simple photomultiplier tube arrangement (see Blackburn, G. F. Clin. Chem. 37: 1534–1539 (1991); and Juris et al., supra.

In a preferred embodiment, electronic detection is used, including amperommetry, voltammetry, capacitance, and impedance. Suitable techniques include, but are not limited to, electrogravimetry; coulometry. (including controlled potential coulometry and constant current coulometry); voltametry (cyclic voltametry, pulse voltametry (normal pulse voltametry, square wave voltametry, differential pulse voltametry, Osteryoung square wave voltametry, and coulostatic pulse techniques); stripping analysis (aniodic stripping analysis, cathiodic stripping analysis, square wave stripping voltammetry); conductance measurements (electrolytic conductance, direct analysis); time-dependent electrochemical analyses (chronoamperometry, chronopotentiometry, cyclic chronopotentiometry and amperometry, AC polography, chronogalvametry, and chronocoulometry); AC impedance measurement; capacitance measurement; AC voltametry; and photoelectrochemistry.

In a preferred embodiment, monitoring electron transfer is via amperometric detection. This method of detection involves applying a potential (as compared to a separate reference electrode) between the nucleic acid-conjugated electrode and a reference (counter) electrode in the sample containing target genes of interest. Electron transfer of differing efficiencies is induced in samples in the presence or absence of target nucleic acid; that is, the presence or absence of the target nucleic acid, and thus the label probe, can result in different currents..

The device for measuring electron transfer amperometrically involves sensitive current detection and includes a means of controlling the voltage potential, usually a potentiostat. This voltage is optimized with reference to the potential of the electron donating complex on the label probe. Possible electron donating complexes include those previously mentioned with complexes of iron, osmium, platinum, cobalt, rhenium and ruthenium being preferred and complexes of iron being most preferred.

In a preferred embodiment, alternative electron detection modes are utilized. For example, potentiometric (or voltammetric) measurements involve non-faradaic (no net current flow) processes and are utilized traditionally in pH and other ion detectors. Similar sensors are used to monitor electron transfer between the ETM and the electrode. In addition, other properties of insulators (such as resistance) and of conductors (such as conductivity, impedance and capacitance) could be used to monitor electron transfer between ETM and the electrode. Finally, any system that generates a current (such as electron transfer) also generates a small magnetic field, which may be monitored in some embodiments.

It should be understood that one benefit of the fast rates of electron transfer observed in the compositions of the invention is that time resolution can greatly enhance the signal-to-noise results of monitors based on absorbance, fluorescence and electronic current. The fast rates of electron transfer of the present invention result both in high signals and stereotyped delays between electron transfer initiation and completion. By amplifying signals of particular delays, such as through the use of pulsed initiation of electron transfer and "lock-in" amplifiers of detection, and Fourier transforms.

In a preferred embodiment, electron transfer is initiated using alternating current (AC) methods. Without being bound by theory, it appears that ETMs, bound to an electrode, generally respond similarly to an AC voltage across a circuit containing resistors and capacitors. Basically, any methods which enable the determination of the nature of these complexes, which act as a resistor and capacitor, can be used as the basis of detection. Surprisingly, traditional electrochemical theory, such as exemplified in Laviron et al., J. Electroanal. Chem. 97:135 (1979) and Laviron et al., J. Electroanal. Chem. 105:35 (1979), both of which are incorporated by reference, do not accurately model the systems described herein, except for very small $E_{AC}$ (less than 10 mV) and relatively large numbers of molecules. That is, the AC current (I) is not accurately described by Laviron's equation. This may be due in part to the fact that this theory assumes an unlimited source and sink of electrons, which is not true in the present systems.

Accordingly, alternate equations were developed, using the Nernst equation and first principles to develop a model which more closely simulates the results. This was derived as follows. The Nernst equation, Equation 1 below, describes the ratio of oxidized (O) to reduced (R) molecules (number of molecules=n) at any given voltage and temperature, since not every molecule gets oxidized at the same oxidation potential.

Equation 1

$$E_{DC} = E_0 + \frac{RT}{nF}\ln\frac{[O]}{[R]} \quad (1)$$

$E_{DC}$ is the electrode potential, $E_0$ is the formal potential of the metal complex, R is the gas constant, T is the temperature in degrees Kelvin, n is the number of electrons transferred, F is faraday's constant, [O] is the concentration of oxidized molecules and [R] is the concentration of reduced molecules.

The Nernst equation can be rearranged as shown in Equations 2 and 3:

Equation 2

$$E_{DC} - E_0 = \frac{RT}{nF}\ln\frac{[O]}{[R]} \quad (2)$$

$E_{DC}$ is the DC component of the potential.

Equation 3

$$\exp\frac{nF}{RT}(E_{DC}-E_0) = \frac{[O]}{[R]} \quad (3)$$

Equation 3 can be rearranged as follows, using normalization of the concentration to equal 1 for simplicity, as shown in Equations 4, 5 and 6. This requires the subsequent multiplication by the total number of molecules.

[O]+[R]=1          Equation 4

[O]=1−[R]          Equation 5

[R]=1−[O]          Equation 6

Plugging Equation 5 and 6 into Equation 3, and the fact that nF/RT equals 38.9 $V^{-1}$, for n=1, gives Equations 7 and 8, which define [O] and [R], respectively:

Equation 7

$$[O] = \frac{\exp^{38.9(E-E_0)}}{1+\exp^{38.9(E-E_0)}} \quad (4)$$

Equation 8

$$[R] = \frac{1}{1+\exp^{38.9(E-E_0)}} \quad (5)$$

Taking into consideration the generation of an AC faradaic current, the ratio of [O]/[R] at any given potential must be evaluated. At a particular $E_{DC}$ with an applied $E_{AC}$, as is generally described herein, at the apex of the $E_{AC}$ more molecules will be in the oxidized state, since the voltage on the surface is now ($E_{DC}+E_{AC}$); at the bottom, more will be reduced since the voltage is lower. Therefore, the AC current at a given $E_{DC}$ will be dictated by both the AC and DC voltages, as well as the shape of the Nernstian curve. Specifically, if the number of oxidized molecules at the bottom of the AC cycle is subtracted from the amount at the top of the AC cycle, the total change in a given AC cycle is obtained, as is generally described by Equation 9. Dividing by 2 then gives the AC amplitude.

Equation 9

$$i_{AC} \cong \frac{(\text{electrons at } [E_{DC}+E_{AC}]) - (\text{electrons at } [E_{DC}-E_{AC}])}{2}$$

Equation 10 thus describes the AC current which should result:

$$i_{AC}=C_0F\omega^{1/2}([O]_{E_{DC}+E_{AC}}-[O]_{E_{DC}-E_{AC}})(6) \quad \text{Equation 10}$$

As depicted in Equation 11, the total AC current will be the number of redox molecules C), times faraday's constant (F), times the AC frequency ($\omega$), times 0.5 (to take into account the AC amplitude), times the ratios derived above in Equation 7. The AC voltage is approximated by the average, $E_{AC}2/\pi$.

Equation 11

$$i_{AC} = \frac{C_0 F \omega}{2} \left( \frac{\exp^{38.9\left[E_{DC} + \frac{2E_{AC}}{\pi} - E_0\right]}}{1 + \exp^{38.9\left[E_{DC} + \frac{2E_{AC}}{\pi} - E_0\right]}} \right) - \frac{\exp^{38.9\left[E_{DC} - \frac{2E_{AC}}{\pi} - E_0\right]}}{1 + \exp^{38.9\left[E_{DC} - \frac{2E_{AC}}{\pi} - E\right]}} \quad (7)$$

Using Equation 11, simulations were generated using increasing overpotential (AC voltage). In some cases the current is smaller than predicted, however this has been shown to be caused by ferrocene degradation which may be remedied in a number of ways. However, Equation 11 does not incorporate the effect of electron transfer rate nor of instrument factors. Electron transfer rate is important when the rate is close to or lower than the applied frequency. Thus, the true $i_{AC}$ should be a function of all three, as depicted in Equation 12.

$$i_{AC} = f(\text{Nernst factors}) f(k_{ET}) f(\text{instrument factors}) \quad \text{Equation 12}$$

These equations can be used to model and predict the expected AC currents in systems which use input signals comprising both AC and DC components. As outlined above, traditional theory surprisingly does not model these systems at all, except for very low voltages.

In general, non-specifically bound label probes/ETMs show differences in impedance (i.e. higher impedances) than when the label probes containing the ETMs are specifically bound in the correct orientation. In a preferred embodiment, the non-specifically bound material is washed away, resulting in an effective impedance of infinity. Thus, AC detection gives several advantages as is generally discussed below, including an increase in sensitivity, and the ability to "filter out" background noise. In particular, changes in impedance (including, for example, bulk impedance) as between non-specific binding of ETM-containing probes and target-specific assay complex formation may be monitored.

Accordingly, when using AC initiation and detection methods, the frequency response of the system changes as a result of the presence of the ETM. By "frequency response" herein is meant a modification of signals as a result of electron transfer between the electrode and the ETM. This modification is different depending on signal frequency. A frequency response includes AC currents at one or more frequencies, phase shifts, DC offset voltages, faradaic impedance, etc.

Once the assay complex including the target sequence and label probe is made, a first input electrical signal is then applied to the system, preferably via at least the sample electrode (containing the complexes of the invention) and the counter electrode, to initiate electron transfer between the electrode and the ETM. Three electrode systems may also be used, with the voltage applied to the reference and working electrodes. The first input signal comprises at least an AC component. The AC component may be of variable amplitude and frequency. Generally, for use in the present methods, the AC amplitude ranges from about 1 mV to about 1.1 V, with from about 10 mV to about 800 mV being preferred, and from about 10 mV to about 500 mV being especially preferred. The AC frequency ranges from about 0.01 Hz to about 100 MHz, with from about 10 Hz to about 10 MHz being preferred, and from about 100 Hz to about 20 MHz being especially preferred.

The use of combinations of AC and DC signals gives a variety of advantages, including surprising sensitivity and signal maximization.

In a preferred embodiment, the first input signal comprises a DC component and an AC component. That is, a DC offset voltage between the sample and counter electrodes is swept through the electrochemical potential of the ETM (for example, when ferrocene is used, the sweep is generally from 0 to 500 mV) (or alternatively, the working electrode is grounded and the reference electrode is swept from 0 to −500 mV). The sweep is used to identify the DC voltage at which the maximum response of the system is seen. This is generally at or about the electrochemical potential of the ETM. Once this voltage is determined, either a sweep or one or more uniform DC offset voltages may be used. DC offset voltages of from about −1 V to about +1.1 V are preferred, with from about −500 mV to about +800 mV being especially preferred, and from about −300 mV to about 500 mV being particularly preferred. In a preferred embodiment, the DC offset voltage is not zero. On top of the DC offset voltage, an AC signal component of variable amplitude and frequency is applied. If the ETM is present, and can respond to the AC perturbation, an AC current will be produced due to electron transfer between the electrode and the ETM.

For defined systems, it may be sufficient to apply a single input signal to differentiate between the presence and absence of the ETM (i.e. the presence of the target sequence) nucleic acid. Alternatively, a plurality of input signals are applied. As outlined herein, this may take a variety of forms, including using multiple frequencies, multiple DC offset voltages, or multiple AC amplitudes, or combinations of any or all of these.

Thus, in a preferred embodiment, multiple DC offset voltages are used, although as outlined above, DC voltage sweeps are preferred. This may be done at a single frequency, or at two or more frequencies.

In a preferred embodiment, the AC amplitude is varied. Without being bound by theory, it appears that increasing the amplitude increases the driving force. Thus, higher amplitudes, which result in higher overpotentials give faster rates of electron transfer. Thus, generally, the same system gives an improved response (i.e. higher output signals) at any single frequency through the use of higher overpotentials at that frequency. Thus, the amplitude may be increased at high frequencies to increase the rate of electron-transfer through the system, resulting in greater sensitivity. In addition, this may be used, for example, to induce responses in slower systems such as those that do not possess optimal spacing configurations.

In a preferred embodiment, measurements of the system are taken at at least two separate amplitudes or overpotentials, with measurements at a plurality of amplitudes being preferred. As noted above, changes in response as a result of changes in amplitude may form the basis of identification, calibration and quantification of the system. In addition, one or more AC frequencies can be used as well.

In a preferred embodiment, the AC frequency is varied. At different frequencies, different molecules respond in different ways. As will be appreciated by those in the art, increasing the frequency generally increases the output current. However, when the frequency is greater than the rate at which electrons may travel between the electrode and the ETM, higher frequencies result in a loss or decrease of output signal. At some point, the frequency will be greater than the rate of electron transfer between the ETM and the electrode, and then the output signal will also drop.

In one embodiment, detection utilizes a single measurement of output signal at a single frequency. That is, the frequency response of the system in the absence of target sequence, and thus the absence of label probe containing ETMs, can be previously determined to be very low at a particular high frequency. Using this information, any response at a particular frequency, will show the presence of the assay complex. That is, any response at a particular frequency is characteristic of the assay complex. Thus, it may only be necessary to use a single input high frequency, and any changes in frequency response is an indication that the ETM is present, and thus that the target sequence is present.

In addition, the use of AC techniques allows the significant reduction of background signals at any single frequency due to entities other than the ETMs, i.e. "locking out" or "filtering" unwanted signals. That is, the frequency response of a charge carrier or redox active molecule in solution will be limited by its diffusion coefficient and charge transfer coefficient. Accordingly, at high frequencies, a charge carrier may not diffuse rapidly enough to transfer its charge to the electrode, and/or the charge transfer kinetics may not be fast enough. This is particularly significant in embodiments that do not have good monolayers, i.e. have partial or insufficient monolayers, i.e. where the solvent is accessible to the electrode. As outlined above, in DC techniques, the presence of "holes" where the electrode is accessible to the solvent can result in solvent charge carriers "short circuiting" the system, i.e. the reach the electrode and generate background signal. However, using the present AC techniques, one or more frequencies can be chosen that prevent a frequency response of one or more charge carriers in solution, whether or not a monolayer is present. This is particularly significant since many biological fluids such as blood contain significant amounts of redox active molecules which can interfere with amperometric detection methods.

In a preferred embodiment, measurements of the system are taken at at least two separate frequencies, with measurements at a plurality of frequencies being preferred. A plurality of frequencies includes a scan. For example, measuring the output signal, e.g., the AC current, at a low input frequency such as 1–20 Hz, and comparing the response to the output signal at high frequency such as 10–100 kHz will show a frequency response difference between the presence and absence of the ETM. In a preferred embodiment, the frequency response is determined at at least two, preferably at least about five, and more preferably at least about ten frequencies.

After transmitting the input signal to initiate electron transfer, an output signal is received or detected. The presence and magnitude of the output signal will depend on a number of factors, including the overpotential/amplitude of the input signal; the frequency of the input AC signal; the composition of the intervening medium; the DC offset; the environment of the system; the nature of the ETM; the solvent; and the type and concentration of salt. At a given input signal, the presence and magnitude of the output signal will depend in general on the presence or absence of the ETM, the placement and distance of the ETM from the surface of the monolayer and the character of the input signal. In some embodiments, it may be possible to distinguish between non-specific binding of label probes and the formation of target specific assay complexes containing label probes, on the basis of impedance.

In a preferred embodiment, the output signal comprises an AC current. As outlined above, the magnitude of the output current will depend on a number of parameters. By varying these parameters, the system may be optimized in a number of ways.

In general, AC currents generated in the present invention range from about 1 femtoamp to about 1 milliamp, with currents from about 50 femtoamps to about 100 microamps being preferred, and from about 1 picoamp to about 1 microamp being especially preferred.

In a preferred embodiment, the output signal is phase shifted in the AC component relative to the input signal. Without being bound by theory, it appears that the systems of the present invention may be sufficiently uniform to allow phase-shifting based detection. That is, the complex biomolecules of the invention through which electron transfer occurs react to the AC input in a homogeneous manner, similar to standard electronic components, such that a phase shift can be determined. This may serve as the basis of detection between the presence and absence of the ETM, and/or differences between the presence of target-specific assay complexes comprising label probes and non-specific binding of the label probes to the system components.

The output signal is characteristic of the presence of the ETM; that is, the output signal is characteristic of the presence of the target-specific assay complex comprising label probes and ETMs. In a preferred embodiment, the basis of the detection is a difference in the faradaic impedance of the system as a result of the formation of the assay complex. Faradaic impedance is the impedance of the system between the electrode and the ETM. Faradaic impedance is quite different from the bulk or dielectric impedance, which is the impedance of the bulk solution between the electrodes. Many factors may change the faradaic impedance which may not effect the bulk impedance, and vice versa.

Thus, the assay complexes comprising the nucleic acids in this system have a certain faradaic impedance, that will depend on the distance between the ETM and the electrode, their electronic properties, and the composition of the intervening medium, among other things. Of importance in the methods of the invention is that the faradaic impedance between the ETM and the electrode is significantly different depending on whether the label probes containing the ETMs are specifically or non-specifically bound to the electrode.

Accordingly, the present invention further provides apparatus for the detection of nucleic acids using AC detection methods. The apparatus includes a test chamber which has at least a first measuring or sample electrode, and a second measuring or counter electrode. Three electrode systems are also useful. The first and second measuring electrodes are in contact with a test sample receiving region, such that in the presence of a liquid test sample, the two electrodes may be in electrical contact.

In a preferred embodiment, the first measuring electrode comprises a single stranded nucleic acid capture probe covalently attached via an attachment linker, and a monolayer comprising conductive oligomers, such as are described herein.

The apparatus further comprises an AC voltage source electrically connected to the test chamber; that is, to the measuring electrodes. Preferably, the AC voltage source is capable of delivering DC offset voltage as well.

In a preferred embodiment, the apparatus further comprises a processor capable of comparing the input signal and the output signal. The processor is coupled to the electrodes and configured to receive an output signal, and thus detect the presence of the target nucleic acid.

Thus, the compositions of the present invention may be used in a variety of research, clinical, quality control, or field testing settings.

In a preferred embodiment, the probes are used in genetic diagnosis. For example, probes can be made using the techniques disclosed herein to detect target sequences such as the gene for nonpolyposis colon cancer, the BRCA1 breast cancer gene, P53, which is a gene associated with a variety of cancers, the Apo E4 gene that indicates a greater risk of Alzheimer's disease, allowing for easy presymptomatic screening of patients, mutations in the cystic fibrosis gene, or any of the others well known in the art.

In an additional embodiment, viral and bacterial detection is done using the complexes of the invention. In this embodiment, probes are designed to detect target sequences from a variety of bacteria and viruses. For example, current blood-screening techniques rely on the detection of anti-HIV antibodies. The methods disclosed herein allow for direct screening of clinical samples to detect HIV nucleic acid sequences, particularly highly conserved HIV sequences. In addition, this allows direct monitoring of circulating virus within a patient as an improved method of assessing the efficacy of anti-viral therapies. Similarly, viruses associated with leukemia, HTLV-I and HTLV-II, may be detected in this way. Bacterial infections such as tuberculosis, clymidia and other sexually transmitted diseases, may also be detected.

In a preferred embodiment, the nucleic acids of the invention find use as probes for toxic bacteria in the screening of water and food samples. For example, samples may be treated to lyse the bacteria to release its nucleic acid, and then probes designed to recognize bacterial strains, including, but not limited to, such pathogenic strains as, Salmonella, Campylobacter, *Vibrio cholerae,* Leishmania, enterotoxic strains of *E. coli,* and Legionnaire's disease bacteria. Similarly, bioremediation strategies may be evaluated using the compositions of the invention.

In a further embodiment, the probes are used for forensic "DNA fingerprinting" to match crime-scene DNA against samples taken from victims and suspects.

In an additional embodiment, the probes in an array are used for sequencing by hybridization.

Thus, the present invention provides for extremely specific and sensitive probes, which may, in some embodiments, detect target sequences without removal of unhybridized probe. This will be useful in the generation of automated gene probe assays.

Alternatively, the compositions of the invention are useful to detect successful gene amplification in PCR, thus allowing successful PCR reactions to be an indication of the presence or absence of a target sequence. PCR may be used in this manner in several ways. For example, in one embodiment, the PCR reaction is done as is known in the art, and then added to a composition of the invention comprising the target nucleic acid with a ETM, covalently attached to an electrode via a conductive oligomer with subsequent detection of the target sequence. Alternatively, PCR is done using nucleotides labelled with a ETM, either in the presence of, or with subsequent addition to, an electrode with a conductive oligomer and a target nucleic acid. Binding of the PCR product containing ETMs to the electrode composition will allow detection via electron transfer. Finally, the nucleic acid attached to the electrode via a conductive polymer may be one PCR primer, with addition of a second primer labelled with an ETM. Elongation results in double stranded nucleic acid with a ETM and electrode covalently attached. In this way, the present invention is used for PCR detection of target sequences.

In a preferred embodiment, the arrays are used for mRNA detection. A preferred embodiment utilizes either capture probes or capture extender probes that hybridize close to the 3' polyadenylation tail of the mRNAs. This allows the use of one species of target binding probe for detection, i.e. the probe contains a poly-T portion that will bind to the poly-A tail of the mRNA target. Generally, the probe will contain a second portion, preferably non-poly-T, that will bind to the detection probe (or other probe). This allows one target-binding probe to be made, and thus decreases the amount of different probe synthesis that is done.

In a preferred embodiment, the use of restriction enzymes and ligation methods allows the creation of "universal" arrays. In this embodiment, monolayers comprising capture probes that comprise restriction endonuclease ends, are used. By utilizing complementary portions of nucleic acid, while leaving "sticky ends", an array comprising any number of restriction endonuclease sites is made. Treating a target sample with one or more of these restriction endonucleases allows the targets to bind to the array. This can be done without knowing the sequence of the target. The target sequences can be ligated, as desired, using standard methods such as ligases, and the target sequence detected, using either standard labels or the methods of the invention.

The present invention provides methods which can result in sensitive detection of nucleic acids. In a preferred embodiment, less than about $10 \times 10^5$ molecules are detected, with less than about $10 \times 10^5$ being preferred, less than $10 \times 10^4$ being particularly preferred, less than about $10 \times 10^3$ being especially preferred, and less than about $10 \times 10^2$ being most preferred. As will be appreciated by those in the art, this assumes a 1:1 correlation between target sequences and reporter molecules; if more than one reporter molecule (i.e. electron transfer moeity) is used for each target sequence, the sensitivity will go up.

While the limits of detection are currently being evaluated, based on the published electron transfer rate through DNA, which is roughly $1 \times 10^6$ electrons/sec/duplex for an 8 base pair separation (see Meade et al., Angw. Chem. Eng. Ed., 34:352 (1995)) and high driving forces, AC frequencies of about 100 kHz should be possible. As the preliminary results show, electron transfer through these systems is quite efficient, resulting in nearly $100 \times 10^3$ electrons/sec, resulting in potential femtoamp sensitivity for very few molecules.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference in their entirety.

EXAMPLES

Example 1

Synthesis of Nucleoside Modified with Ferrocene at the 2' Position

The preparation of N6 is described as shown in FIG. 9.

Compound N1. Ferrocene (20 g, 108 mmol) and 4-bromobutyl chloride (20 g, 108 mmol) were dissolved in 450 mL dichloromethane followed by the addition of $AlCl_3$ anhydrous (14.7 g, 11 mmol). The reaction mixture was stirred at room temperature for 1 hour and 40 minutes, then was quenched by addition of 600 mL ice. The organic layer was separated and was washed with water until the aqueous layer was close to neutral (pH=5). The organic layer was dried with $Na_2SO_4$ and concentrated. The crude product was purified by flash chromatography eluting with 50/50 hexane/dichloromethane and later 30/70 hexane/dichloromethane on 300 g silica gel to afford 26.4 gm (73%) of the title product.

Compound N2. Compound N1 (6 g, 18 mmol) was dissolved in 120 mL toluene in a round bottom flask zinc, (35.9 g, 55 mmol), mercuric chloride (3.3g, 12 mmol) and water (100 mL) were added successively. Then HCl solution (12 M, 80 mL) was added dropwise. The reaction mixture was stirred at room temperature for 16 hours. The organic layer was separated, and washed with water (2×100 mL) and concentrated. Further purification by flash chromatography (hexane) on 270 gm of silica gel provided the desired product as a brown solid (3.3 g, 58%).

Compound N3. A mixture of 13.6 gm (51 mmol) of adenosine in 400 mL dry DMF was cooled in a ice-water bath for 10 minutes before the addition of 3.0 gm (76 mmol) of NaH (60%). The reaction mixture was stirred at 0° C. for one hour before addition of Compound N2 (16.4 g, 51 mmol). Then the temperature was slowly raised to 30° C., and the reaction mixture was kept at this temperature for 4 hours before being quenched by 100 mL ice. The solvents were removed in vacuo. The resultant gum was dissolved in 300 mL water and 300 mL ethyl acetate. The aqueous layer was extracted thoroughly (3×300 mL ethyl acetate). The combined organic extracts. were concentrated, and the crude product was purified by flash chromatography on 270 g silica gel. The column was eluted with 20%ethyl acetate/dichloromethane, 50% ethyl acetate/dichloromethane, 70% ethyl acetate/dichloromethane, ethyl acetate, 1% methanol/ethyl acetate, 3% methanol/ethyl acetate, and 5% methanol/ethyl acetate. The concentration of the desired fractions provide the final product (6.5 g, 25%).

Compound N4. Compound N3 (6.5 g, 12.8 mmol) was dissolved in 150 mL dry pyridine, followed by adding TMSCI (5.6 g, 51.2 mmol). The reaction mixture was stirred at room temperature for 1.5 hours. Then phenoxyacetyl chloride (3.3 g, 19.2 mmol) was added at 0° C. The reaction was then stirred at room temperature for 4 hours and was quenched by the addition of 100 mL water at 0° C. The solvents were removed under reduced pressure, and the crude gum was further purified by flash chromatography on 90 g of silica gel (1% methanol/dichloromethane) (2.3 g, 28%).

Compound N5. Compound N4 (2.2 g, 3.4 mmol) and DMAP (200 mg, 1.6 mmol) were dissolved in 150 mL dry pyridine, followed by the addition of DMTCI (1.4 g, 4.1 mmol). The reaction was stirred under argon at room temperature overnight. The solvent was removed under reduced pressure, and the residue was dissolved in 250 mL dichloromethane. The organic solution was washed by 5% NaHCO$_3$ solution (3×250 mL), dried over Na$_2$SO$_4$, and concentrated. Further purification by flash chromatography on 55 g of silica gel (1% TEA/50% hexane/dichloromethane) provided the desired product (1.3 g, 41%).

Compound N6, To a solution of N5 (3.30 gm, 3.50 mmol) in 150 mL dichloromethane. Diisopropylethylamine (4.87 mL, 8.0 eq.) and catalytic amount of DMAP (200 mg) were added. The mixture was kept at 0° C., and N,N-diisopropylamino cyanoethyl phosphonamidic chloride (2.34 mL, 10.48 mmol) was added. The reaction mixture was warmed up and stirred at room temperature overnight. After dilution by adding 150 mL of dichloromethane and 250 mL of 5% NaHCO$_3$ aqueous solution, the organic layer was separated, washed with 5% NaHCO3 (250 mL), dried over Na$_2$SO$_4$, and concentrated. The crude product was purified on a flash column of 66 g of silica gel packed with 1% TEA in hexane. The eluting solvents were 1% TEA in hexane (500 mL), 1% TEA and 10% dichloromethane in hexane (500 mL), 1% TEA and 20% dichloromethane in hexane (500 mL). 1% TEA and 50% dichloromethane in hexane (500 mL). Fractions containing the desired products were collected and concentrated to afford the final product (3 gm, 75%).

Example 2

Synthesis of "Branched" Nucleoside

The synthesis of N17 is described as shown in FIG. 10.

Synthesis of N14. To a solution of Tert-butyldimethylsilyl chloride (33.38 g, 0.22 mol) in 300 mL of dichloromethane was added imidazole (37.69 g, 0.55 mol). Immediately, large amount of precipitate was formed. 2-Bromoethanol (27.68 g, 0.22 mol,) was added slowly at room temperature. The reaction mixture was stirred at this temperature for 3 hours. The organic layer was washed with water (200 mL), 5% NaHCO$_3$ (2×250 mL), and water (200 mL). The removal of solvent afforded 52.52 g of the title product (99%).

Synthesis of N15. To a suspension of adenosine (40 g, 0.15 mol) in 1.0 L of DMF at 0° C., was added NaH (8.98 gm of 60% in mineral oil, 0.22 mol). The mixture was stirred at 0° C. for 1 hour, and N14 (35.79 gm, 0.15mol) was added. The reaction was stirred at 30° C. overnight. It was quenched by 100 mL ice-water. The solvents were removed under high vacuum. The resultant foam was dissolved in a mixture of 800 mL of ethyl acetate and 700 mL of water. The aqueous layer was further extracted by ethyl acetate (3×200 mL). The combined organic layer was dried over Na$_2$SO$_4$ and concentrated. The crude product was further purified on a flash column of 300 g of silica gel packed with 1% TEA in dichloromethane. The eluting solvents were dichloromethane (500 mL), 3% MeOH in dichloromethane (500 mL), 5% MeOH in dichloromethane (500 mL), and 8% MeOH in dichloromethane (2000 mL). The desired fractions were collected and concentrated to afford 11.70 g of the title product (19%).

Synthesis of N16. To a solution of N15 (11.50 gm, 27.17 mmol) in 300 mL dry pyridine cooled at 0° C., was added trimethylsily chloride (13.71 mL, 0.11 mol, 4.0). The mixture was stirred at 0° C. for 40 min. Phenoxyacetyl chloride (9.38 mL, 67.93 mmol) was added. The reaction was stirred at 0° C. for 2.5 h. The mixture was then transferred to a mixture of 700 mL of dichloromethane and 500 mL water. The mixture was shaken well and organic layer was separated. After washing twice with 5% NaHCO$_3$ (2×300 mL), dichloromethane was removed on a rotovapor. Into the residue was added 200 mL of water, the resulting pyridine mixture was stirred at room temperature for 2 hours. The solvents were then removed under high vacuum. The gum product was co-evaporated with 100 mL of pyridine. The residue was dissolved in 250 mL of dry pyridine at 0° C., and 4,4'-dimethoxytrityl chloride (11.02 gm, 32.60 mmol) was added. The reaction was stirred at room temperature overnight. The solution was transferred to a mixture of 700 mL of dichloromethane and 500 mL of 5% NaHCO$_3$. After shaking well, the organic layer was separated, further washed with 5% NaHCO$_3$ (2×200 mL), and then concentrated. The crude product was purified on a flash column of 270 gm of silica gel packed with 1% TEA/30% CH$_2$Cl$_2$/Hexane. The eluting solvents were 1% TEA/50% CH$_2$Cl$_2$/Hexane (1000 mL), and 1% TEA/CH$_2$Cl$_2$ (2000 mL). The fractions containing the desired product were collected and concentrated to afford 10.0 g of the title product (43%).

Synthesis of N17. To a solution of N16 (10.0 gm, 11.60 mmol) in 300 mL dichloromethane. Diisopropylethylamine (16.2 mL) and catalytic amount of N,N-dimethylaminopyridine(200 mg) were added. The mixture was cooled in an ice-water bath, and N,N-diisopropylamino cyanoethyl phosphonamidic chloride (7.78 mL, 34.82 mmol) was added. The reaction was stirred at room temperature overnight. The reaction mixture was diluted by adding 250 mL of dichloromethane and 250 mL of 5% $NaHCO_3$. After shaking well, the organic layer was separated and washed once more with the same amount of 5% $NaHCO_3$ aqueous solution, dried over $Na_2SO_4$, and concentrated. The crude product was purified on a flash column of 120 gm of silica gel packed with 1% TEA and 10% dichloromethane in hexane. The eluting solvents were 1% TEA and 10% dichloromethane in hexane (500 mL), 1% TEA and 20% dichloromethane in hexane (500 mL), and 1% TEA and 40% dichloromethane in hexane (1500 mL). The right fractions were collected and concentrated to afford the final product (7.37 gm, 60%).

Example 3

Synthesis of Nucleoside with Ferrocene Attached Via a Phosphate

The synthesis of Y63 is described as shown in FIG. 11.

Synthesis of C102: A reaction mixture consisting of 10.5 gm (32.7 mmol) of N2, 16 gm of potassium acetate and 350 ml of DMF was stirred at 100° C. for 2.5 hrs. The reaction mixture was allowed to cool to room temperature and then poured into a mixture of 400 ml of ether and 800 ml of water. The mixture was shaken and the organic layer was separated. The aqueous layer was extracted twice with ether. The combined ether extracts were dried over sodium sulfate and then concentrated for column chromatography. Silica gel (160 gm) was packed with 1% TEA/Hexane. The crude was loaded and the column was eluted with 1% TEA/0–100% $CH_2Cl_2$/Hexane. Fractions containing desired product were collected and concentrated to afford 5.8 g (59.1%) of C102.

Synthesis of Y61: To a flask containing 5.1 gm (17.0 mmol) of C102 was added 30 ml of Dioxane. To this solution, small aliquots of 1M NaOH was added over a period of 2.5 hours or until hydrolysis was complete. After hydrolysis the product was extracted using hexane. The combined extracts were dried over sodium sulfate and concentrated for chromatography. Silica gel (100 gm) was packed in 10% EtOAc/Hexane. The crude product solution was loaded and the column was eluted with 10% to 50% EtOAc in hexane. The fractions containing desired product were pooled and concentrated to afford 4.20 gm (96.1%) of Y61.

Synthesis of Y62: To a flask containing 4.10 gm (15.9 mmol) of Y61 was added 200 ml of dichloromethane and 7.72 ml of DIPEA and 4.24 gm (15.9 mmol) of bis (diisopropylamino) chlorophosphine. This reaction mixture was stirred under the presence of argon overnight. After the reaction mixture was concentrated to ⅓ of its original volume, 200 ml of hexane was added and then the reaction mixture was again concentrated to ⅓ is original volume. This procedure was repeated once more. The precipitated salts were filtered off and the solution was concentrated to afford 8.24 gm of crude Y62. Without further purification, the product was used for next step.

Synthesis of Y63: A reaction mixture of 1.0 gm (1.45 mmol) of N-PAC deoxy-adenosine, 1.77 g of the crude Y62, and 125 mg of N,N-diisopropylammonium tetrazolide, and 100 ml of dichloromethane. The reaction mixture was stirred at room temperature overnight. The reaction mixture was then diluted by adding 100 ml of $CH_2Cl_2$ and 100 mL of 5% $NaHCO_3$ solution. The organic phase was separated and dried over sodium sulfate. The solution was then concentrated for column chromatography. Silica gel (35 gm) was packed with 1% TEA /Hexane. The crude material was eluted with 1% TEA /10–40% $CH_2Cl_2$/Hexane. The fractions containing product were pooled and concentrated to afford 0.25 gm of the title product.

Example 4

Synthesis of Ethylene Glycol Terminated Wire W71

As shown in FIG. 12.

Synthesis of W55: To a flask was added 7.5 gm (27.3 mmol) of tert-butyldiphenylchlorosilane, 25.0 gm (166.5 mmol) of tri(ethylene glycol) and 50 ml of dry DMF under argon. The mixture was stirred and cooled in an ice-water bath. To the flask was added dropwise a clear solution of 5.1 gm (30.0 mmol) of $AgNO_3$ in 80 mL of DMF through an additional funnel. After the completeness of addition, the mixture was allowed to warm up to room temperature and was stirred for additional 30 min. Brown AgCl precipitate was filtered out and washed with DMF(3×10 mL). The removal of solvent under reduced pressure resulted in formation of thick syrup-like liquid product that was dissolved in about 80 ml of $CH_2Cl_2$. The solution was washed with water (6×100 mL) in order to remove unreacted starting material, ie, tris (ethylene glycol), then dried over $Na_2SO4$. Removal of $CH_2Cl_2$ afforded~10.5 g crude product, which was purified on a column containing 104 g of silica gel packed with 50% $CH_2Cl_2$/hexane. The column was eluted with 3–5% $MeOH/CH_2Cl_2$. The fractions containing the desired product were pooled and concentrated to afford 8.01 gm (75.5%) of the pure title product.

Synthesis of W68: To a flask containing 8.01 gm (20.6.0 mmol) of W55 was added 8.56 gm (25.8 mmol) of $CBr_4$ and 60 ml of $CH_2Cl_2$. The mixture was stirred in an ice-water bath. To the solution was slowly added 8.11 gm (31.0 mmol) of $PPh_3$ in 15 ml $CH_2Cl_2$. The mixture was stirred for about 35 min. at 0° C., and allowed to warm to room temperature. The volume of the mixture was reduced to about 10.0 ml and 75 ml of ether was added. The precipitate was filtered out and washed with 2×75 of ether. Removal of ether gave about 15 gm of crude product that was used for purification. Silica gel (105 gm) was packed with hexane. Upon loading the sample solution, the column was eluted with 50 % $CH_2Cl_2$/hexane and then $CH_2Cl_2$. The desired fractions were pooled and concentrated to give 8.56 gm (72.0%) of pure title product.

Synthesis of W69: A solution of 5.2 gm (23.6 mmol)of 4-iodophenol in 50 ml of dry DMF was cooled in an ice-water bath under Ar. To the mixture was added 1.0 gm of NaH (60% in mineral oil, 25.0 mmol) portion by portion. The mixture was stirred at the same temperature for about 35 min. and at room temperature for 30 min. A solution of 8.68 gm (19.2 mmol) of W68 in 20 ml of DMF was added to the flask under argon. The mixture was stirred at 50° C. for 12 hr with the flask covered with aluminum foil. DMF was removed under reduced pressure. The residue was dissolved in 300 ml of ethyl acetate, and the solution was washed with $H_2O$ (6×50 mL). Ethyl acetate was removed under reduced pressure and the residue was loaded into a 100 g silica gel column packed with 30% $CH_2Cl_2$/hexane for the purification. The column was eluted with 30–100% $CH_2Cl_2$/hexane. The fractions containing the desired product were pooled and concentrated to afford 9.5 gm (84.0%) of the title product.

Synthesis of W70: To a 100 ml round bottom flask containing 6.89 gm (11.6 mmol) of W69 was added 30 ml of 1 M TBAF THF solution. The solution was stirred at room temperature for 5 h. THF was removed and the residue was dissolved 150 ml of $CH_2Cl_2$. The solution was washed with $H_2O$ (4×25 mL). Removal of solvent gave 10.5 gm of semi-solid. Silica gel (65 gm) was packed with 50% $CH_2Cl_2$/hexane, upon loading the sample solution, the column was eluted with 0–3% $CH_3OH/CH_2Cl_2$. The fractions were identified by TLC ($CH_3OH:CH_2Cl_2$=5:95). The fractions containing the desired product were collected and concentrated to afford 4.10 gm (99.0%) of the title product.

Synthesis of W71: To a flask was added 1.12 gm (3.18 mmol) of W70, 0.23 g (0.88 mmol) of $PPh_3$, 110 mg (0.19 mmol) of $Pd(dba)_2$, 110 mg (0.57 mmol) of CuI and 0.75 g (3.2 mmol) of Y4 (one unit wire). The flask was flushed with argon and then 65 ml of dry DMF was introduced, followed by 25 ml of diisopropylamine. The mixture was stirred at 55° C. for 2.5 h. All solvents were removed under reduced pressure. The residue was dissolved in 100 ml of $CH_2Cl_2$, and the solution was thoroughly washed with the saturated EDTA solution (2×100 mL). The Removal of $CH_2Cl_2$ gave 2.3 g of crude product. Silica gel (30 gm) was packed with 50% $CH_2Cl_2$/hexane, upon loading the sample solution, the column was eluted with 10% ethyl acetate/$CH_2Cl_2$. The concentration of the fractions containing the desired product gave 1.35 gm (2.94 mmol) of the title product, which was further purified by recrystallization from hot hexane solution as colorless crystals.

Example 5

Synthesis of Nucleoside Attached to an Insulator

As shown in FIG. 13.

Synthesis of C108: To a flask was added 2.0 gm (3.67 mmol) of 2'-amino-5'-O-DMT uridine, 1.63 gm (3.81 mmol) of C44, 5 ml of TEA and 100 ml of dichloromethane. This reaction mixture was stirred at room temperature over for 72 hrs. The solvent was removed and dissolved in a small volume of $CH_2Cl_2$ Silica gel (35 gm) was packed with 2% $CH_3OH/1\%$ TEA/$CH_2Cl_2$, upon loading the sample solution, the column was eluted with the same solvent system. The fractions containing the desired product were pooled and concentrated to afford 2.5 gm (80.4%) of the title product.

Synthesis of C109: To a flask was added 2.4 gm (2.80 mmol) of C108, 4 ml of diisopropylethylamine and 80 ml of $CH_2Cl_2$ under presence of argon. The reaction mixture was cooled in an ice-water bath. Once cooled, 2.10 gm (8.83 mmol) of 2-cyanoethyl diisopropylchloro-phosphoramidite was added. The mixture was then stirred overnight. The reaction mixture was diluted by adding 10 ml of methanol and 150 ml of $CH_2Cl_2$. This mixture was washed with a 5% $NaHCO_3$ solution, dried over sodium sulfate and then concentrated for column chromatography. A 65 gm-silica gel column was packed in 1% TEA and Hexane. The crude product was loaded and the column was eluted with 1% TEA/ 0–20% $CH_2Cl_1$/Hexane. The fractions containing the desired product were pooled and concentrated to afford 2.69 gm (90.9%) of the title product.

Example 6

Synthesis of an Electrode Containing Capture Nucleic Acids Containing Conductive Oligomers and Insulators Using the above techniques, and standard nucleic acid synthesis, capture probes comprising a conductive oligomer were made (hereinafter "wire-1"). Conductive oligomers with acetylene termini were made as outlined herein (hereinafter "wire-2").

HS-(CH2)16-OH (herein "insulator-2") was made as follows.

16-Bromohexadecanoic acid. 16-Bromohexadecanoic acid was prepared by refluxing for 48 hrs 5.0 gr (18.35 mmole) of 16-hydroxyhexadecanoic acid in 24 ml of 1:1 v/v mixture of HBr (48% aqueous solution) and glacial acetic acid. Upon cooling, crude product was solidified inside the reaction vessel. It was filtered out and washed with 3×100 ml of cold water. Material was purified by recrystallization from n-hexane, filtered out and dried on high vacuum. 6.1 gr (99% yield) of the desired product were obtained.

16-Mercaptohexadecanoic acid. Under inert atmosphere 2.0 gr of sodium metal suspension (40% in mineral oil) were slowly added to 100 ml of dry methanol at 0° C. At the end of the addition reaction mixture was stirred for 10 min at RT and 1.75 ml (21.58 mmole) of thioacetic acid were added. After additional 10 min of stirring, 30 ml degassed methanolic solution of 6.1 gr (18.19 mmole) of 16-bromohexadecanoic acid were added. The resulted mixture was refluxed for 15 hrs, after which, allowed to cool to RT and 50 ml of degassed 1.0 M NaOH aqueous solution were injected. Additional refluxing for 3 hrs required for reaction completion. Resulted reaction mixture was cooled with ice bath and poured, with stirring, into a vessel containing 200 ml of ice water. This mixture was titrated to pH=7 by 1.0 M HCl and extracted with 300 ml of ether. The organic layer was separated, washed with 3×150 ml of water, 150 ml of saturated NaCl aqueous solution and dried over sodium sulfate. After removal of ether material was purified by recrystalization from n-hexane, filtering out and drying over high vacuum. 5.1 gr (97% yield) of the desired product was obtained.

16-Bromohexadecan-1-ol. Under inert atmosphere 10 ml of $BH_3$·THF complex (1.0 M THF solution) were added to 30 ml THF solution of 2.15 gr (6.41.mmole) of 16-bromohexadecanoic acid at −20° C. Reaction mixture was stirred at this temperature for 2 hrs and then additional 1 hr at RT. After that time the resulted mixture was poured, with stirring, into a vessel containing 200 ml of ice/saturated sodium bicarbonate aqueous solution. Organic compounds were extracted with 3×200 ml of ether. The ether fractions were combined and dried over sodium sulfate. After removal of ether material was dissolved in minimum amount of dicloromethane and purified by silica gel chromatography (100% dicloromethane as eluent). 1.92 gr (93% yield) of the desired product were obtained.

16-Mercaptohexadecan-1-ol. Under inert atmosphere 365 mg of sodium metal suspension (40% in mineral oil) were added dropwise to 20 ml of dry methanol at 0° C. After completion of addition the reaction mixture was stirred for 10 min at RT followed by addition of 0.45 ml (6.30 mmole) of thioacetic acid. After additional 10 min of stirring 3 ml degassed methanolic solution of 1.0 gr (3.11 mmole) of 16-bromohexadecan-1-ol were added. The resulted mixture was refluxed for 15 hrs, allowed to cool to RT and 20 ml of degassed 1.0 M NaOH aqueous solution were injected. The reaction completion required additional 3 hr of reflux. Resulted reaction mixture was cooled with ice bath and poured, with stirring, into a vessel containing 200 ml of ice water. This mixture was titrated to pH=7 by 1.0 M HCl and extracted with 300 ml of ether. The organic layer was separated, washed with 3×150 ml of water, 150 ml of saturated NaCl aqueous solution and dried over sodium sulfate. After ether removal material was dissolved in minimum amount of dicloromethane and purified by silica gel chromatography (100% dicloromethane as eluent). 600 mg (70% yield) of the desired product were obtained.

A clean gold covered microscope slide was incubated in a solution containing 100 micromolar HS-$(CH_2)_{16}$—COOH in ethanol at room temperature for 4 hours. The electrode was then rinsed throughly with ethanol and dried. 20–30 microliters of wire-1+wire-2 solution (1 micromolar in 1×SSC buffer at pH 7.5) was applied to the electrode in a round droplet. The electrode was incubated at room temperature for 4 hours in a moist chamber to minimize evaporation. The wire-1 solution was then removed from the electrode and the electrode was immersed in 1×SSC buffer followed by 4 rinses with 1×SSC. The electrode was then stored at room temperature for up to 2 days in 1×SSC.

Alternatively, and preferably, either a "two-step" or "three-step" process is used. The "two-step" procedure is as follows. The wire-1+wire-2 mixture, in water at ~5–10 micromolar concentration, was exposed to a clean gold surface and incubated for ~24 hrs. It was rinsed well with water and then ethanol. The gold was then exposed to a solution of ~100 micromolar insulator thiol in ethanol for ~12 hrs, and rinsed well. Hybridization was done with complement for over 3 hrs. Generally, the hybridization solution was warmed to 50° C., then cooled in order to enhance hybridization.

The "three-step" procedure uses the same concentrations and solvents as above. The clean gold electrode was incubated in insulator solution for ~1 hr and rinsed. This procedure presumably results in an incomplete monolayer, which has areas of unreacted gold. The slide was then incubated with a mixture of wire-1 and wire-2 solution for over 24 hrs (generally, the longer the better). These wires still had the ethyl-pyridine protecting group on it. The wire solution was 5% NH40H, 15% ethanol in water. This removed the protecting group from the wire and allowed it to bind to the gold (an in situ deprotection). The slide was then incubated in insulator again for ~12 hrs, and hybridized as above.

In general, a variety of solvent can be used including water, ethanol, acetonitrile, buffer, mixtures etc. Also, the input of energy such as heat or sonication appears to speed up all of the deposition processes, although it may not be necessary. Also, it seems that longer incubation periods for both steps, for example as long as a week, the better the results.

Example 7

AC Detection Methods

Electrodes containing the different compositions of the invention were made and used in AC detection methods. The experiments were run as follows. A DC offset voltage between the working (sample) electrode and the reference electrode was swept through the electrochemical potential of the ferrocene, typically from 0 to 500 mV. On top of the DC offset, an AC signal of variable amplitude and frequency was applied. The AC current at the excitation frequency was plotted versus the DC offset.

Example 8

Comparison of Different ETM Attachments

A variety of different ETM attachments as depicted in FIG. 15 were compared. As shown in Table 1, a detection probe was attached to the electrode surface (the sequence containing the wire in the table). Positive (i.e. probes complementary to the detection probe) and negative (i.e. probes not complementary to the detection probe) control label probes were added.

Electrodes containing the different compositions of the invention were made and used in AC detection methods. The experiments were run as follows. A DC offset voltage between the working (sample) electrode and the reference electrode was swept through the electrochemical potential of the ferrocene, typically from 0 to 500 mV. On top of the DC offset, an AC signal of variable amplitude and frequency was applied. The AC current at the excitation frequency was plotted versus the DC offset.

The results are shown in Table 2, with the Y63, VI and IV compounds showing the best results.

| Metal Complexes | Redox Potential (mV) | 10 Hz | 100 Hz | 1,000 Hz | 10,000 Hz |
| --- | --- | --- | --- | --- | --- |
| I | 400 | Not clear | Not clear | Not clear | Not clear |
| II | 350 | 0.15 µA | 0.01 µA | 0.005 µA | ND |
| III (+ control) | 360 | 0.025 µA | 0.085 µA | 0.034 µA | ND |
| III (− control) | 360 | 0.022 µA | 0.080 µA | 0.090 µA | ND |
| IV | 140 | 0.34 µA | 3.0 µA | 13.0 µA | 35 µA |
| V | 400 | 0.02 µA | ND | 0.15 µA | ND |
| VI(1) | 140 | 0.22 µA | 1.4 µA | 4.4 µA | 8.8 µA |
| VI(2) | 140 | 0.22 µA | 0.78 µA | 5.1 µA | 44 µA |
| VII | 320 | 0.04 µA | ND | 0.45 µA | No Peak |
| VIII (not purified) | 360 | 0.047 µA | ND | ND | No Peak |
| Y63 | 160 | .25 µA | ND | 36 µA | 130 µA |

Not clear: There is no difference between positive control and negative control.
ND: Not determined

| Table of the Oligonucleotides Containing Different Metal Complexes | | | |
|---|---|---|---|
| Metal Complexes | Positive Control Sequence Containing Metal Complexes and Numbering | Negative Control Sequence Containing Metal Complexes and Numbering | Sequence Containing Wire on G Surface and Numbering |
| I | 5'-A(I)C (I)GA GTC CAT GGT-3' #D199_1 | 5'-A(I)G (I)CC TAG CTG GTG-3' #D200_1 | 5'-ACC ATG GAC TCT GT($U_W$)-3' #D201_1,2 |
| II | 5'-A(II)C (II)GA GTC CAT GGT-3' #D211_1,2 | 5'-A(II)G (II)CC TAG CTG GTG-3' #D212_1 | 5'-ACC ATG GAC TCT GT($U_W$)-3' #D201_1,2 |
| III | 5'-AAC AGA GTC CAT GGT-3' #D214_1 | 5'-ATG TCC TAG CTG GTG-3' #D57_1 | 5'-ACC ATG GAC TCT GT($U_W$)-3' #D201_1,2 |
| IV | 5'-A(IV)C (IV)GA GTC CAT GGT-3' #D215_1 | 5'-A(IV)G (IV)CC TAG CTG GTG-3' #D216_1 | 5'-ACC ATG GAC TCT GT($U_W$)-3' #D201_1,2 |
| V | 5'-A(V)C (V)GA GTC CAT GGT-3' #D203_1 | 5'-A(V)G (V)CC TAG CTG GTG-3' #D204_1 | 5'-ACC ATG GAC TCA GA($U_W$)-3' #D83_17,18 |
| VI | 5'-A(VI)C AGA GTC CAT GGT-3' #D205_1 | 5'-A(VI)G TCC TAG CTG GTG-3' #D206_1 | 5'-ACC ATG GAC TCT GT($U_W$)-3' #D201_1,2 |
| VI | 5'-A(VI)* AGA GTC CAT GGT-3' #D207_1 | 5'A(VI)* TCC TAG CTG GTG-3' #D208_1 | 5'-ACC ATG GAC TCT GT($U_W$)-3' #D201_1,2 |
| VII | 5'-A(VII)C (VII)GA GTC CAT GGT-3' #D158_3 | 5'-A(VII)G (VII)CC TAG CTG GTG-3' #D101_2 | 5'-ACC ATG GAC TCA GA($U_W$)-3' #D83_17,18 |
| VIII | 5'-A(VIII)C (VIII)GA GTC CAT GGT-3' #D217_1,2,3 | 5'-A(VIII)G (VIII)CC TAG CTG GTG-3' #D218_1 | 5'-ACC ATG GAC TCA GA($U_W$)-3' #D83_17,18 |

Example 9

Preferred Embodiments of the Invention

A variety of systems have been run and shown to work well, as outlined below. All compounds are referenced in the Figures. Generally, the systems were run as follows. The surfaces were made, comprising the electrode, the capture probe attached via an attachment linker, the conductive oligomers, and the insulators, as outlined above. The other components of the system, including the target sequences, the capture extender probes, and the label probes, were mixed and generally annealed at 90° C. for 5 minutes, and allowed to cool to room temperature for an hour. The mixtures were then added to the electrodes, and AC detection was done.

Use of a Capture Probe, a Capture Extender Probe, an Unlabeled Target Sequence and a Label Probe A capture probe D112, comprising a 25 base sequence, was mixed with the Y5 conductive oligomer and the M44 insulator at a ratio of 2:2:1 using the methods above. A capture extender probe D179, comprising a 24 base sequence perfectly complementary to the D112 capture probe, and a 24 base sequence perfectly complementary to the 2tar target, separated by a single base, was added, with the 2tar target. The D179 molecule carries a ferrocene (using a C15 linkage to the base) at the end that is closest to the electrode. When the attachment linkers are conductive oligomers, the use of an ETM at or near this position allows verification that the D179 molecule is present. A ferrocene at this position has a different redox potential than the ETMs used for detection. A label probe D309 (dendrimer) was added, comprising a 18 base sequence perfectly complementary to a portion of the target sequence, a 13 base sequence linker and four ferrocenes attached using a branching configuration. A representative scan is shown in FIG. 16A. When the 2tar target was not added, a representative scan is shown in FIG. 16B. No further representative scans are shown.

Use of a Capture Probe and a Labeled Target Sequence

Example A: A capture probe D94 was added with the Y5 and M44 conductive oligomer at a 2:2:1 ratio with the total thiol concentration being 833 μM on the electrode surface, as outlined above. A target sequence (D336) comprising a 15 base sequence perfectly complementary to the D94 capture probe, a 14 base linker sequence, and 6 ferrocenes linked via the N6 compound was used. A representative scan is shown in FIG. 20A. The use of a different capture probe, D109, that does not have homology with the target sequence, served as the negative control.

Example B: A capture probe D94 was added with the Y5 and M44 conductive oligomer at a 2:2:1 ratio with the total thiol concentration being 833 μM on the electrode surface, as outlined above. A target sequence (D429) comprising a 15 base sequence perfectly complementary to the D94 capture probe, a C131 ethylene glycol linker hooked to 6 ferrocenes linked via the N6 compound was used. A representative scan is shown in FIG. 20B. The use of a different capture probe, D109, that does not have homology with the target sequence, served as the negative control.

Use of a Capture Probe, a Capture Extender Probe, an Unlabeled Target Sequence and Two Label Probes with Long Linkers Between the Target Binding Sequence and the ETMs The capture probe D112, Y5 conductive oligomer, the M44 insulator, and capture extender probe D179 were as outlined above. Two label probes were added: D295 comprising an 18 base sequence perfectly complementary to a portion of the target sequence, a 15 base sequence linker and six ferrocenes attached using the N6 linkage depicted in the Figures. D297 is the same, except that it's 18 base sequence hybridizes to a different portion of the target sequence.

Use of a Capture Probe, a Capture Extender Probe, an Unlabeled Target Sequence and Two Label Probes with Short Linkers Between the Target Binding Sequence and the ETMs The capture probe D112, Y5 conductive oligomer, the M44 insulator, and capture extender probe D179 were as outlined above. Two label probes were added: D296 comprising an 18 base sequence perfectly complementary to a portion of the target sequence, a 5 base sequence linker and six ferrocenes attached using the N6 linkage depicted in FIGS. 22A–22B. D298 is the same, except that it's 18 base sequence hybridizes to a different portion of the target sequence.

Use of Two Capture Probes, Two Capture Capture Extender Probes, an Unlabeled Large Target Sequence and Two Label Probes with Long Linkers Between the Target Binding Sequence and the ETMs This test was directed to the detection of rRNA. The Y5 conductive oligomer, the M44 insulator, and one surface probe D350 that was complementary to 2 capture sequences D417 and EU1 were used as outlined herein. The D350, Y5 and M44 was added at a 0.5:4.5:1 ratio. Two capture extender probes were used; D417 that has 16 bases complementary to the D350 capture probe and 21 bases complementary to the target sequence, and EU1 that has 16 bases complementary to the D350 capture probe and 23 bases complementary to a different portion of the target sequence. Two label probes were added: D468 comprising a 30 base sequence perfectly complementary to a portion of the target sequence, a linker comprising three glen linkers as shown in FIG. 15 (comprising polyethylene glycol) and six ferrocenes attached using N6. D449 is the same, except that it's 28 base sequence hybridizes to a different portion of the target sequence, and the polyethylene glycol linker used (C131) is shorter.

Use of a Capture Probe, an Unlabeled Target, and a Label Probe

Example A: A capture probe D112, Y5 conductive oligomer and the M44 insulator were put on the electrode at 2:2:1 ratio with the total thiol concentration being 833 $\mu$M. A target sequence MT1 was added, that comprises a sequence complementary to D112 and a 20 base sequence complementary to the label probe D358 were combined; in this case, the label probe D358 was added to the target sequence prior to the introduction to the electrode. The label probe contains six ferrocenes attached using the N6 linkages depicted in the Figures. The replacment of MT1 with NC112 which is not complementary to the capture probe resulted in no signal; similarly, the removal of MT1 resulted in no signal.

Example B: A capture probe D334, Y5 conductive oligomer and the M44 insulator were put on the electrode at 2:2:1 ratio with the total thiol concentration being 833 $\mu$M. A target sequence LP280 was added, that comprises a sequence complementary to the capture probe and a 20 base sequence complementary to the label probe D335 were combined; in this case, the label probe D335 was added to the target prior to introduction to the electrode. The label probe contains six ferrocenes attached using the N6 linkages depicted in the Figures. Replacing LP280 with the LN280 probe (which is complementary to the label probe but not the capture probe) resulted in no signal.

I claim:
1. A modified nucleoside having the formula:

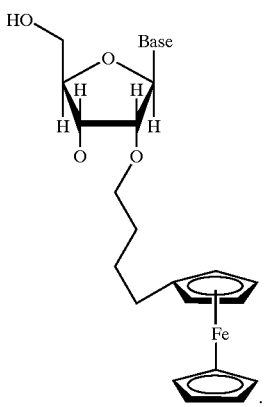

2. A modified nucleoside having the formula:

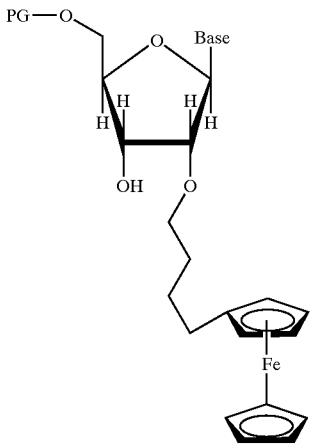

wherein PG is a protecting group.

3. A modified nucleoside having the formula:

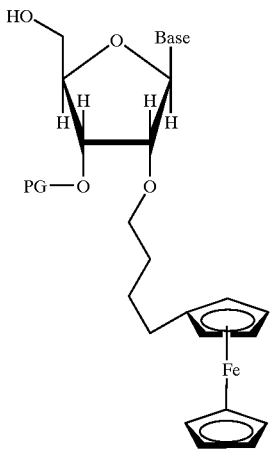

wherein PG is a protecting group.

4. A modified nucleoside according to claim 1, 2, or 3, wherein said base is selected from the group consisting of adenine, thymine, cytosine, guanine, and uracil.

5. A phosphoramidite modified nucleoside having the formula:

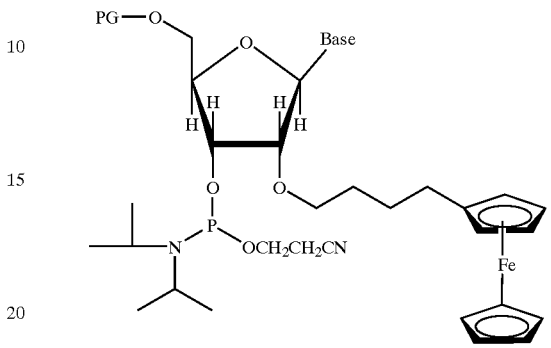

wherein PG is a protecting group.

6. A phosphoramidite modified nucleoside according to claim 5, wherein said base is selected from the group consisting of adenine, thymine, cytosine, guanine, and uracil.

7. A nucleic acid comprising at least one modified nucleoside according to claim 1.

8. A nucleic acid comprising a plurality of modified nucleosides according to claim 1.

9. A nucleic acid comprising at least four modified nucleosides according to claim 1, wherein said modified nucleosides are separated by at least one unmodified nucleoside.

10. A nucleic acid comprising at least six modified nucleosides according to claim 1 wherein said modified nucleosides are separated by at least one unmodified nucleoside.

11. A nucleic acid comprising at least ten modified nucleosides according to claim 1 wherein said modified nucleosides are separated by at least one unmodified nucleoside.

12. A method of making a nucleic acid by incorporating at least one phosphoramidite modified nucleoside comprising:

a) providing a modified nucleoside according to claim 1;
b) converting said modified nucleoside into a phosphoramidite modified nucleoside;
c) adding said phosphoramidite modified nucleoside to a growing nucleic acid, wherein said nucleic acid is attached to a solid oligomeric support.

* * * * *